(12) United States Patent
Feldmann et al.

(10) Patent No.: US 7,838,489 B2
(45) Date of Patent: Nov. 23, 2010

(54) METHODS OF TREATING RHEUMATOID ARTHRITIS WITH P75 TNF-ALPHA RECEPTOR AND METHOTREXATE

(75) Inventors: Marc Feldmann, London (GB); Ravinder Nath Maini, London (GB)

(73) Assignee: The Mathilda and Terence Kennedy Institute of Rheumatology Trust, London (GB)

( * ) Notice: Subject to any disclaimer, the term of this patent is extended or adjusted under 35 U.S.C. 154(b) by 0 days.

(21) Appl. No.: 12/287,340

(22) Filed: Oct. 7, 2008

(65) Prior Publication Data

US 2009/0175859 A1   Jul. 9, 2009

Related U.S. Application Data

(60) Division of application No. 11/225,631, filed on Sep. 12, 2005, which is a continuation of application No. 09/754,004, filed on Jan. 3, 2001, now abandoned, which is a continuation of application No. 08/690,775, filed on Aug. 1, 1996, now Pat. No. 6,270,766.

(51) Int. Cl.
*A61K 38/19*   (2006.01)
*A01N 43/58*   (2006.01)

(52) U.S. Cl. ............................................. 514/1; 514/251

(58) Field of Classification Search ........................ None
See application file for complete search history.

(56) References Cited

U.S. PATENT DOCUMENTS

| | | | |
|---|---|---|---|
| 4,695,459 | A | 9/1987 | Steinman et al. |
| 5,096,906 | A | 3/1992 | Mandell et al. |
| 5,204,329 | A | 4/1993 | Ackerman et al. |
| 5,260,422 | A | 11/1993 | Clark et al. |
| 5,298,396 | A | 3/1994 | Kotzin et al. |
| 5,317,019 | A | 5/1994 | Bender et al. |
| 5,468,481 | A | 11/1995 | Sharma et al. |
| 5,502,066 | A | 3/1996 | Heinemann et al. |
| 5,580,873 | A | 12/1996 | Bianco et al. |
| 5,656,272 | A | 8/1997 | Le et al. |
| 5,658,570 | A | 8/1997 | Newman et al. |
| 5,672,347 | A | 9/1997 | Aggarwal et al. |
| 5,698,195 | A | 12/1997 | Le et al. |
| 5,741,488 | A | 4/1998 | Feldmann et al. |
| 5,795,967 | A | 8/1998 | Aggarwal et al. |
| 5,919,452 | A | 7/1999 | Le et al. |
| 5,958,413 | A | 9/1999 | Anagnostopulos et al. |
| 5,994,510 | A | 11/1999 | Adair et al. |
| 6,015,557 | A | 1/2000 | Tobinick et al. |
| 6,177,077 | B1 | 1/2001 | Tobinick |
| 6,190,691 | B1 | 2/2001 | Mak |
| 6,270,766 | B1 | 8/2001 | Feldman et al. |
| 6,770,279 | B1 | 8/2004 | Feldmann et al. |
| 2002/0010180 | A1 | 1/2002 | Feldmann et al. |
| 2002/0068057 | A1 | 6/2002 | Feldmann et al. |
| 2002/0136723 | A1 | 9/2002 | Feldmann et al. |
| 2004/0228863 | A1 | 11/2004 | Feldmann et al. |
| 2006/0099212 | A1 | 5/2006 | Feldmann et al. |

FOREIGN PATENT DOCUMENTS

| | | |
|---|---|---|
| AU | A-58976/90 | 2/1991 |
| AU | 92/17649 | 3/1992 |
| AU | 93/51522 | 10/1993 |
| AU | 1997/021229 | 2/1997 |
| AU | 2003/264629 | 12/2003 |
| CN | 2021369 A1 | 1/1991 |
| EP | 0 240 344 A2 | 10/1987 |
| EP | 0 288 088 A2 | 10/1988 |
| EP | 40 06 269 A1 | 8/1991 |
| EP | 0 914 157 B1 | 10/2005 |
| EP | 1 941 904 | 7/2008 |
| GB | 2 246 569 A | 2/1992 |
| GB | 2246569 | 2/1992 |
| GB | 0 663 836 B1 | 7/1997 |
| WO | WO 89/08460 | 9/1989 |
| WO | WO 90/15152 | 12/1990 |
| WO | WO 90/15152 A1 | 12/1990 |
| WO | WO 91/00092 A1 | 1/1991 |
| WO | WO 91/02078 A | 2/1991 |
| WO | WO 91/10722 A2 | 7/1991 |
| WO | WO 92/07076 A1 | 4/1992 |
| WO | WO 92/07585 A1 | 5/1992 |
| WO | WO 92/08474 A2 | 5/1992 |
| WO | WO 92/11383 | 7/1992 |

(Continued)

OTHER PUBLICATIONS

Preliminary Opinion issued Jul. 13, 2009 by the Opposition Division of the European Patent Office in connection with Oppositions filed against counterpart European Patent Application No. 97933799.5, filed Aug. 1, 1997.

(Continued)

*Primary Examiner*—Phillip Gambel
(74) *Attorney, Agent, or Firm*—John P. White; Cooper & Dunham LLP

(57) ABSTRACT

Methods for treating and/or preventing a TNF-mediated disease in an individual are disclosed. Also disclosed is a composition comprising methotrexate and an anti-tumor necrosis factor antibody. TNF-mediated diseases include rheumatoid arthritis, Crohn's disease, and acute and chronic immune diseases associated with transplantation.

10 Claims, 8 Drawing Sheets

FOREIGN PATENT DOCUMENTS

| WO | WO 92/16553 A1 | 9/1992 |
|----|----------------|--------|
| WO | WO 93/07863 A  | 4/1993 |
| WO | WO 94/06476    | 3/1994 |
| WO | WO 94/08619 A  | 4/1994 |
| WO | WO 94/08619 A1 | 4/1994 |
| WO | WO 95/03827 A  | 2/1995 |
| WO | WO 95/09652 A1 | 4/1995 |
| WO | WO 96/33204 A1 | 10/1996 |
| WO | WO 98/24463 A2 | 6/1998 |
| WO | WO 98/05357 A1 | 12/1998 |
| WO | WO 00/50079    | 8/2000 |

OTHER PUBLICATIONS

Response to Patentee's May 18, 2007 submission including an Amendment to the Consolidated List of References Submitted by the Patentee with Letter of May 18, 2007, submitted Jan. 28, 2008 by Opponent, Amgen, in connection with the Oppositions against counterpart European Patent No. EP 0 914 157, granted Oct. 5, 2005.
Response to Opponent Amgen's Jan. 28, 2008 submission submitted Sep. 29, 2008 in connection with the Oppositions against counterpart European Patent No. EP 0 914 157, granted Oct. 5, 2005.
Response to Patentee's Sep. 29, 2008 submission submitted Jan. 26, 2009 by Opponent, Amgen, in connection with the Oppositions against counterpart European Patent No. EP 0 914 157, granted Oct. 5, 2005.
Breedveld, F.C. et al., "New Perspectives on Treating Rheumatoid Arthritis," *New England Journal of Medicine*, 1995, 333(3), 183-184.
Bologna, C. et al., "Association of Methotrexate (MTX) and Steroids in the Treatment of Rheumatoid Arthritis (RA) Patients," *Arthritis & Rheumatism*, 1995, 38, S366, Abstract #1280.
O'Dell, J. et al., "Treatment of rheumatoid arthritis with methotrexate alone, sulfasalazine and hydroxycholoroquine, or a combination of all three medications," *New England Journal of Medicine*, 1996, 334(20): 1287-1291.
Canadian Office Action, issued Nov. 3, 2009, in connection with counterpart Canadian Patent Application No. 2,261,630, filed Aug. 1, 1997.
Dec. 3, 2009 Response to the Jul. 24, 2009 Official Communication issued by the European Patent Office in connection with counterpart European Divisional Patent Application No. 5 076 131, filed Aug. 1, 1997, including a Main Request and Auxiliary Request.
Schröder, O. et al., (2004) "Infliximab and Methotrexate in fistulising Crohn's disease resistant or intolerant to azathioprine," *Aliment Pharmacol. Ther.*, 19: 295-301.
European Medicines Agency (EMEA): Remicade, European Public Assessment Report (EPAR) Scientific Discussion, Jun. 1, 2006.
Katsicas M., & Russo R., (2009) "Use of adalimumab in patients with juvenile idiopathic arthritis refractory to etanercept and/or infliximab," *Clin. Rheumatology*, 28: 985-988.
European Medicines Agency (EMEA) : Post-Authorisation Summary of Positive Opinion for Humira, Jul. 24, 2008.
Perez-Guijo, V. et al., (2007) "Increased efficacy of infliximab associated with methotrexate in ankylosing spondylitis," *Revue du Rhumatisme*, 74: 470-474.
Communication forwarding Nov. 23, 2009 Observations by Opponent, Abbott Laboratories, issued Dec. 4, 2009 in connection with the Oppositions against counterpart European Patent No. EP 0 914 157, granted Oct. 5, 2005, including the Nov. 23, 2009 Observations.
Office Action issued Dec. 24, 2009 in connection with U.S. Appl. No. 11/225,631, filed Sep. 12, 2005.
Jan. 22, 2010 Response to Jul. 13, 2009 Communication by Opposition Division in connection with the Oppositions to counterpart European Patent No. EP 0 914 157, granted Oct. 5, 2005.
Harrison's Principles of Internal Medicine, Fourteenth Edition, 1998, Ed: Fauci, A.S. et al., McGraw-Hill, pp. 1753 and 1760.
Scheidereit et al., In "Protein Phosphorylation in Cell Growth Regulation" Ed Michael J. Clemens, 1996, Harwood Academic Publishers GmbH, Netherlands., pp. 184-186.
Communication forwarding Jan. 25, 2010 Observations by Opponent, Wyeth, issued Feb. 4, 2010, in connection with the Oppositions against counterpart European Patent No. EP 0 914 157, granted Oct. 5, 2005, including the Jan. 25, 2010 Observations.
Lara-Ochoa, F., et al., (1996) "Antibody-Antigen Recognition: A Canonical Structure Paradigm" *J. Mol Evol.* 43:678-684.
Fundamental Immunology, Sixth Edition, 2005, Paul, W., et al., Lippincott Williams & Wilkins and Wolters Kluwer, p. 136.
Immuno Biology, The Immune System in Health and Disease, 2001, Janeway, C., et al., Garland Publishing.
Communication pursuant to Article 94 (3) EPC issued Apr. 6, 2010 by the European Patent Office in connection with counterpart European Divisional Patent Application No. 08 005 013, filed Aug. 1, 1997.
Office Action issued Nov. 3, 2009 by the Canadian Intellectual Property Office in connection with counterpart Canadian Patent Application No. 2,261,630.
May 3, 2010 Response to the Nov. 3, 2009 Office Action issued by the Canadian Intellectual Property Office in connection with counterpart Canadian Patent Application No. 2,261,630.
Moreland, et al., *Arthritis & Rheumatism*, vol. 38, No. 11, Nov. 1995, Abstract.
Ernst Schering Prize Press Release dated Mar. 24, 2010 announcing Professors Ravinder Maini and Marc Feldmann as recipients of the 2010 Ernst Schering Prize.
May 7, 2010 Response to the Dec. 24, 2009 Office Action issued by the United States Patent and Trademark Office in connection with U.S. Appl. No. 11/225,631.
U.S. Appl. No. 07/958,248, filed Oct. 8, 1992, Marc Feldmann et al.
U.S. Appl. No. 08/607,419, filed Feb. 28, 1996, Marc Feldmann et al.
Abbas, A.K., et al. (1997) "Cellular and Molecular Immunology", 3rd ed., p. 258 (W.B. Saunders Company, Philadelphia, PA).
Abbott Laboratories Ltd. "Abbott Laboratories Receives Positive Opinion for HUMIRA Rheumatoid Arthritis Extension From European Medicines Evaluation Agency," May 6, 2004 Press Release.
Abstract of Berchtold, P., & Seitz, M., (1996) "Immunsuppression—gratwanderung zwischen iatrogenie and therapie [Immunosuppression—a tightrope walk between iatrogenic harm and therapy]," Schweizerische medizinische Wochenschrift, vol. 126, No. 38, pp. 1,603-1,609.
Abstract of Bouchart, F., et al., (1993) "Methotrexate as rescue/adjunctive immunotherapy in infant and adult heart transplantation," Journal of Heart and Lung Transplantation, vol. 12, No. 3, pp. 427-433 (May-Jun. 1993).
Abstract of Drachman, D.B., (1996) "Immunotherapy in neuromuscular disorders: current and future strategies," Muscle & Nerve, vol. 19, No. 10, pp. 1,239-1,251.
Abstract of Huang, D., et al., (1992) "Effects of anti-TNF monoclonal antibody infusion in patients with hairy cell leukaemia," British Journal of Haematology, vol. 81, No. 2, pp. 231-234.
Addendum dated Dec. 15, 2003 in connection with Australian Patent Application No. 719015 (previously 37035/97), filed Feb. 25, 1999.
Advisory Action issued Dec. 3, 2004 in connection with U.S. Appl. No. 09/754,004, filed Jan. 3, 2001.
Advisory Action issued Jan. 17, 2003 in connection with U.S. Appl. No. 08/617,737, filed May 10, 1996.
Advisory Action issued Mar. 26, 2004 in connection with U.S. Appl. No. 09/754,004, filed Jan. 3, 2001.
Advisory Action issued Mar. 31, 2004 in connection with U.S. Appl. No. 08/617,737, filed May 10, 1996.
Amended Statement of Grounds and Particulars submitted Nov. 14, 2001 in connection with Australian Patent Application No. 719015 (previously 37035/97), filed Feb. 25, 1999.
Amendment and arguments submitted Aug. 12, 2004 in connection with Japanese Patent Application No. 6-509733, filed Oct. 6, 1993.
Amendment and arguments submitted Aug. 8, 2005 in connection with Japanese Patent Application No. 5-106657, filed Mar. 10, 1994.
Amendment and arguments submitted Jan. 4, 2008 in connection with Japanese Patent Application No. 5-106657, filed Mar. 10, 1994.
Amendment submitted Apr. 19, 2005 in connection with Australian Patent Application No. 2003264629, filed Dec. 1, 2003.
Amendment submitted Apr. 2, 2002 in connection with U.S. Appl. No. 08/617,737, filed May 10, 1996.
Amendment submitted Apr. 4, 1995 in connection with European Patent Application No. 93922574.4, filed Oct. 8, 1993.

Amendment submitted Aug. 25, 1993 in connection with U.S. Appl. No. 07/958,248, filed Oct. 8, 1992.

Amendment submitted Aug. 7, 2000 in connection with U.S. Appl. No. 08/690,775, filed Aug. 1, 1996.

Amendment submitted Feb. 10, 2001 in connection with European Patent Application No. 97933799.5, filed Aug. 1, 1997.

Amendment submitted Feb. 27, 2001 in connection with European Patent Application No. 94908462.8, filed Mar. 10, 1994.

Amendment submitted Feb. 4, 2004 in connection with U.S. Appl. No. 09/754,004, filed Jan. 3, 2001.

Amendment submitted Feb. 2, 2000 in connection with Canadian Patent Application No. 2,261,630, filed Aug. 1, 1997.

Amendment submitted Jan. 20, 1999 in connection with European Patent Application No. 97933799.5 filed Aug. 1, 1997.

Amendment submitted Jan. 20, 2000 in connection with U.S. Appl. No. 09/093,450, filed Jun. 8, 1998.

Amendment submitted Jan. 29, 2002 in connection with European Patent Application No. 94908462.8, filed Mar. 10, 1994.

Amendment submitted Jan. 3, 2001 in connection with U.S. Appl. No. 09/754,004, filed Jan. 3, 2001.

Amendment submitted Jan. 31, 2008 in connection with Canadian Patent Application No. 2,146,647, filed Oct. 6, 1993.

Amendment submitted Jan. 7, 1999, in connection with U.S. Appl. No. 08/617,737, filed May 10, 1996.

Amendment submitted Jul. 26, 2004 in connection with U.S. Appl. No. 09/921,937, filed Aug. 3, 2001.

Amendment submitted Jul. 31, 2003 in connection with U.S. Appl. No. 09/093,450, filed Jun. 8, 1998.

Amendment submitted Jul. 7, 1997 in connection with U.S. Appl. No. 08/403,785, filed May 3, 1995.

Amendment submitted Jul. 8, 2004 in connection with U.S. Appl. No. 10/762,096, filed Jan. 20, 2004.

Amendment submitted Jun. 17, 2003 in connection with U.S. Appl. No. 09/754,004, filed Jan. 3, 2001.

Amendment submitted Jun. 26, 2000 in connection with European Patent Application No. 94908462.8, filed Mar. 10, 1994.

Amendment submitted Jun. 8, 1998 in connection with U.S. Appl. No. 08/690,775, filed Aug. 1, 1996.

Amendment submitted Mar. 23, 2007 in connection with Australian Patent Application No. 2003264629, filed Dec. 1, 2003.

Amendment submitted Aug. 6, 2004 in connection with U.S. Appl. No. 09/754,004, filed Jan. 3, 2001.

Amendment submitted Mar. 8, 2001 in connection with Japanese Patent Application No. 5-106657, filed Mar. 10, 1994.

Amendment submitted May 8, 2000 in connection with Canadian Patent Application No. 2,261,630, filed Aug. 1, 1997.

Amendment submitted May 23, 2000 in connection with U.S. Appl. No. 08/690,775, filed Aug. 1, 1996.

Amendment submitted Nov. 28, 2006 in connection with Canadian Patent Application No. 2,146,647, filed Oct. 6, 1993.

Amendment submitted Oct. 10, 1995 in connection with PCT International Application No. PCT/GB94/00462, filed Mar. 10, 1994.

Amendment submitted Oct. 2, 1996 in connection with U.S. Appl. No. 08/690,775, filed Aug. 1, 1996.

Amendment submitted Oct. 24, 1997 in connection with U.S. Appl. No. 08/403,785, filed May 3, 1995.

Amendment submitted Oct. 27, 2003 in connection with U.S. Appl. No. 09/921,937, filed Aug. 3, 2001.

Amendment submitted Oct. 4, 2000 in connection with Japanese Patent Application No. 6-509733, filed Oct. 6, 1993.

Amendment submitted Sep. 3, 1997 in connection with U.S. Appl. No. 08/690,775, filed Aug. 1, 1996.

Amendment submitted Sep. 4, 1997 in connection with U.S. Appl. No. 08/607,419, filed Feb. 28, 1996.

Amendment, including Exhibit A and B submitted Jan. 26, 2002 in connection with European Patent Application No. 97933799.5, filed Aug. 1, 1997.

Amendment, including Exhibits 1 and 2 submitted Aug. 6, 2004 in connection with U.S. Appl. No. 09/754,004, filed Jan. 3, 2001.

Amendment, including Exhibits A to C submitted Jun. 17, 2003 in connection with U.S. Appl. No. 09/754,004, Jan. 3, 2001.

Amendment, including incorrect claims submitted Feb. 3, 2003 in connection with European Patent Application No. 97933799.5, filed Aug. 1, 1997.

Amendment, including correct claims submitted Feb. 3, 2003 in connection with European Patent Application No. 97933799.5, filed Aug. 1, 1997.

Annotated Statement of Grounds and Particulars submitted Nov. 14, 2001 in connection with Australian Patent Application No. 719015 (previously 37035/97), filed Feb. 25, 1999.

Applicants Submission in Support of its Extension of Time Application dated Dec. 2, 2003 in connection with Australian Patent Application No. 719015 (previously 37035/97), filed Feb. 25, 1999.

Arend, W.P., and Dayer, J.M. (1990) "Cytokines and cytokine inhibitors or antagonists in rheumatoid arthritis" Arthritis Rheum. 33(3):305-315.

Bach, J.F. (1993) "Immunosuppressive therapy of autoimmune diseases" Trends Pharmacol. Sci. 14:213-216.

Barrera, P., et al. (1991) "Effects of a weekly Dosis of Methotrexate on IL-1, TNF and IL-6 in patients with rheumatoid arthritis," Cytokine 3(5):504 (Abstract 330).

Barrera, P., et al. (1995) "Effect of methotrexate alone or in combination with sulphasalazine on the production and circulating concentrations of cytokines and their antagonists. Longitudinal evaluation in patients with rheumatoid arthritis" Br. J. Rheumatol. 34:747-755.

Barrera, P., et al., (1996) "Effects of antirheumatic agents on cytokines," Seminars in Arthritis and Rheumatism, vol. 25, No. 4, pp. 234-253.

Barrera, P., et al., (1993) "Circulating soluable tumor necrosis factor receptors, interleukin-2 receptors, tumor necrosis factor α, and interleukin-6 levels in rheumatoid arthritis," Arthritis & Rheumatism 36:1070-1079.

Barrera, P., et al., (1994) "Circulating concentrations and production of cytokines and soluble receptors in rheumatoid arthritis patients: effectsa of a single dose methotrexate," British Journal of heumatology 33: 1017-1024.

Barrera, P., et al., (1996) "Effects of antirheumatic agents on cytokines," Seminars in Arthritis and Rheumatism 25: 234-253.

Berchtold, et al., (1996) "Immunsuppression-gratwanderung zwischen iatrogenie and therapie (Immunosuppression-a tightrope walk between iatrogenic harm and therpy)," Schweizerische medizinische Wochenschrift 126:1603-1609 (abstract only).

Blackburn, W.D., Jr., (1996) "Management of ostearthritis and rheumatoid arthritis: prospects and possibilities," The American Journal of Medicine 100: 2A-24S-2A-30S.

Boers, M., et al., (1997) "Randomised comparison of combined step-down prednisolone, methotrexate and sulphasalazine with sulphasalazine alone in early rheumatoid arthritis," Lancet, vol. 350, No. 9074, pp. 309-318.

Bolling, S.F., et al. (1992) "Prolongation of cardiac allograft survival in rats by anti-TNF and cyclosporine combination therapy", Transplantation 53(2) :283-286.

Bologna, C., & Sany, J., (1996) "Association des traîtements de fond dans la polyarthrite rhumatoïde," La Presse Médicale, vol. 25, No. 19, pp. 876-878 (original).

Bologna, C., & Sany, J., (1996) "Association des traîtements de fond dans la polyarthrite rhumatoïde," La Presse Médicale, vol. 25, No. 19, pp. 876-878 (translation).

Borigini, M.J., and Paulus, H.E. (1995) "Combination therapy", Baillière's Clinical Rheumatology, 9(4) :689-710.

Bouchart, F., et al., (1993) "Methotrexate as rescue/adjunctive immunotherapy in infant and adult heart transplant," Journal of Heart and Lung Transplantation 12: 427-433 (abstract only).

Brahn, E., et al. (1989) "Effects of Tumor Necrosis Factor and Combination Cyclosporin A/Methotrexate Therapy on Collagen Arthritis" Arthritis Rheum. 32(4 Suppl.) :S133, abstract D42.

Breedveld, F.C., and de Vries, R.R.P. (1992) "Anti-CD4 antibodies in rheumatoid arthritis," Clin. Exp. Rheumatol. 10:325-326.

Brennan, F.M. (1994) "Role of cytokines in experimental arthritis" Clin. Exp. Immunol. 97:1-3.

Brennan, F.M., et al. (1989) "Inhibitory Effect of TNFα Antibodies on Synovial Cell Interleukin-1 Production in Rheumatoid Arthritis," Lancet 2(8657) :244-247.

Brennan, F.M., et al. (1992) "TNFα—a Pivotal Role in Rheumatoid Arthritis?" Br. J. Rheumatol. 31(5):293-298.
Brief on Appeal submitted Sep 3, 1999, including Appendix in connection with U.S. Appl. No. 08/690,775, filed Aug. 1, 1996.
Brief on Appeal, including Appendix submitted Apr. 11, 2001 in connection with U.S. Appl. No. 09/093,450, filed Jun. 8, 1998.
Brief on Appeal, including Appendix submitted Mar. 29, 2000 in connection with U.S. Appl. No. 08/617,737, filed May 10, 1996.
Butler, D.M., et al., (1995) "Modulation of proinflammatory cytokine release in rheumatoid synovial membrane cell cultures. Comparison of monoclonal anti-TNFα antibody with the interleukin-1 receptor antagonist," Eur. Cytokine Netw., 6(4):225-230.
Chikanza, I.C., and Fernandes, L. (1996) "The current status and future prospects for biological targeted therapies for rheumatoid arthritis" Exp. Opin. Invest. Drugs 5(7):819-828.
Choy, E.H.S., et al., (1995) "Therapeutic monoclonal antibodies" Br. J. Rheumatol. 34:707-715.
Claims and abstract submitted Dec. 1, 2003 in connection with Australian Patent Application No. 2003264629, filed Dec. 1, 2003.
Claims and abstract submitted Jul. 24, 2007 in connection with Australian Patent Application No. 200720367, filed Jul. 29, 2007.
Claims submitted Aug. 4, 2000 in connection with Australian Patent Application No. 51825/00, filed Aug. 4, 2000.
Cobbold, S.P., et al. (1984) "Therapy with monoclonal antibodies by elimination of T-cell subsets in vivo", Nature 312:548-551.
Cohen, S., et al. (1993) "Comparison of the safety and efficacy of cyclosporine-A and metotrexate in refractory rheumatoid arthritis: a randomized, multi-centered, placebo-controlled trial," Rev. Esp. Reumatol. 20(1):148 (Abstract 318).
Communication issued Aug. 13, 2002 in connection with U.S. Appl. No. 09/754,004, filed Jan. 3, 2001.
Communication issued Aug. 27, 2003 in connection with European Patent Application No. 94908462.8, filed Mar. 10, 1994.
Communication issued Jan. 27, 2000 in connection with European Patent Application No. 94908462.8, filed Mar. 10, 1994.
Communication issued Jul. 17, 2001 in connection with European Patent Application No. 97933799.5, filed Aug. 1, 1997.
Communication issued Jul. 19, 2001 in connection with European Patent Application No. 94908462.8, filed Mar. 10, 1994.
Communication issued May 16, 2003 in connection with European Patent Application No. 94908462.8, filed Mar. 10, 1994.
Communication issued Nov. 15, 2007 in connection with European Patent Application No. 94908462.8, filed Mar. 10, 1994.
Communication Noting of loss of rights (R.69(1) EPC) (EPO form 2021A) issued Dec. 3, 2002 in connection with European Patent Application No. 97933799.5, filed Aug. 1, 1997.
Communication submitted Dec. 26, 2002 in connection with U.S. Appl. No. 08/617,737, filed May 10, 1996.
Communication submitted Feb. 8, 2000 in connection with Australian Patent Application No. 37035/97 (now 719015), filed Feb. 25, 1999.
Communication submitted Jan. 20, 2004 in connection with U.S. Appl. No. 08/617,737, filed May 10, 1996.
Communication submitted Jul. 18, 2000 in connection with European Patent Application No. 94908462.8, filed Mar. 10, 1994.
Communication submitted Jul. 7, 2004 in connection with U.S. Appl. No. 08/617,737, filed May 10, 1996.
Communication submitted May 10, 2002 in connection with U.S. Appl. No. 09/754,004, filed Jan. 3, 2001.
Communication submitted May 18, 2007, including List of documents cited by all parties in connection with European Patent Application No. 97933799.5, filed Aug. 1, 1995.
Communication submitted Aug. 13, 2002 in connection with U.S. Appl. No. 09/754,004, filed Jan. 3, 2001.
Communication, including amended claims submitted Apr. 29, 2005 in connection with European Patent Application No. 97933799.5, filed Aug. 1, 1997.
Communication, including amended claims, French translation of claims and German translation of claims submitted Aug. 2, 2005 in connection with European Patent Application No. 97933799.5 filed Aug. 1, 1995.
Communication, including amended German translation of claims submitted Aug. 4, 2005 in connection with European Patent Application No. 97933799.5, filed Aug. 1, 1995.
Communication, including amended list of references submitted Jan. 29, 2008 in connection with European Patent No. EP 0 914 157 B1.
Communication, including annex issued Jun. 12, 2004 in connection with European Patent Application No. 97933799.5, filed Aug. 1, 1997.
Communication, including Main Request, First Auxiliary Request, Second Auxiliary Request, submitted Mar. 29, 2005 in connection with European Patent Application No. 97933799.5, filed Aug. 1, 1997.
Communication, including Minutes of the oral proceedings before the Examining Division, Statement of Requests, Minutes of the oral proceedings before the Examining Division, New Main Request and 2nd New Main Request submitted May 13, 2005 in connection with European Patent Application No. 97933799.5, filed Aug. 1, 1995.
Communication, issued Apr. 19, 2002 in connection with European Patent Applicaiton No. 97933799.5, filed Aug. 1, 1997.
Communication, including Statement of Proposed Amendments and Notice of Entitlement submitted Apr. 16, 1999 in connection with Australian Patent Application No. 37035/97 (now 719015), filed Feb. 25, 1999.
Cooper, K.D. (1993) "New therapeutic approaches in atopic dermatitis" Clin. Rev. Allergy 11:543-559.
The International Preliminary Examination Report for PCT International Application No. PCT/GB97/02058, filed Aug. 1, 1997 on behalf of The Kennedy Institute of Rheumatology in connection with European Patent Application No. 97933799.5, filed Aug. 1, 1997.
Cronstein, B.N. (2004) "Therapeutic Cocktails for Rheumatoid Arthritis: The Mixmaster's Guide," Arthritis & Rheumatism 50(7): 2041-2043.
Curriculum Vitae of Andrew Cope submitted May 18, 2007 in connection with European Patent No. EP 0 914 157 B1 granted Oct. 5, 2005.
Debets, R., and Savelkoul, H.F.J. (1994) "Cytokine antagonists and their potential therapeutic use" Immunol. Today 15(10):455-458.
Decision of a Delegate of the Commissioner of Patents dated Dec. 15, 2003 in connection with Australian Patent Application No. 719015 (previously 37035/97), filed Feb. 25, 1999.
Decision on Appeal issued Mar. 21, 2003 in connection with U.S. Appl. No. 09/093,458, filed Jun. 8, 1998.
Decision on Petition issued Jul. 13, 1995 in connection with U.S. Appl. No. 08/403,785, filed May 3, 1995.
Decision to refuse a European Patent Application issued Aug. 27, 2003 in connection with European Patent Application No. 94908462.8, filed Mar. 10, 1994.
Declaration by Andrew Cope, submitted May 18, 2007 in connection with European Patent No. 0 914 157 B1, granted Oct. 5, 2005.
Declaration by Denis Wakefield submitted Jul. 5, 2006 in connection with European Patent No. 0 914 157 B1, granted Oct. 5, 2005.
Declaration by Elliott Chartash submitted Jul. 5, 2006 in connection with European Patent No. 0 914 157 B1, granted Oct. 5, 2005.
Declaration by Ian Portek submitted Jul. 5, 2006 in connection with European Patent No. 0 914 157 B1, granted Oct. 5, 2005.
Declaration by Oliver Sander submitted Jan. 28, 2008 in connection with European Patent No. 0 914 157 B1, granted Oct. 5, 2005.
Declaration of Marc Feldmann, Ph.D. Under 37 C.F.R. § 1.132 submitted Mar. 15, 2000 in connection with U.S. Appl. No. 09/093,450, filed Jun. 8, 1998.
Declaration of Sander J.H. van Deventer, M.D., Ph.D. and Daan W. Hommes, M.D. Under 37 C.F.R. § 1.132 in connection with U.S. Appl. No. 08/690,775, filed Aug. 1, 1996.
Drachman, D.B., (1996) "Immunotherapy in neuromuscular disorders: current and future strategies," Muscle & Nerve 19: 1239-1251 (abstract only).
Eason, J.D., et al., (1995) "Inhibition of the effects of TNF in renal allograft recipients using recombinant human dimeric tumor necrosis factor receptors," Transplantation 59: 300-305.
Elliott, M.J., and Maini, R.N. (1993) "New directions for biological therapy in rheumatoid arthritis" Int. Arch. Allergy Immunol. 104:112-125.

Elliott, M.J., et al. (1993) "Treatment of Rheumatoid Arthritis with Chimeric Monoclonal Antibodies to TNFα" Rev. Esp. Reumatol. 20(Suppl. 1):148, abstract 320.

Elliott, M.J., et al. (1993) "Treatment of Rheumatoid Arthritis with Chimeric Monoclonal Antibodies to TNFα: Safety, Clinical Efficacy and Control of the Acute-Phase Response" J. Cell. Biochem., vol. 0, Suppl. 17B:145, abstract EZ 405.

Elliott, M.J., et al. (1994) "Randomised double-blind comparison of chimeric monoclonal antibody to tumour necrosis factor α (cA2) versus placebo in rheumatoid arthritis" Lancet 344:1105-1110.

Elliott, M.J., et al., (1993) "Treatment of rheumatoid arthritis with chimeric monoclonal antibodies to tumor necrosis factor α" Arth. Rheum. 36(12): 1681-1690.

Elliott, M.J., et al., (1994) "Repeated therapy with monoclonal antibody to tumour necrosis factor α (cA2) in patients with rheumatoid arthritis" Lancet 344:1125-1127.

Elliott, M.J., et al., (1995) "TNFα blockade in rheumatoid arthritis: rationale, clinical outcomes and mechanisms of action," International Journal of Immunopharmacology 17: 141-145.

Remicade : Product Information available on the Internet (www.centerwatch.com), Apr. 20, 2007.

Enbrel: product Information available on Internet (www.medicalnewstoday.com, Apr. 20, 2007.

Examiner's Answer issued Jul. 2, 2001 in connection with U.S. Appl. No. 09/093,450, filed Jun. 8, 1998.

Examiner's Report issued Jun. 28, 2005 in connection with Australian Patent Application No. 2003264629, filed Dec. 1, 2003.

Examiner's report issued Mar. 1, 2002 in connection with Australian Patent Application No. 51825/00, filed Aug. 4, 2000.

Examiner's Report issued Sep. 2, 1999 in connection with Australian Patent Application No. 37035/97 (now 719015), filed Feb. 25, 1999.

Facsimile submitted Oct. 23, 1997 in connection with U.S. Appl. No. 08/403,785, filed May 3, 1995.

Farmer, K.M., et al. (2001) "Interleukin-17 rheumatoid arthritis (RA): production by RA synovial membrane cultures and IL-17 receptor IgG1 fusion protein treatment in rat adjuvant arthritis (AA)" Poster Session: Cytokines and Chemokines, board No. 74.

Feldmann, M., et al. (1996) "Role of cytokines in rheumatoid arthritis," Annual Review of Immunology 14:397-440.

Felson, D.T., et al., (1994) "The efficacy and toxicity of combination therapy in rheumatoid arthritis. A meta-analysis," Arthritis & Rheumatism, vol. 37, No. 10, pp. 1487-1491.

Fendly, B.M., et al. (1987) "Murine monoclonal antibodies defining neutralizing epitopes on tumor necrosis factor," Hybridoma 6: 359-369.

Fenner, H., et al., (1995) "Suppression of tumor necrosis factor (TNF) and TNF-mediated effector mechanisms by methotrexate (MTX) in patients with rheumatoid arthritis," Arthritis & Rheumatism, vol. 38, No. 9 (Suppl.), p. S266, Abstract 679.

Ferran, C., et al. (1991) "Cascade modulation by anti-tumor necrosis factor monoclonal antibody of interferon-γ, interleukin 3 and interleukin 6 release after triggering of the CD3/T cell receptor activation pathway", Eur. J. Immunol. 21:2349-2353.

Ferraz, M.B., et al. (1994) "Combination Therapy with Methotrexate and Chloroquine in Rheumatoid Arthritis. A Multicenter Randomized Placebo-controlled Trial," Scandinavian Journal of Rheumatology, vol. 12, No. 5, pp. 231-236.

Fox, D.A., (1995) "Biological therapies: a novel approach to the treatment of autoimmune disease," Am. J. Med. 99:82-88.

Fries, J.F., et al., (1990) 'Reevaluating the Therapeutic Approach to Rheumatoid Arthritis: the "Sawtooth" Strategy J. Rheumatol. 17(Suppl. 22): 12-15.

GenBank Accession AAA61200 for TNF (Jan. 14, 1995).

Genovese, M.C., et al. (2004) "Combination Therapy with Etanercept and Anakinra in the Treatment of Patients with Rheumatoid Arthritis Who Have Been Treated Unsuccessfully With Methotrexate", Arthritis & Rheumatism 50(5): 1412-1419.

Genzyme Catalog (1991) pp. 79-80.

Gorman, S.D., et al. (1991) "Reshaping a therapeutic CD4 antibody," Proc. Natl. Acad. Sci. USA 88:4181-4185.

Haagsma, C.J., et al., (1994) "Combination of methotrexate and sulphasalazine vs methrotrexate alone: a randomized open clinical trial in rheumatoid arthritis patients resistant tosulphasalazine therapy," British Journal of Rheumatology 33: 1049-1055.

Haraoui, B., (2005) "The anti-tumor necrosis factor agents are a major advance in the treatment of rheumatoid arthritis," The Journal of Rheumatology. Supplement, vol. 32, Suppl. 72, pp. 46-47.

Harris, W.J., and Emery, S. (1993) "Therapeutic antibodies—the coming of age," Trends Biotechnol. 11:42-45.

Hearing Submissions dated Dec. 1, 2003 in connection with Australian Patent Application No. 719015 (previously 37035/97), filed Feb. 25, 1999.

Hervé, P., et al. (1992) "Phase I-II Trial of a Monoclonal Anti-Tumor Necrosis Factor α Antibody for the Treatment of Refractory Severe Acute Graft-Versus-Host Disease" Blood 79(12):3362-3368.

Herzog, C., et al. (1987) "Monoclonal Anti-CD4 in Arthritis," Lancet 2 (8573):1461-1462.

Higgins, G., (1995) "Cytokine antagonism: still a main attraction in rheumatology R&D," Inpharma, vol. 994, pp. 9-10.

Hochberg, M.C., et al. (2003) "Comparison of the efficacy of the tumour necrosis factor α blocking agents adalimumab, etanercept, and infliximab when added to methotrexate in patients with active rheumatoid arthritis," Annals of the Rheumatic Diseases, vol. 62, Suppl. II, pp. ii13-ii16.

Horneff, G., et al. (1991) "Elevated Levels of Circulating Tumor Necrosis Factor—α, Interferon-γ, and Interleukin-2 in Systematic Reactions Induced by Anti-CD4 Therapy in Patients with Rheumatoid Arthritis" Cytokine 3 (3) :266-267.

Horneff, G., et al. (1991) "Treatment of Rheumatoid Arthritis with an Anti-CD4 Monoclonal Antibody" Arthritis Rheum. 34(2):129-140.

May 7, 2006, www.phoenix5.org/glossary/adjunctive_therapy.html.

Huang, D., et al., (1992) "Effects of anti-TNF monoclonal antibody infusion in patient with hairy cell leukemia," British Journal of Hematology 81: 231-234 (abstract only).

Humira: Abbott Press Release 6th May 2004.

Imagawa, D.K., et al. (1991) "The Role of Tumor Necrosis Factor in Allograft Rejection. III. Evidence that Anti-TNF Antibody Therapy Prolongs Allograft Survival in Rats with Acute Rejection", Transplantation, 51(1):57-62.

International Preliminary Examination Report mailed Nov. 2, 1994 in connection with PCT International Application No. PCT/GB93/02070, filed Oct. 6, 1993.

International Search Report for PCT International Application PCT/GB97/02058, filed Aug. 1, 1997.

International Search Report mailed Dec. 12, 1995 in connection with PCT International Application No. PCT/GB94/00462, filed Mar. 10, 1994.

International Search Report mailed Feb. 22, 1994 in connection with PCT International Application No. PCT/GB93/02070, filed Oct. 6, 1993.

International Search Report mailed Jun. 14, 1994 in connection with PCT International Application No. PCT/GB94/00462, filed Mar. 10, 1994.

Interview Summary issued Jun. 13, 2000 in connection with U.S. Appl. No. 08/690,775, filed Aug. 1, 1996.

Johnson, K., (1996) "Efficacy assessment in trials of combination therapy for rheumatoid arthritis," The Journal of Rheumatology 23(Suppl. 44) :107-109.

Kahan, B.D. (1992) "Immunosuppressive therapy" Curr. Opin. Immunol. 4 (5) :553-560.

Kalden, J.R., and Manger, B. (1995) "Biologic agents in the treatment of inflammatory rheumatic diseases" Curr. Opin. Rheum. 7:191-97.

Kalden, J.R., and Manger, B. (1997) "Biologic agents in the treatment of inflammatory rheumatic diseases" Curr. Opin. Rheumatol. 9: 206-212.

Kavanaugh, A.F, et al., (1996) "Anti-TNF-α monoclonal antibody (mAb) treatment of rheumatoid arthritis (RA) patients with active disease on methotrexate (MTX) : results of a double-blind placebo controlled multicenter trial," Arthritis & Rheumatism, vol. 39, No. 9 (Suppl.), p. S123, abstract 575.

Klareskog, L., et al., (2004) "Therapeutic effect of the combination of etanercept and methotrexate compared with each treatment alone in patients with rheumatoid arthritis: double-blind randomized controlled trial," Lancet 363:675-681.

Knight, D.M., et al., (1993) "Construction and initial characterization of a mouse-human chimeric anti-TNF antibody," Molecular Immunology 30: 1443-1453.

Kozarek, R.A., et al. (1989) "Methotrexate induces clinical and histologic remission in patients with refractory inflammatory bowel disease" Ann. Int. Med. 110:353-356.

Krause, D., et al., (2000) "Response to methotrexate treatment is associated with reduced mortality in patients with severe rheumatoid arthritis," Arthritis & Rheumatism vol. 43, No. 1, pp. 14-21.

Kremer, J.M. (1996) "Historical Overview of the Treatment of Rheumatoid Arthritis with an Emphasis on Methotrexate," *J. Rheum.* 23:Suppl. 44, pp. 34-37.

Kremer, J.M., (1995) "The changing face of therapy for rheumatoid arthritis," Rheumatic Disease Clinics of America 21: 845-852.

Kung, A.H.C., et al., (1993) (eds.) "Therapeutic Proteins, Pharmacokinetics and Pharmacodynamics," W.H. Freeman & Co., New York, USA, pub.

Lesslauer, W., et al., (1991) "Recombinant soluable tumor necrosis factor receptor proteins protect mice from lipopolysaccharide-induced lethality," European Journal of Immunology 21: 2883-2886.

Letter Accompanying Subsequently Filed Items (EPO Form 1038.1), including Opposition Brief submitted Jul. 5, 2006 in connection with European Patent No. EP 0 914 157 B1.

Letter from the United Kingdom Patent Office dated Nov. 11, 1993 in connection with PCT International Application No. PCT/GB93/02070, filed Oct. 6, 1993.

Letter from the United Kingdom Patent Office dated Oct. 12, 1993 in connection with PCT International Application No. PCT/GB93/02070, filed Oct. 6, 1993.

Letter to the United Kingdom Patent Office dated Nov. 11, 1993 in connection with PCT International Application No. PCT/GB93/02070, filed Oct. 6, 1993.

Liang, C.M., et al., (1986) Production and characterization of monoclonal antibodies against recombinant human tumor necrosisi factor/cahectin, Biochemical and Biophysical Research Communications, 137: 847-854.

Littman, B.H., et al., (1995) "Rheumatoid arthritis treated with tenidap and piroxicam. Clinical associations with cytokine modulation by tenidap" Arthritis Rheum. 38:29-37.

Lorenz, H.M., and Kalden, J.R. (2002) "Perspectives for TNF-α-targeting therapies," Arthritis Res. 4 (Suppl. 3):S17-24.

Maini, R.N. (1995) "A Perspective on Anti-cytokine and Anti-T cell-directed therapies in Rheumatoid Arthritis," Clinical and Experimental Rheumatology, vol. 13 (Suppl. 12), pp. S35-S40.

Maini, R.N., (1996) "The role of cytokines in rheumatoid arthritis. The Croonian Lecture 1995" Journal of the Royal College of Physicians of London 30(4):344-351.

Maini, R.N., et al. (1995) "Clinical response of rheumatoid arthritis (RA) to anti-TNFα (cA2) monoclonal antibody (mab) is related to administered dose and persistence of circulating antibody" Arth. Rheum. Suppl. 38(9) :S186 (Abstract 200).

Maini, R.N., et al. (1995) "Clinical response of rheumatoid arthritis (RA) to anti-TNFα (cA2) monoclonal antibody (mab) is related to administered dose and persistence of circulating antibody," Arthritis & Rheumatism, vol. 38, Suppl. 9, Abstract 200.

Maini, R.N., et al. (1995) "Infliximab (chimeric anti-tumour necrosis factor α monoclonal antibody) versus placebo in rheumatoid arthritis patients receiving concomitant methotrexate: a randomised phase III trial," Lancet, vol. 354, No. 9194, pp. 1932-1939.

Maini, R.N., et al., (1998) "Therapeutic efficacy of multiple intravenous infusion and anti-tumor necrosis factor α monoclonal antibody combined with low-dose weekly methotrexate in rheumatoid arthritis," Arthritis & Rheumatism 41: 1552-1563.

Markowitz, J., et al. (1991) "Immunology of inflammatory bowel disease: summary of the proceedings of the Subcommittee on Immunosuppresive Use in IBD" J. Pediatr. Gastroenterol. Nutr. 12(4):411-423.

Mathilda and Terence Kennedy Institute of Rheumatology Annual Scientific Report 1995, the, published Feb.-Mar. 1996, including Declaration of W. Paul Norton.

Matsumiya, G., et al., (1996) "Successful long-term concordant xenografts in primates: alteration of the immune response with methotrexate" Transplant. Proceed. 28(2) :751-753.

Merck Manual of Diagnosis and Therapy, The (1992) 16th Ed., Berkow, R. (ed.) Merck Research Laboratories, Rahway, NJ (pub.), pp. 1304-1313.

Miller, V.E. (1993) "Detection of tumour necrosis factor alpha and interleukin-1 beta in the rheumatoid osteoarthritic cartilage-pannus junction by immunohistochemical methods" Rheumatology Int. 13:77-82.

Moreland, L.W. (1996) "Intitial experience combining methotrexate with biologic agents for treating rheumatoid arthritis," The Journal of Rheumatology 23(Suppl. 44):78-83.

Moreland, L.W., (1993) "Use of a chimeric monoclonal anti-CD4 antibody in patients with refractory rheumatoid arthritis," Arthritis & Rheumatism, vol. 36, No. 3, pp. 307-318.

Moreland, L.W., et al., (1994) "Soluble tumor necrosis factor receptor (sTNFR): results of a phase I dose-escalation study in patients with rheumatoid arthritis," Clinical Research 42: 312A.

Moreland, L.W., et al., (1993) "Use of a chimeric monoclonal anti-CD4 anitbody in patients with refractory rheumatoid arthritis," Arthritis Rheum. 36: 307-318.

Moreland, L.W., et al., (1995) "Double-blind, placebo-controlled multicenter trial using chimeric monoclonal anti-CD4 antibody, cM-T412, in rheumatoid arthritis patients receiving concomitant methotrexate" Arthritis Rheum. 38:1581-1588.

Natanson, C., et al. (1994) "Selected Treatment Strategies for Septic Shock Based on Proposed Mechanisms of Pathogenesis" Ann. Int. Med. 120(9):771-783.

No author given (1996) "The American Heritage Dictionary of the English Language", 3rd ed. (Editors of The American Heritage Dictionaries, eds.), p. 80 (Houghton Mifflin Company, Boston, MA, publishers).

Notice of Allowance, including Notice of Allowability, Examiner's Amendment, Examiner's Statement of Reasons for Allowance and Interview Summary issued Oct. 28, 1997 in connection with U.S. Appl. No. 08/403,785, filed May 3, 1995.

Notice of Allowance, including Notice of Allowability, Examiner's Amendment, Examiner's Statement of Reasons for Allowance and Interview Summary issued Oct. 25, 2000 in connection with U.S. Appl. No. 08/690,775, filed Aug. 1, 1996.

Notice of Allowance, including Notice of Allowability, Examiner's Amendment, Examiner's Statement of Reasons for Allowance, Interview Summary and Examiner Interview Summary Record issued Aug. 12, 2003 in connection with U.S. Appl. No. 09/093,450, filed Jun. 8, 1998.

Notice of Informal Application issued Jun. 1, 1995 in connection with U.S. Appl. No. 08/403,785, filed May 3, 1995.

Notice of Opposition to a European Patent, including Additional Sheet for Publications and Notice of Opposition submitted Jun. 30, 2006 in connection with European Patent No. EP 0 914 157 B1.

Notice of Opposition to a European Patent, including Facts and Arguments Presented in Support of the Opposition, Additional Sheet, Annex A (List of References) and Annex B (Table of Contents) submitted Jul. 5, 2006 in connection with European Patent No. EP 0 914 157 B1.

Notice of Opposition to a European Patent, including list of Additional Representatives and Opposition submitted Jul. 5, 2006 in connection with European Patent No. EP 0 914 157 B1.

Notice of Opposition, including Statement of Grounds of Opposition submitted Jul. 5, 2006 in connection with European Patent No. EP 0 914 157 B1.

Notification of Transmittal of the International Preliminary Examination Report, including the International Preliminary Examination Report mailed Aug. 21, 1998 in connection with PCT International Application No. PCT/GB97/02058, filed Aug. 1, 1997.

Notification of Transmittal of the International Search Report or the Declaration, including the International Search Report mailed Dec. 17, 1997 in connection with PCT International Application No. PCT/GB97/02058, filed Aug. 1, 1997.

Observations of a Third Party under Art. 115 EPC submitted May 28, 2003 in connection with European Patent Application No. 94908462.8, filed Mar. 10, 1994.

O'Dell, J., et al., (1996) "Pneumococcal vaccine in rheumatoid arthritis. Decreased response while taking methotrexate," Journal of Clinical Rheumatology 2: 59-63.

O'Dell, J., et al., (1995) "The treatment of rheumatoid arthritis in 1995: results of a survey," Arthritis & Rheumatism 38: p. S366 abs. 1277.

O'Dell, J., et al., (1996) "Pneumococcal vaccine in rheumatoid arthritis. Decreased response while taking methotrexate," Journal of Clinical Rheumatology 2: 59-63.

Office Action issued Apr. 10, 2000 in connection with U.S. Appl. No. 09/093,450, filed Jun. 8, 1998.

Office Action issued Aug. 13, 2002 in connection with U.S. Appl. No. 09/754,004, filed Jan. 3, 2001.

Office Action issued Aug. 26, 2003 in connection with U.S. Appl. No. 09/921,937, filed Aug. 3, 2001.

Office Action issued Dec. 9, 1997 in connection with U.S. Appl. No. 08/607,419, filed Feb. 28, 1996.

Office Action issued Dec. 9, 1997 in connection with U.S. Appl. No. 08/690,775 filed Aug. 1, 1996.

Office Action issued Feb. 19, 1998 in connection with U.S. Appl. No. 08/617,737, filed May 10, 1996.

Office Action issued Feb. 25, 2004 in connection with U.S. Appl. No. 09/921,937, filed Aug. 3, 2001.

Office Action issued Feb. 25, 2005 in connection with U.S. Appl. No. 08/617,737, filed May 10, 1996.

Office Action issued Feb. 8, 2005 in connection with Japanese Patent Application No. 5-106657, filed Mar. 10, 1994.

Office Action issued Jan. 17, 2003 in connection with U.S. Appl. No. 09/754,004, filed Jan. 3, 2001.

Office Action issued Jan. 7, 1997 in connection with U.S. Appl. No. 08/403,785, filed May 3, 1995.

Office Action issued Jul. 20, 1999 in connection with U.S. Appl. No. 09/093,450, filed Jun. 8, 1998.

Office Action issued Jul. 22, 1997 in connection with U.S. Appl. No. 08/617,737, filed May 10, 1996.

Office Action issued Jul. 3, 2007 in connection with Japanese Patent Application No. 5-106657, filed Mar. 10, 1994.

Office Action issued Jul. 31, 2007 in connection with Canadian Patent Application No. 2,146,647, filed Oct. 6, 1993.

Office Action issued Jul. 7, 1998 in connection with U.S. Appl. No. 08/617,737, filed May 10, 1996.

Office Action issued Jun. 21, 2000 in connection with U.S. Appl. No. 08/617,737, filed May 10, 1996.

Office Action issued Jun. 25, 2002 in connection with U.S. Appl. No. 08/617,737, filed May 10, 1996.

Office Action issued Mar. 11, 2005 in connection with U.S. Appl. No. 09/754,004, filed Jan. 3, 2001.

Office Action issued Mar. 12, 2002 in connection with U.S. Appl. NO. 09/754,004, filed Jan. 3, 2001.

Office Action issued Mar. 2, 2004 in connection with Japanese Patent Application No. 6-509733, filed Oct. 6, 1993.

Office Action issued Mar. 25, 1993 in connection with U.S. Appl. No. 07/958,248, filed Oct. 8, 1992.

Office Action issued Mar. 29, 1999 in connection with U.S. Appl. No. 08/617,737, filed May 10, 1996.

Office Action issued Mar. 3, 1997 in connection with U.S. Appl. No. 08/690,775, filed Aug. 1, 1996.

Office Action issued Mar. 4, 1997 in connection with U.S. Appl. No. 08/607,419, filed Feb. 28, 1996.

Office Action issued Apr. 5, 1999 in connection with U.S. Appl. No. 09/093,450, filed Jun. 8, 1998.

Office Action issued May 31, 2006 in connection with Canadian Patent Application No. 2,146,647, filed Oct. 6, 1993.

Office Action issued Nov. 15, 2004 in connection with U.S. Appl. No. 09/921,937, filed Aug. 3, 2001.

Office Action issued Nov. 2, 2001 in connection with U.S. Appl. No. 08/617,737, filed May 10, 1996.

Office Action issued Nov. 23, 1999 in connection with U.S. Appl. No. 08/690,775, filed Aug. 1, 1996.

Office Action issued Nov. 3, 1993 in connection with U.S. Appl. No. 07/958,248, filed Oct. 8, 1992.

Office Action issued Nov. 4, 2003 in connection with U.S. Appl. No. 09/754,004, filed Jan. 3, 2001.

Office Action issued Sep. 1, 1998 in connection with U.S. Appl. No. 08/690,775, filed Aug. 1, 1996.

Office Action issued Sep. 17, 2003 in connection with U.S. Appl. No. 08/617,737, filed May 10, 1996.

Office Action issued Sep. 21, 2006 in connection with U.S. Appl. No. 10/762,096, filed Jan. 20, 2004.

Pascalis, L., et al. (1993) "Longterm efficacy and toxicity of combined cyclosporine A-steroid-methotrexate treatment in rheumatoid arthritis" Rev. Esp. Reumatol. 20(Suppl. 1):148 (abstract 319).

Paul, W. E. (1993) "Fundamental Immunology," 3rd Ed. (Raven Press, NY, publ.), p. 242.

Paul, W.E. (1993) "Fundamental Immunology," 3rd Ed. (Raven Press, NY, publ.), pp. 807-812.

PCT Written Opinion mailed Apr. 28, 1998 in connection with PCT International Application No. PCT/GB97/02058, filed Aug. 1, 1997.

Piguet, P.F., et al. (1992) "Evolution of collagen arthritis in mice is arrested by treatment with anti-tumor necrosis factor (TNF) antibody or a recombinant soluble TNF Receptor" Immunology 77:510-514.

Preliminary Amendment submitted Aug. 20, 2001 in connection with U.S. Appl. No. 08/617,737, filed May 10, 1996.

Preliminary Amendment submitted Aug. 3, 2001 in connection with U.S. Appl. No. 09/921,937, filed Aug. 3, 2001.

Preliminary Amendment submitted Jan. 20, 2004 in connection with U.S. Appl. No. 10/762,096, filed Jan. 20, 2004.

Preliminary Amendment submitted Jul. 8, 1997 in connection with U.S. Appl. No. 08/617,737, filed May 10, 1996.

Preliminary Amendment submitted Jun. 8, 1998 in connection with U.S. Appl. No. 09/093,450, filed Jun. 8, 1998.

Preliminary Amendment submitted Mar. 16, 1995 in connection with U.S. Appl. No. 08/403,785, filed May 3, 1995.

Preliminary Amendment submitted May 21, 2003 in connection with U.S. Appl. No. 09/093,450, filed Jun. 8, 1998.

Product description for adalimumab (sold as HUMIRA®), Jul. 2004.

Product description for etanercept (sold as ENBREL®), Sep. 27, 2004.

Product description for infliximab (sold as REMICADE®), Dec. 2004.

Qin, S., et al. (1987) "CD4 monoclonal antibody pairs for immunosuppression and tolerance induction" Eur. J. Immunol. 17:1159-1165.

Racadot, E., et al. (1992) "Immunological follow-up of 17 patients with rheumatoid arthritis treated in vivo with an anti-T CD4+ Monoclonal Antibody (B-F5)" Clin. Exp. Rheumatol. 10:365-374.

Ralph, P. (1993) "Clinical and Preclinical Studies Presented at the Keystone Symposium on Arthritis, Related Diseases, and Cytokines" Lymphokine Cytokine Res. 12(4):261-263.

Rankin, E.C.C., et al. (1995) "The therapeutic effects of an engineered human anti-tumour necrosis factor alpha antibody (CDP571) in rheumatoid arthritis" Br. J. Rheumatol. 34: 334-342.

Remarks submitted Jan. 3, 2001 in connection with U.S. Appl. No. 09/754,004, filed Jan. 3, 2001.

Remicade: Product Information (www.centerwatch.com), Apr. 20, 2007.

Reply filed Jan. 29, 2002 to Communication pursuant to Article 96(2) EPC issued Jul. 7, 2001 by the European Patent Office in connection with European Patent Application No. 94 908 462.8, filed Mar. 10, 1994.

Reply to Restriction Requirement submitted Apr. 16, 1998 in connection with U.S. Appl. No. 08/617,737, filed May 10, 1996.

Reply to Restriction Requirement submitted May 5, 1999 in connection with U.S. Appl. No. 09/093,450, filed Jun. 8, 1998.

Reply to Written Opinion submitted Oct. 7, 1994 in connection with PCT International Application No. PCT/GB93/02070, filed Oct. 6, 1993.

Request to Amend a Patent or Any Other Filed Documents submitted Nov. 14, 2001 in connection with Australian Patent Application No. 719015 (previously 37035/97, filed Feb. 25, 1999.

Response to Restriction Requirement submitted Nov. 20, 1997 in connection with U.S. Appl. No. 08/617,737, filed May 10, 1996.

Response, or in the Alternative, a Petition Under 37 C.F.R. 1.181 to the Notice of Informal Application submitted Jun. 15, 1995 in connection with U.S. Appl. No. 08/403,785, filed May 3, 1995.

Rezaian, M.M., (1999) "Do infliximab and methotrexate act synergisitically in the treatment of rheumatoid arthritis? Comment on the article by Maini et al.," Arthritis & Rheumatism 42: 1779.

Richardson, C., & Emery, P. (1995) "New therapies for rheumatoid arthritis" Br. J. Clin. Prac. 49(3):135-139.

Ruperto, N., et al., (2007) "A Randomized, Placebo-Controlled Trial of Infliximab Plus Methotrexate for the Treatment of Polyarticular-Course Juvenile Rheumatoid Arthritis," Arthritis & Rheumatism, vol. 56, No. 9, pp. 3096-3106.

Sander, O., et al., (1995) "Flair after discontinuation of 'ineffective' disease modifying anti rheumatic drug (DMARD) treatment in active rheumatoid arthritis (RA)," Rheumatology in Europe, vol. 24, Suppl. 3, p. 226, abstract D40.

Sander, O., et al., (1999) "Prospective six year follow up of patients withdrawn from a randomized study comparing parenteral gold salt and methotrexate," Annals of the Rheumatic Diseases, vol. 58, pp. 281-287.

Sander, O., et al., (1995) "Tumornecrosisfactor [sic] alpha (TNF) blockade enhances methotrexate (MTX) response in patients with rheumatoid arthritis (RA)," Arthritis & Rheumatism, vol. 38, No. 9 (Suppl.), p. S266, abstract 678.

Schact, E. (1993) "Gegenwärtige und zukünftige Therapiestrategien Der rheumatoiden Arthritis (RA) ["The current and future therapy strategies of rheumatoid arthritis"]" Z. Rheumatol. 52(6) :365-382.

Seitz, M., et al., (1995) "Methotrexate action in rheumatoid arthritis: stimulation of cytokine inhibitor and inhibition of chemokine production by peripheral blood mononuclear cells," British Journal of Rheumatology, vol. 34, pp. 602-609.

Seu, P., et al. (1991) "Monoclonal Anti-Tumor Necrosis Factor-α Antibody Treatment of Rat Cardiac Allografts: Synergism with Low-Dose Cyclosporine and Immunohistological Studies", J. Surg. Res. 50(5) :520-528.

Shanahan, F., et al., (1990) "Sulfasalazine inhibits the binding of TNFα to its receptor," Immunopharmacology 20: 217-224.

Sheehan, K.C.F., et al. (1989) "Generation and characterization of hamster monoclonal antibodies that neutralize murine tumor necrosis factors", J. Immunol. 142(11) :3884-3893.

Sigidin, Y.A., & Zhukovskaya, G.N. (1995) "Treatment of rheumatoid arthritis with the combination of auranofin and Methotrexate," Rheumatology in Europe, vol. 24, Suppl. 3, abstract D50.

Sosman, J.A., and Sondel, P.M. (1993) "The graft-vs.-leukemia effect. Implications for post-marrow transplant antileukemia treatment" Am. J. Pediatric Hematol. Oncol. 15(2):185-195.

St.Clair, E. W., et al., (2004) "Combination of Infliximab and Methotrexate Therapy for Early Rheumatoid Arthritis," Arthritis & Rheumatism 50(11): 3432-3443.

Statement of Abbott submitted Oct. 5, 2007 by Biotechnology, Inc. in connection with Australian Patent Application No. 2003264629, filed Dec. 1, 2003.

Statement of Grounds and Particulars dated Nov. 16, 2004 in connection with Australian Patent Application No. 719015 (previously 37035/97), filed Feb. 25, 1999.

Statement of Grounds and Particulars submitted Oct. 5, 2007 by Amgen Inc. in connection with Australian Patent Application No. 2003264629, filed Dec. 1, 2003.

Statement of Grounds submitted Jan. 6, 2004 in connection with European Patent Application No. 94908462.8, filed Mar. 10, 1994.

Statement of Grounds and Particulars in Support of Opposition submitted Oct. 5, 2007 by Wyeth in connection with Australian Patent Application No. 2003264629, filed Dec. 1, 2003.

Statutory Declaration of Denis Wakefield, including Annexure DW-1 dated Apr. 15, 2002 in connection with Australian Patent Application No. 719015 (previously 37035/97), filed Feb. 25, 1999.

Statutory Declaration of Denis Wakefield, including Exhibit DW-2 dated Oct. 10, 2005 in connection with Austrialian Patent Application No. 719015 (previously 37035/97), filed Feb. 25, 1999.

Statutory Declaration of Eric Morand, including Exhibits EM-1 to EM-11 in connection with Australian Patent Application No. 719015 (previously 37035/97), filed Feb. 25, 1999.

Statutory Declaration of Ian Portek, including Annexure IP-1 dated Apr. 6, 2002 in connection with Australian Patent Application No. 719015 (previously 37035/97), filed Feb. 25, 1999.

Statutory Declaration of Ian Portek, including Exhibits IP-1 to IP-4 dated Oct. 20, 2005 in connection with Australian Patent Application No. 719015 (previously 37035/97), filed Feb. 25, 1999.

Statutory Declaration of Jack Edelman, including Annexures JE-1 and JE-2 dated Oct. 5, 2005.

Statutory Declaration of Kenneth Muirden, including Exhibits KDM-1 and KDM-2 dated Nov. 28, 2003 in connection with Australian Patent Application No. 719015 (previously 37035/97), filed Feb. 25, 1999.

Statutory Declaration of Paul Anthony Power dated Dec. 1, 2003 in connection with Australian Patent Application No. 719015 (previously 37035/97), filed Feb. 25, 1999.

Statutory Declaration of Peter Michael Brooks, including Exhibit PB-1 dated Jan. 9, 2004 in connection with Australian Patent Application No. 719015 (previously 37035/97), filed Feb. 25, 1999.

Stedman, T.L. (1995) "Stedman's Medical Dictionary", 26th ed. (Spraycar, M., ed.), pp. 105 and 108 (Williams & Wilkins, Baltimore, MD, publishers).

Stein, C.M. et al., (1994) "Combination therapy with cyclosporine and methotrexate: results of a 24 week extension study subsequent to a 24 week double blind study," Arthritis & Rheumatism, vol. 37, No. 9 (Suppl.), p. S252, abstract 552.

Steinbrüchel, D.A., et al. (1991) "Monoclonal Antibody Treatment (Anti-CD4 and Anti-Interleukin-2 Receptor) combined with Cyclosporin A has a Positive but not Simple Dose-Dependent Effect on Rat Renal Allograft Survival," Scand. J. Immunol. 34:627-633.

Strand, V., et al. (1993) "Effects of administration of an anti-CD5 plus immunoconjugate in rheumatoid arthritis. Results of two phase II studies," Arthritis & Rheumatism, vol. 36, No. 5, pp. 620-630.

Strober, S., and Holoshitz, J. (1990) "Mechanisms of Immune Injury in Rheumatoid Arthritis: Evidence for the Involvement of T Cells and Heat-Shock Protein," Immunol. Rev. 118:233-255.

Stuart, J.M., and Kang, A.H. (1986) "Monkeying Around with Collagen Autoimmunity and Arthritis" Lab. Invest. 54(1) :1-3.

Sugihara, M., et al., (2007) "Effects of Infliximab Therapy on Gene Expression Levels of Tumor Necrosis Factor α Tristetraprolin, T cell Intracellular Antigen 1, and Hu Antigen R in Patients With Rheumatoid Arthritis," Arthritis & Rheumatism, vol. 56, No. 7, pp. 2160-2169.

Summons to attend oral proceedings pursuant to Rule 71(1) EPC, including Annex to the communication issued Apr. 26, 2004 in connection with European Patent Application No. 97933799.5, filed Aug. 1, 1997.

Summons to Attend Oral Proceedings Pursuant to Rule 71(1) EPC, including Communication of the Technical Board of Appeal issued Feb. 23, 2005 in connection with European Patent Application No. 94908462.8, filed Mar. 10, 1994.

The Mathilda and Terence Kennedy Institute of Rheumatology Annual Scientific Report 1995 including Declaration of W. Paul Norton.

Third Party Observations, including Exhibit 1 (PCT International Publication Nos. WO 95/09652 A, published Apr. 13, 1995, and WO 94/08619 A, published Apr. 28, 1994) submitted Feb. 28, 2002 in connection with European Patent Application No. 97933799.5, filed Aug. 1, 1997.

Third Party Observations, including signed Declaration of W. Paul Norton, dated Jun. 24, 2003 submitted Jul. 9, 2003 in connection with European Patent Application No. 97933799.5, filed Aug. 1, 1997

Third Party Observations, including The Mathilda and Terence Kennedy Institute of Rheumatology Annual Scientific Report 1995 and unsigned Declaration of W. Paul Norton, dated Jun. 2003 submitted Jun. 12, 2003 in connection with European Patent Application No. 97933799.5, filed Aug. 1, 1997.

Thorbecke, G.J., et al. (1992) "Involvement of endogenous tumor necrosis factor α and transforming growth factor β during induction of collagen type II arthritis in mice" Proc. Natl. Acad. Sci. USA 89:7375-7379.

Tisch, R., and McDevitt, H.O. (1994) "Antigen-specific immunotherapy: Is it a real possibility to combat T-cell-mediated autoimmunity?" Proc. Natl. Acad. Sci. USA 91:437-438.

Tugwell, P., et al., (1995) "Combination therapy with cyclosporine and methotrexate in severe rheumatoid arthritis. The methotrexate-cyclosporine combination study group," New England Journal of Medicine 333: 137-141.

van de Lubbe, P.A., et al. (1994) "Lack of clinical effect of CD4 monoclonal antibody therapy in early rheumatoid arthritis; a placebo controlled trial," Arthritis & Rheumatism, vol. 37 (Suppl.), p. S294, abstract 807.

Van Der Lubbe, P.A., et al., (1994) "Treatment of rheumatoid arthritis with a chimeric CD4 monoclonal antibody (cm-t412): immunopharmacological aspects and methods of action," Scandinavian Journal of Immunology 39: 286-294.

Van Der Lubbe, P.A., et al., (1995) "A randomized, double-blind, placebo-controlled study of CD4 monoclonal antibody therapy in early rheumatoid arthritis." Arth. Rheum. 38(8): 1097-1106.

Van Dullemen, H.M., et al., (1995) "Treatment of Crohn's disease with anti-tumor necrosis factor chimeric monoclonal antibody (cA2)." Gastroenterology 109: 129-135.

van Oosten, B.W., et al., (1996) "Increased MRI activity and immune activation in two multiple sclerosis patients treated with the monoclonal anti-tumor necrosis factor antibody cA2," Neurology, vol. 47, pp. 1531-1534.

Van Ostade, X., et al., (1994) "Structure-activity studies of human tumour necrosis factors," Protein Engineering, vol. 7, No. 1, pp. 5-22.

Verhoeven, A.C., et al. (1998) "Combination therapy in rheumatoid arthritis: updated systematic review" Br. J. Rheumatol. 37:612-619.

Voluntary Amendment submitted Apr. 7, 1995 in connection with Canadian Patent Application No. 2,146,647, filed Oct. 6, 1993.

Voluntary Amendment submitted Jan. 29, 2001 in connection with Canadian Patent Application No. 2,146,647, filed Oct. 6, 1993.

Voluntary Amendment submitted Oct. 12, 2000 in connection with Canadian Patent Application No. 2,146,647, filed Oct. 6, 1993.

Waldmann, T.A. (1991) "Monoclonal Antibodies in Diagnosis and Therapy," Science 252:1657-1662.

Watts, R.A., and Isaacs, J.D. (1992) "Immunotherapy of rheumatoid arthritis" Ann. Rheum. Dis. 51:577-579.

Webster's 3rd International Dictionary: "adjunct" and "adjuctive", May 7, 2006.

Weinblatt, M.E. (1995) "Methrotrexate for Chronic Diseases in Adults." *New Engl. J. Med.* 332:141-145.

Weinblatt, M.E., (1995) "Methotrexate for chronic diseases in adults," New England Journal of Medicine, vol. 332, No. 5, pp. 330-331.

Weinblatt, M.E., et al. (1999) "A trial of etanercept, a recombinant tumor necrosis factor receptor:Fc fusion protein, in patients with rheumatoid arthritis receiving methotrexate, " New England Journal of Medicine, vol. 340, No. 4, pp. 253-259.

Weinblatt, M.E., et al. (2003) "Adalimumab, a Fully Human Anti-Tumor Necrosis Factor α Monoclonal Antibody, for the Treatment of Rheumatoid Arthritis in Patients Taking Concomitant Methotrexate: the ARMADA trial," Arthritis & Rheumatism, vol. 48, No. 1, pp. 35-45.

Weinblatt, M.E., et al., (1994) "Methotrexate in rheumatoid arthritis. A five-year prospective multicenter study" Arthritis Rheum. 37(10):1492-1498.

Weinblatt, M.E., (1995) "Efficacy of methotrexate in rheumatoid arthritis," British Journal of Rheumatology, vol. 34 (Suppl. 2), pp. 43-48.

Wilkens, R.F., et al. (1995) "Comparison of azathioprine, methotrexate, and the combination of the two in the treatment of rheumatoid arthritis. A forty-eight-week controlled clinical trial with radiologic outcome assessment." Arthritis Rheum. 38:1799-1806.

Williams, H.J., et al. (1992) "Comparison of auranofin, methotrexate, and the combination of both in the treatment of rheumatoid arthritis. A controlled clinical trial," Arthritis & Rheumatism, vol. 35, No. 3, pp. 259-269.

Williams, R.O., et al. (1992) "Anti-tumor necrosis factor ameliorates joint disease in murine collagen-induced arthritis", Proc. Natl. Acad. Sci. USA 89(20):9784-9788.

Williams, R.O., et al. (1994) "Synergy between anti-CD4 and anti-tumor necrosis factor in the amelioration of established collagen-induced arthritis" Proc. Natl. Acad. Sci. USA 91(7):2762-2766.

Williams, R.O., et al. (1995) "Successful therapy of collagen-induced arthritis with TNF receptor-IgG fusion protein and combination with anti-CD4" Immunology 84:433-439.

Wilske, K.R. & Yocum, D.E., (1996) "Consensus statement. Rheumatoid arthritis: the status and future of combination therapy," p. 110.

Winter, G., & Harris, W.J. (1993) "Humanized antibodies," Immunology Today, vol. 14, No. 6, pp. 243-246.

Wooley, P.H., (1993) "Influence of a recombinant human soluble tumor necrosis factor receptor FC fusion protein on type II collagen-induced arthritis in mice," The Journal of Immunology 151:6602-6607.

Wooley, P.H., et al., (1993) "Influence of a recombinant human soluble tumor necrosis factor receptor FC fusion protein on type II collagen-induced arthritis in mice," The Journal of Immunology, vol. 151, No. 11, pp. 6,602-6,607.

Written Opinion mailed Jul. 13, 1994 in connection with PCT International Application No. PCT/GB93/02070, filed Oct. 6, 1993.

Written Opinion mailed Jul. 14, 1995 in connection with PCT International Application No. PCT/GB94/00462, filed Mar. 10, 1994.

Yocum, D.E., (1991) "Combined DMARDS un rheumatoid arthritis: past, present and future," Progress in Inflammation Research and Therapy 117-121.

Office Action issued Mar. 26, 2008 in connection with Canadian Patent Application No. 2,146,647, filed Oct. 6, 1993.

Amendment submitted Apr. 21, 2008 in connection with Canadian Patent Application No. 2,146,647, filed Oct. 6, 1993.

Office Action issued Dec. 21, 2007 in connection with U.S. Appl. No. 11/255,631, filed Sep. 12, 2005.

Preliminary Amendment submitted Jan. 12, 2006 in connection with U.S. Appl. No. 11/255,631, filed Sep. 12, 2005.

Preliminary Amendment submitted Jan. 18, 2007 in connection with U.S. Appl. No. 11/255,631, filed Sep. 12, 2005.

Preliminary Amendment submitted Sep. 12, 2005 in connection with U.S. Appl. No. 11/255,631, filed Sep. 12, 2005.

Preliminary Amendment, including Exhibits A to C submitted Jan. 11, 2006in connection with U.S. Appl. No. 11/255,631, filed Sep. 12, 2005.

International Preliminary Examination Report mailed Dec. 18, 1995 in connection with PCT International Application No. PCT/GB94/00462, filed Mar. 10, 1994.

Summons to Attend Oral Proceedings Pursuant to Rule 71(1) EPC, including Communication issued Mar. 11, 2003 in connection with European Patent Application No. 94908462.8, filed Mar. 10, 1994.

Decision of Rejection issued Mar. 4, 2008 in connection with Japanese Patent Application No. 5-106657, filed Mar. 10, 1994.

Verhoeven, A.C., et al. (1998) "Combination therapy in rheumatoid arthritis: updated systematic review," Br. J. Rheumatol. 37(6):612-619.

www.arthritis.org/conditions/DiseaseCenter/default.asp, retrieved Mar. 31, 2002.

www.arthritis.org/research/research_program/RA/challenge, retrieved Jun. 23, 2002.

Amendment, including submitted Jun. 23, 2008 in connection with U.S. Appl. No. 11/225,631, filed Sep. 12, 2005.

Elliott, M.J. et al., "Treatment of Rheumatoid Arthritis With Chimeric Monoclonal Antibodies to Tumor Necrosis Factor α," *Arthritis & Rheumatism*, vol. 36, No. 12, Dec. 1993, pp. 1681-1690.

Elliott, M.J. et al., "Randomised Double-Blind Comparison of Chimeric Monoclonal Antibody to Tumour Necrosis Factor α (cA2) Versus Placebo in Rheumatoid Arthritis," *The Lancet*, vol. 344, Oct. 22, 1994, pp. 1105-1109.

Felson, D.T. et al., "The Efficacy and Toxicity of Combination Therapy in Rheumatoid Arthritis," *Arthritis & Rheumatism*, vol. 37, No. 10, Oct. 1994, pp. 1487-1492.

*KSR International Co. v. Teleflex Inc.*, 550 U.S. 398, 127 S. Ct. 1727, 82 U.S.P.Q. 2d 1385 (2007).

Weinblatt, M. et al., "Selective Costimulation Modulation Using Abatacept in Patients With Active Rheumatoid Arthritis While Receiving Etanercept: a Randomised Clinical Trial," *Ann Rheum Dis.* 2007; 66:228-234.

Genovese, M.C. et al., "Combination Therapy With Etanercept and Anakinra in the Treatment of Patients With Rheumatoid Arthritis Who Have Been Treated Unsuccessfully With Methotrexate," *Arthritis & Rheumatism*, vol. 50, No. 5, May 2004, pp. 1412-1419.

Lipsky, P.E. et al., "Infliximab and Methotrexate in the Treatment of Rheumatoid Arthritis," *New England Journal of Medicine*, vol. 343, No. 22, Nov. 30, 2000, pp. 1594-1602.

Maini, R.N. et al., "Sustained Improvement Over Two Years in Physical Function, Structural Damage, and Signs and Symptoms Among Patients With Rheumatoid Arthritis Treated With Infliximab and Methotrexate," *Arthritis &Rheumatism*, vol. 50, No. 4, Apr. 2004, pp. 1051-1065.

Smolen, J. S. et al., "Evidence of Radiographic Benefit of Treatment With Infliximab Plus Methotrexate in Rheumatoid Arthritis Patients Who Had No Clincial Improvement," *Arthritis & Rheumatism*, vol. 52, No. 4, Apr. 2005, pp. 1020-1030.

FDA Approved Labeling for Remicade®, Apr. 14, 2009.

Lasker Foundation press release dated Sep. 14, 2003 announcing Marc Feldmann and Sir Ravinder N. Maini as recipients of Lasker Award.

European Patent Office press release naming Marc Feldmann as European Inventor of the Year 2007.

Letter from Harlan Weisman and Paul Stoffels, Johnson & Johnson, to Dr. Marc Feldmann announcing Drs. Feldmann and Maini as 2008 recipients of Dr. Paul Jannssen Award for Biomedical Research.

Crawford Prize press release dated Jan. 13, 2000 announcing Professors Ravinder Maini and Marc Feldmann as recipients of the 2000 Crawford Prize.

Humira® advertisement, excerpted from *Arthritis & Rheumatism*, vol. 60, No. 1, Jan. 2009.

Van Der Heijde, D. et al., "Comparison of Etanercept and Methotrexate, Alone and Combined, in the Treatment of Rheumatoid Arthritis," *Arthritis & Rheumatism*, vol. 54, No. 4, Apr. 2006, pp. 1063-1074.

Diller, W., "Anti-TNFs Continue to Shine in a Pharmaceutical Market Beset By Problems," The Pink Sheet®, vol. 70, No. 49, Dec. 8, 2008, pp. 18-20.

Manual of Medical Therapeutics, 25$^{th}$ Edition, Orian et al (editors) Dept of Medicine, Washington University, St. Louis, MO, pp. 308-309 (1986).

Bologna, C. et al., "Association of Methotrexate (MTX) and Steroids in the Treatment of Rheumatoid Arthritis (RA) Patients," *Arthritis & Rheumatism*, 1995, 38, S366, Abstract #1280.

Statutory Declaration of Leslie Schrieber including a Curriculum Vitae served Nov. 5, 2008 by Opponent, Abbott Bioresearch Center, in connection with Oppositions to counterpart Australian Patent Application No. 2003/264629, filed Dec. 1, 2003.

Kingsley, G. and Panayi, G., "The immunopathogenesis of rheumatoid arthritis," *British Journal of Rheumatology*, 1991, 30, Suppl. 2, 3-4.

Feldmann, M. et al. "Cytokine production in the rheumatoid joint: implications for treatment," *Annals of Rheumatic Diseases*, 1990, 49, 480-486.

Kremer, J.M. et al., "The Mechanism of Action of Methotrexate in Rheumatoid Arthritis: The Search Continues," *J. Rheumatol.*, 1994, 21, 1-5.

O'Dell, J.R. et al., "Methotrexate Use in Rheumatoid Arthritis," *Rheumatic Disease Clinics of North America*, Edited by Cash, J.M., 23, 1997, 779-796, W.B. Sounders, Philadelphia.

Statutory Declaration of Leslie Glen Cleland including Guidelines for Expert Witnesses in Proceedings in the Federal Court of Australia and Curriculum Vitae served Nov. 5, 2008 by Opponent, Wyeth, in connection with Oppositions to counterpart Australian Patent Application No. 2003/264629, filed Dec. 1, 2003.

Diagrammatic representation of the cells and mediators involved in the inflammation of the joints seen in rheumatoid arthritis, Dec. 1, 2003.

Conaghan, P.G., et al., "Anti-Rheumatic Drug-Prescribing Behavior of Australasian Rheumatologists 1984-1994," *British Journal of Rheumatology*, 1997, 36, 487-490.

Moreland, L.W. et al., "Soluble tumor necrosis factor receptor (sTNFR): results of a phase I dose-escalation study in patients with rheumatoid arthritis," *Arthritis & Rheumatism*, 1994, 37(9), Suppl., S295, Abstract #813.

Csuka, M. Et Al., "Treatment of Intractable Rheumatoid Arthritis With Combined Cyclophosphamide, Azathioprine, and Hydroxychloroquine," *Rheumatoid Arthritis*, 1986, 255(17), 2315-2319.

Statutory Declaration of Milton Laurence Cohen including a Curriculum Vitae served Jan. 13, 2009 by Opponent, Abbott Bioresearch Center, in connection with Oppositions to counterpart Australian Patent Application No. 2003/264629, filed Dec. 1, 2003.

Sandborn, W.J. et al., "Etanercept for Active Crohn's Disease: A Randomised, Doouble-Blind, Placebo Controlled Trial," *Gastroenterology*, 2001, 121, 1088-1094.

Office Action issued Apr. 20, 2009 in connection with Australian Patent Application No. 2007/203067, filed Jul. 29, 2007.

Declaration of W. Paul Norton submitted Jul. 9, 2003 by a Third Party under Article 115 EPC in connection with counterpart European Patent Application No. 97933799.5, filed Aug. 1, 1997.

Communication pursuant to Article 94(3) EPC issued Oct. 30, 2008 by the European Patent Office in connection with counterpart European Patent Application No. 05076131.1, filed Aug. 1, 1997.

Result of Consultation issued Nov. 27, 2008 by the European Patent Office in connection with counterpart European Patent Application No. 05076131.1, filed Aug. 1, 1997.

Response to an Oct. 30, 2008 Communication of the European Patent Office submitted Mar. 9, 2009 in connection with counterpart European Patent Application No. 05076131.1, filed Aug. 1, 1997.

European Examination Report issued Jul. 24, 2009 by the European Patent Office in connection with counterpart European Patent Application No. 05076131.1, filed Aug. 1, 1997.

Result of Consultation issued Aug. 11, 1009 by the European Patent Office in connection with counterpart European Patent Application No. 05076131.1, filed Aug. 1, 1997.

Communication forwarding European Search Report and European Search Opinion issued Aug. 7, 2009 in connection with the counterpart European Patent Application No. 08005013.1, filed Mar. 18, 2008, including the European Search Report.

European Search Opinion issued Aug. 7, 2009 in connection with the counterpart European Patent Application No. 08005013.1, filed Mar. 18, 2008.

Huizinga, T.W.J. and Breedveld, F.C., "Cytokine—suppressive-anti-inflammatory drugs—Status of development in rheumatoid arthritis," *Clinical Immunotherapeutics*, 1996, 6(5), 395-404.

Phillips, G.L. et al., "Prophylaxis for acute graft-versus host disease following unrelated donor bone marrow transplantation," *Bone Marrow Transplantation*, 1995, 15(2), 213-219.

Nevill et al., *Journal of Cellular Biochemistry*, 1992, Suppl. 16A, 209.

Van Vollenhoven, R.F. et al., *Lancet*, Aug. 8; 374(9688) :459-66 (2009).

Office Action issued Apr. 15, 2009 in connection with U.S. Appl. No. 11/225,631, filed Sep. 12, 2005.

Interview Summary issued Aug. 13, 2009 in connection with U.S. Appl. No. 11/225,631, filed Sep. 12, 2005.

Amendment filed Sep. 15, 2009 in connection with U.S. Appl. No. 11/225,631, filed Sep. 12, 2005.

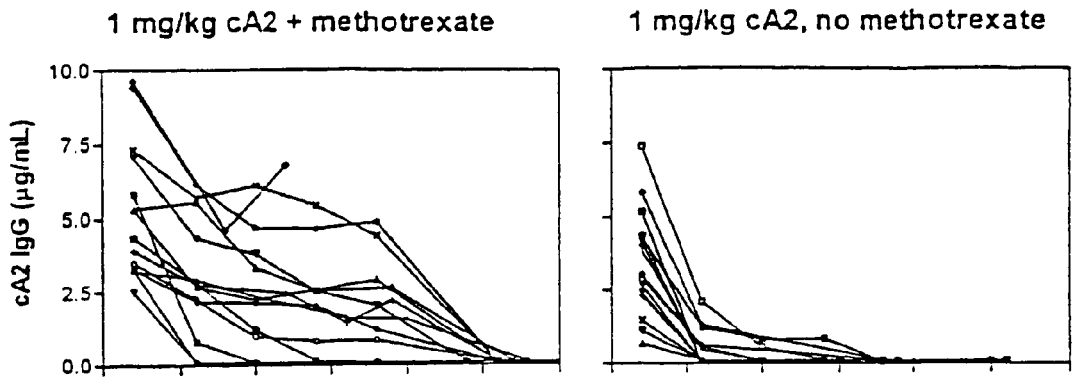
FIGURE 7A
FIGURE 7B
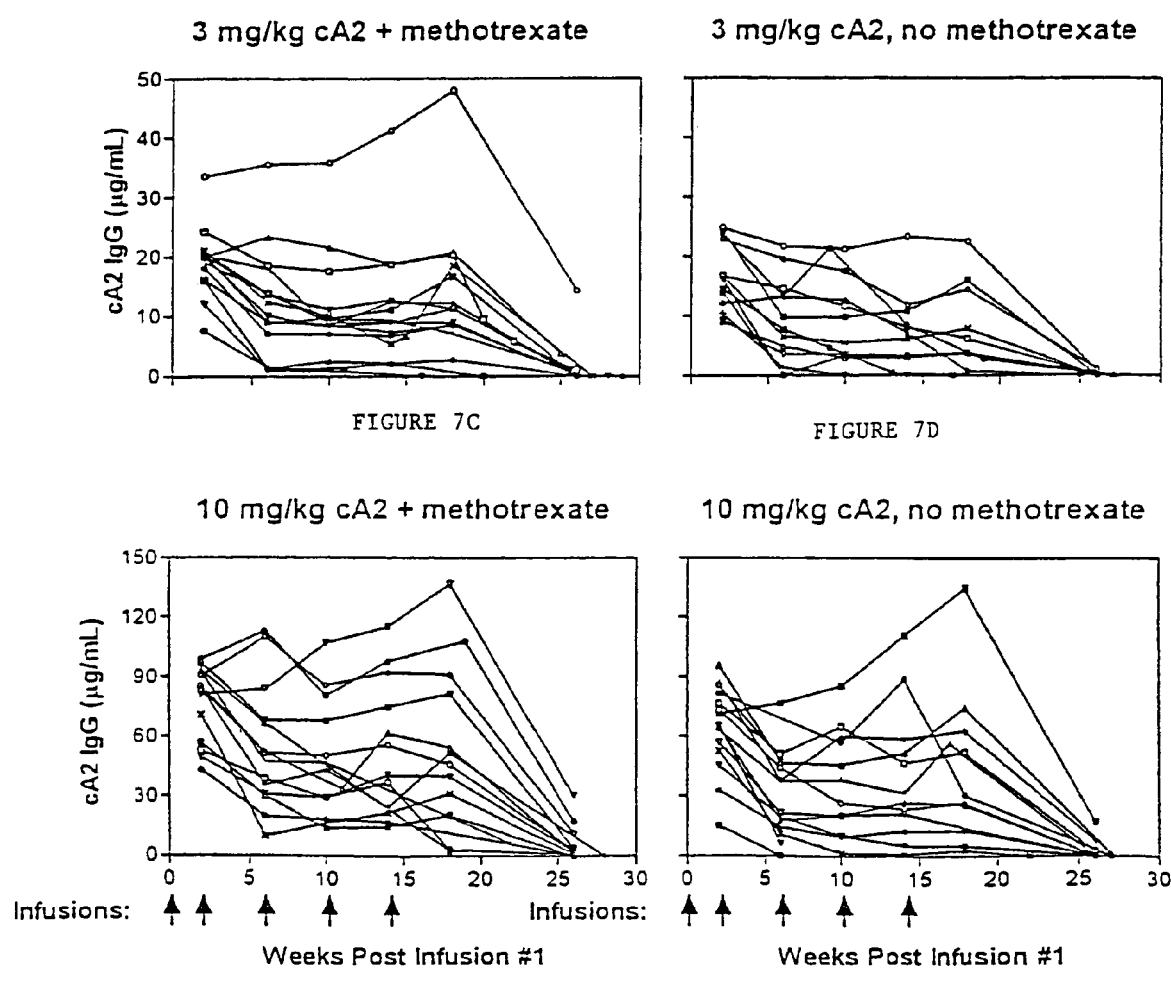
FIGURE 7C
FIGURE 7D
FIGURE 7E
FIGURE 7F

METHODS OF TREATING RHEUMATOID ARTHRITIS WITH P75 TNF-ALPHA RECEPTOR AND METHOTREXATE

RELATED APPLICATIONS

This application is a divisional of U.S. Ser. No. 11/225,631, filed Sep. 12, 2005, which is a continuation of U.S. Ser. No. 09/754,004, filed Jan. 3, 2001, now abandoned, which is a continuation of U.S. Ser. No. 08/690,775, filed Aug. 1, 1996, now U.S. Pat. No. 6,270,766 B1, issued Aug. 7, 2001.

BACKGROUND OF THE INVENTION

Monocytes and macrophages secrete cytokines known as tumor necrosis factor alpha (TNFα) and tumor necrosis factor beta (TNFβ) in response to endotoxin or other stimuli. TNFα is a soluble homotrimer of 17 kD protein subunits (Smith et al., *J. Biol. Chem.* 262:6951-6954 (1987)). A membrane-bound 26 kD precursor form of TNF also exists (Kriegler et al., *Cell* 53:45-53 (1988)). For reviews of TNF, see Beutler et al., *Nature* 320:584 (1986); Old, *Science* 230:630 (1986); and Le et al., *Lab. Invest.* 56:234 (1987).

Cells other than monocytes or macrophages also produce TNFα. For example, human non-monocytic tumor cell lines produce tumor necrosis factor (TNF) (Rubin et al., *J. Exp. Med.* 164:1350 (1986); Spriggs et al., *Proc. Natl. Acad. Sci. USA* 84:6563 (1987)). CD4+ and CD8+ peripheral blood T lymphocytes and some cultured T and B cell lines (Cuturi et al., *J. Exp. Med.* 165:1581 (1987); Sung et al., *J. Exp. Med.* 168:1539 (1988); Turner et al., *Eur. J. Immunol.* 17:1807-1814 (1987)) also produce TNFα.

TNF causes pro-inflammatory actions which result in tissue injury, such as degradation of cartilage and bone, induction of adhesion molecules, inducing procoagulant activity on vascular endothelial cells (Pober et al., *J. Immunol.* 136:1680 (1986)), increasing the adherence of neutrophils and lymphocytes (Pober et al., *J. Immunol.* 138:3319 (1987)), and stimulating the release of platelet activating factor from macrophages, neutrophils and vascular endothelial cells (Camussi et al., *J. Exp. Med.* 166:1390 (1987)).

Recent evidence associates TNF with infections (Cerami et al., *Immunol. Today* 9:28 (1988)), immune disorders, neoplastic pathologies (Oliff et al., *Cell* 50:555 (1987)), autoimmune pathologies and graft-versus-host pathologies (Piguet et al., *J. Exp. Med.* 166:1280 (1987)). The association of TNF with cancer and infectious pathologies is often related to the host's catabolic state. Cancer patients suffer from weight loss, usually associated with anorexia.

The extensive wasting which is associated with cancer, and other diseases, is known as "cachexia" (Kern et al., *J. Parent. Enter. Nutr.* 12:286-298 (1988)). Cachexia includes progressive weight loss, anorexia, and persistent erosion of body mass in response to a malignant growth. The fundamental physiological derangement can relate to a decline in food intake relative to energy expenditure. The cachectic state causes most cancer morbidity and mortality. TNF can mediate cachexia in cancer, infectious pathology, and other catabolic states.

TNF also plays a central role in gram-negative sepsis and endotoxic shock (Michie et al., *Br. J. Surg.* 76:670-671 (1989); Debets et al., *Second Vienna Shock Forum*, p. 463-466 (1989); Simpson et al., *Crit. Care Clin.* 5:27-47 (1989)), including fever, malaise, anorexia, and cachexia. Endotoxin strongly activates monocyte/macrophage production and secretion of TNF and other cytokines (Kornbluth et al., *J. Immunol.* 137:2585-2591 (1986)). TNF and other monocyte-derived cytokines mediate the metabolic and neurohormonal responses to endotoxin (Michie et al., *New Engl. J. Med.* 318:1481-1486 (1988)). Endotoxin administration to human volunteers produces acute illness with flu-like symptoms including fever, tachycardia, increased metabolic rate and stress hormone release (Revhaug et al., *Arch. Surg.* 123:162-170 (1988)). Circulating TNF increases in patients suffering from Gram-negative sepsis (Waage et al., *Lancet* 1:355-357 (1987); Hammerle et al., *Second Vienna Shock Forum* p. 715-718 (1989); Debets et al., *Crit. Care Med.* 17:489-497 (1989); Calandra et al., *J. Infect. Dis.* 161:982-987 (1990)).

Thus, TNFα has been implicated in inflammatory diseases, autoimmune diseases, viral, bacterial and parasitic infections, malignancies, and/or neurogenerative diseases and is a useful target for specific biological therapy in diseases, such as rheumatoid arthritis and Crohn's disease. Beneficial effects in open-label trials with a chimeric monoclonal antibody to TNFα (cA2) have been reported with suppression of inflammation (Elliott et al., *Arthritis Rheum.* 36:1681-1690 (1993); Elliott et al., *Lancet* 344:1125-1127 (1994)). See also, Van Dullemen et al., *Gastroenterology* 109:129-135 (1995). Beneficial results in a randomized, double-blind, placebo-controlled trial with cA2 have also been reported with suppression of inflammation (Elliott et al., *Lancet* 344:1105-1110 (1994)).

SUMMARY OF THE INVENTION

The present invention is based on the discovery that treatment of patients suffering from a TNF-mediated disease with a tumor necrosis factor antagonist, such as an anti-tumor necrosis factor antibody, as adjunctive and/or concomitant therapy to methotrexate therapy produces a rapid and sustained reduction in the clinical signs and symptoms of the disease. The present invention is also based on the unexpected and dramatic discovery that a multiple dose regimen of a tumor necrosis factor antagonist, such as an anti-tumor necrosis factor antibody, when administered adjunctively with methotrexate to an individual suffering from a TNF-mediated disease produces a highly beneficial or synergistic clinical response for a significantly longer duration compared to that obtained with a single or multiple dose regimen of the antagonist administered alone or that obtained with methotrexate administered alone. As a result of applicants' invention, a method is provided herein for treating and/or preventing a TNF-mediated disease in an individual comprising co-administering an anti-TNF antibody or a fragment thereof and methotrexate to the individual in therapeutically effective amounts. In a particular embodiment, methotrexate is administered in the form of a series of low doses separated by intervals of days or weeks.

A method is also provided herein for treating and/or preventing recurrence of a TNF-mediated disease in an individual comprising co-administering an anti-TNF antibody or a fragment thereof and methotrexate to the individual in therapeutically effective amounts. TNF-mediated diseases include rheumatoid arthritis, Crohn's disease, and acute and chronic immune diseases associated with an allogenic transplantation (e.g., renal, cardiac, bone marrow, liver, pancreatic, small intestine, skin or lung transplantation).

Therefore, in one embodiment, the invention relates to a method of treating and/or preventing rheumatoid arthritis in an individual comprising co-administering an anti-TNF antibody or a fragment thereof and methotrexate to the individual in therapeutically effective amounts. In a second embodiment, the invention relates to a method of treating and/or preventing Crohn's disease in an individual comprising co-administering an anti-TNF antibody or a fragment thereof and methotrexate to the individual in therapeutically effective amounts. In a third embodiment, the invention relates to a method of treating and/or preventing other autoimmune diseases and/or acute or chronic immune disease associated with a transplantation in an individual, comprising co-administering an anti-TNF antibody or a fragment thereof and methotrexate to the individual in therapeutically effective amounts.

A further embodiment of the invention relates to compositions comprising an anti-TNF antibody or a fragment thereof and methotrexate.

In addition to anti-TNF antibodies, TNF antagonists include anti-TNF antibodies and receptor molecules which bind specifically to TNF; compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; and compounds which prevent and/or inhibit TNF receptor signalling.

BRIEF DESCRIPTION OF THE DRAWINGS

FIGS. 7A-7F are a set of six graphs showing the serum cA2 concentration in each RA patient receiving cA2 treatment (1 mg/kg, 3 mg/kg or 10 mg/kg) with or without methotrexate, plotted over time. Data plotted are the serum cA2 concentrations obtained just before the administration of cA2 at weeks 2, 6, 10 and 14 and then at weeks 18 and 26. The scales for the serum cA2 concentration are condensed with higher doses of cA2.

DETAILED DESCRIPTION OF THE INVENTION

Figure 1A:
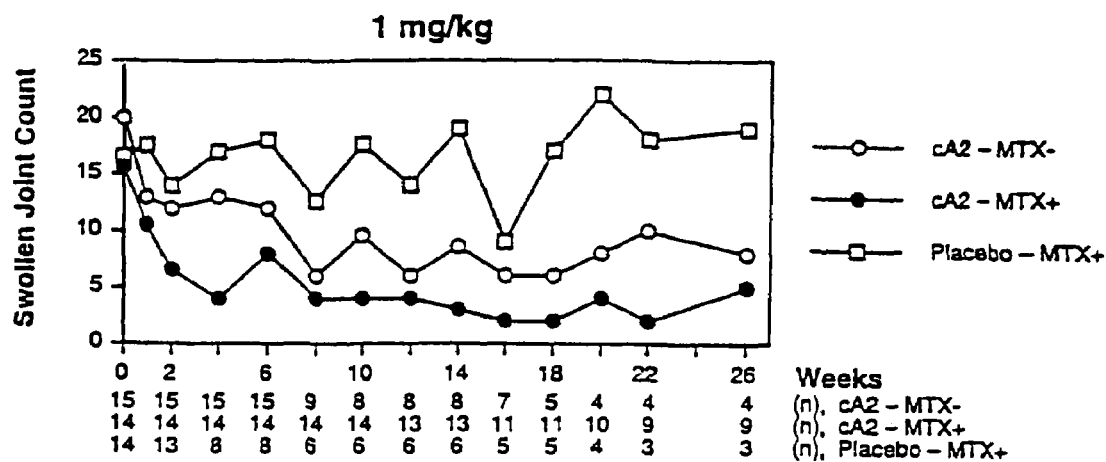
FIGS. 1A-1C are a set of three graphs showing the results over time for swollen joint count in rheumatoid arthritis (RA) patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate (MTX−); black circle=+methotrexate (MTX+); square=placebo.
Figure 1B:
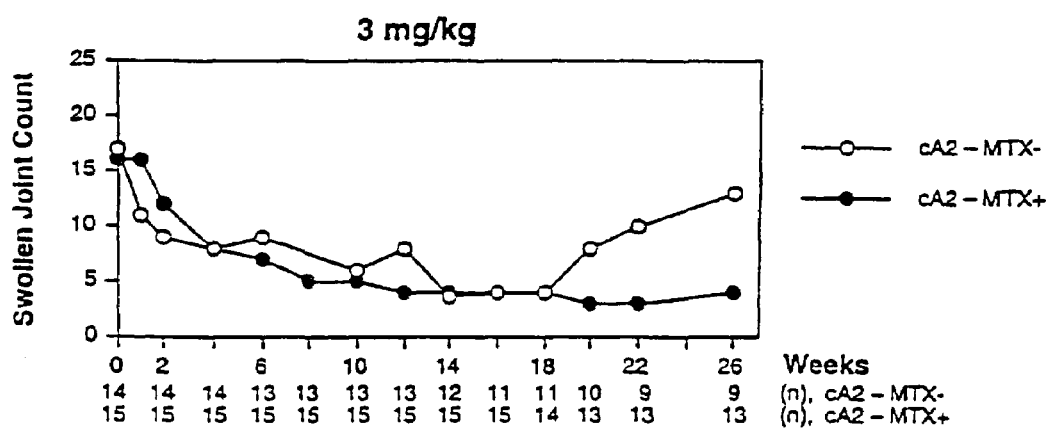
Figure 1C:
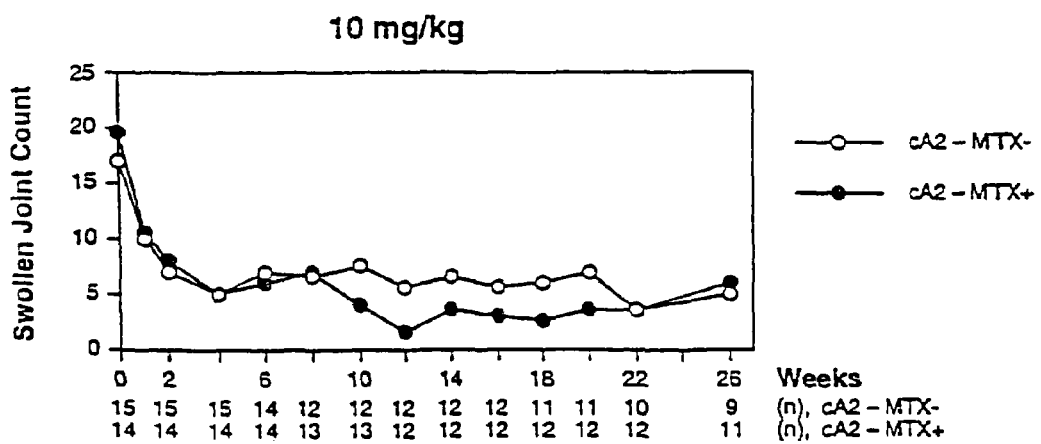
Figure 2A:
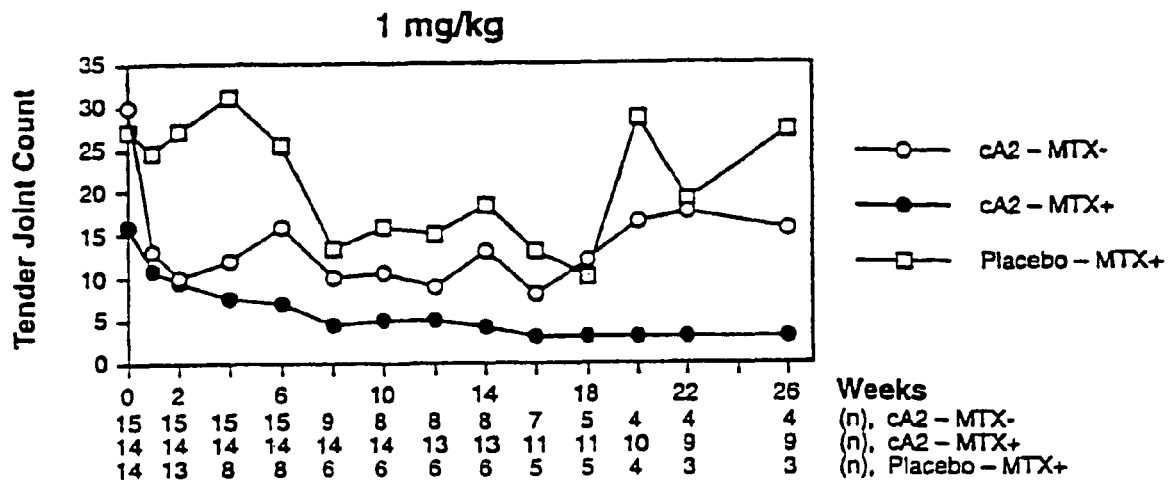
FIGS. 2A-2C are a set of three graphs showing the results over time for tender joint count in RA patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate; black circle=+methotrexate; square=placebo.
Figure 2B:
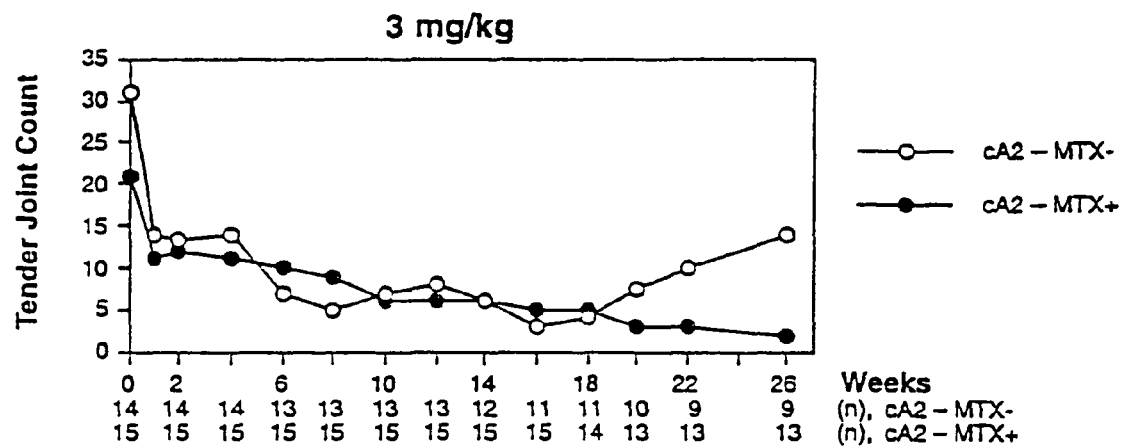
Figure 2C:
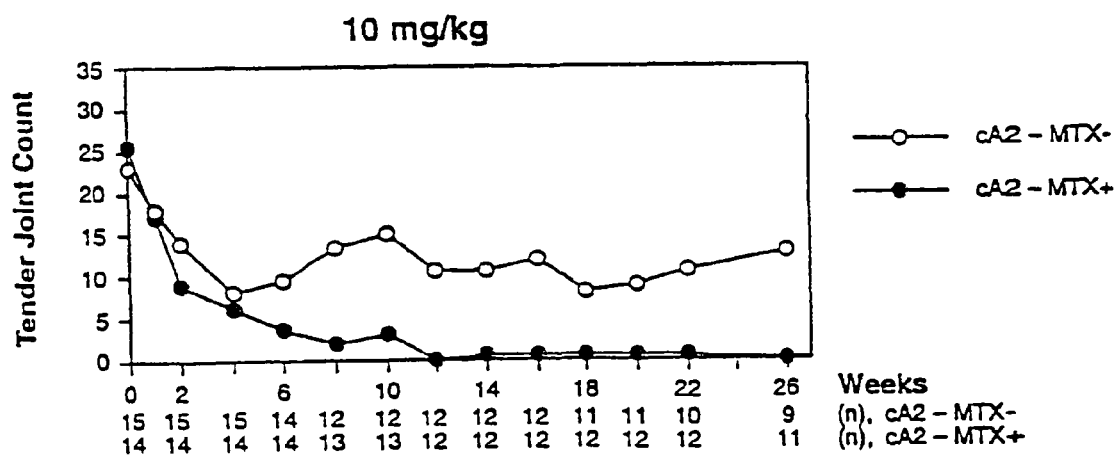
Figure 3A:
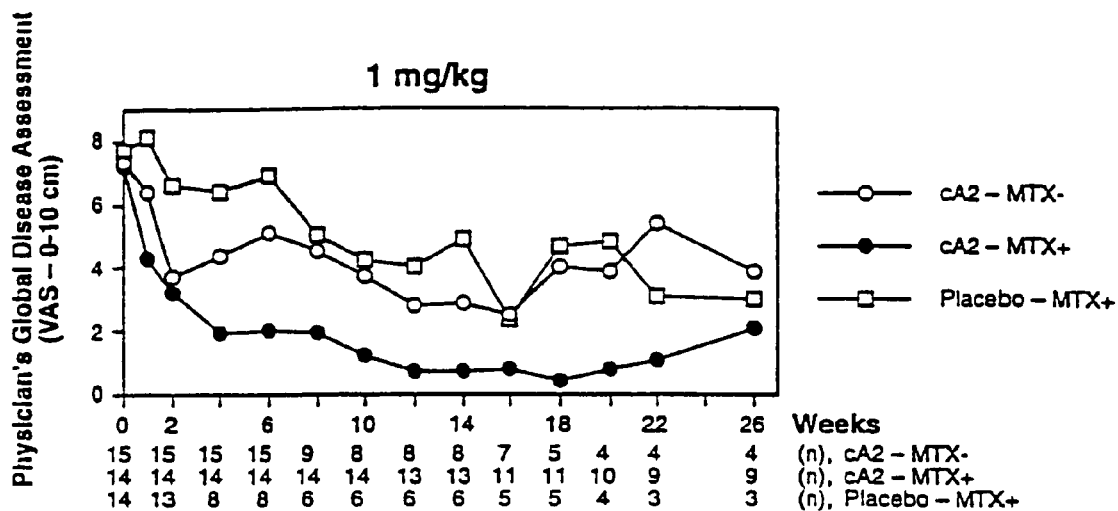
FIGS. 3A-3C are a set of three graphs showing the results over time for the Physician's Global Disease Assessment in RA patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate; black circle=+methotrexate; square=placebo.
Figure 3B:
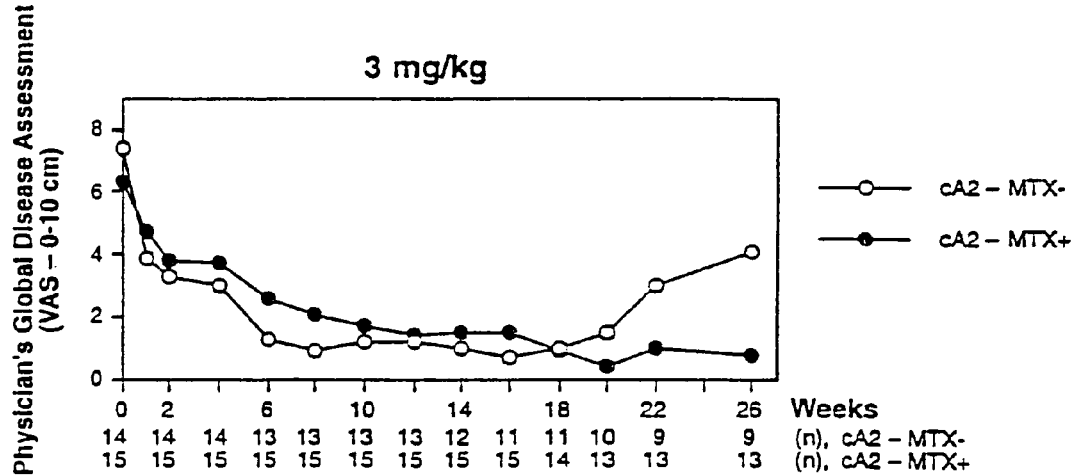
Figure 3C:
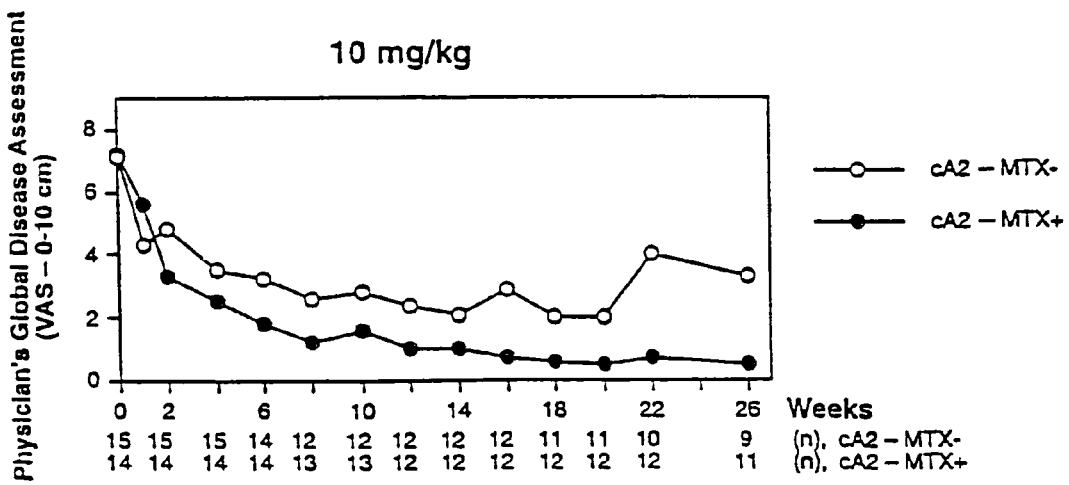
Figure 4A:
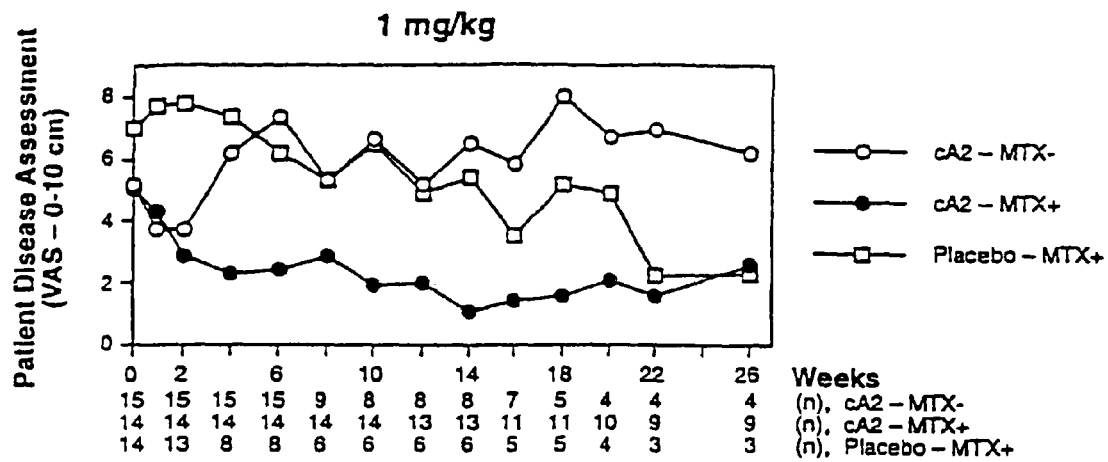
FIGS. 4A-4C are a set of three graphs showing the results over time for the Patient Disease Assessment in RA patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate; black circle=+methotrexate; square=placebo.
Figure 4B:
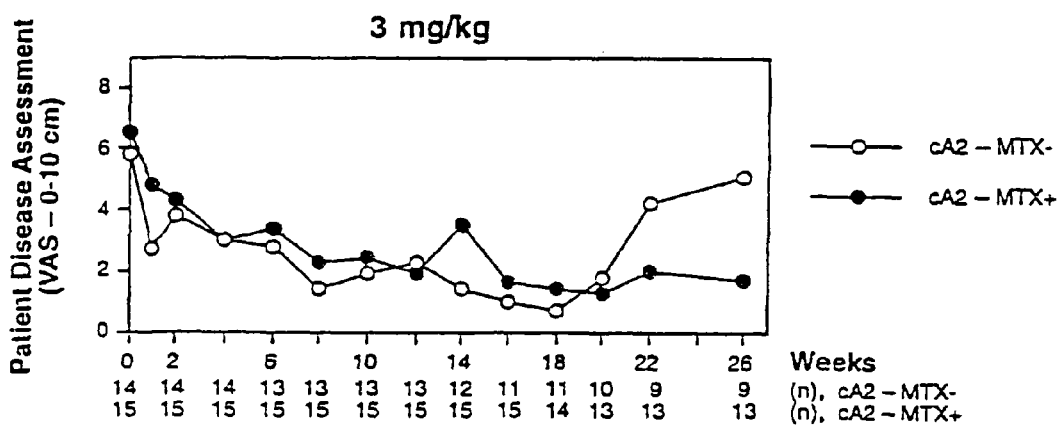
Figure 4C:
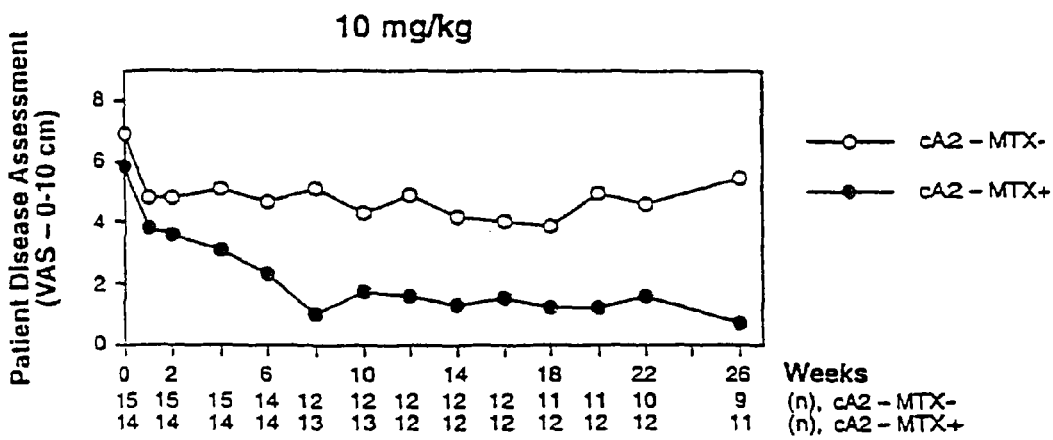

The present invention relates to the discovery that tumor necrosis factor antagonists can be administered to patients suffering from a TNF-mediated disease as adjunctive and/or concomitant therapy to methotrexate therapy, with good to excellent alleviation of the signs and symptoms of the disease. The present invention also relates to the discovery that tumor necrosis factor antagonists can be administered to patients suffering from a TNF-mediated disease in multiple doses and as adjunctive and/or concomitant therapy to methotrexate therapy, with a significant improvement in duration of clinical response.

As a result of applicants' invention, a method is provided herein for treating and/or preventing a TNF-mediated disease in an individual, comprising co-administering methotrexate and a tumor necrosis factor antagonist to the individual in therapeutically effective amounts. The TNF antagonist and methotrexate can be administered simultaneously or sequentially. The TNF antagonist and methotrexate can each be administered in single or multiple doses. Multiple TNF antagonists can be co-administered with methotrexate. Other therapeutic regimens and agents can be used in combination with the therapeutic co-administration of TNF antagonists and methotrexate or other drugs that suppress the immune system.

A method is also provided herein for treating and/or preventing recurrence of a TNF-mediated disease in an individual comprising co-administering methotrexate and a TNF antagonist to the individual in therapeutically effective amounts.

As used herein, a "TNF-mediated disease" refers to a TNF related pathology or disease. TNF related pathologies or diseases include, but are not limited to, the following:

(A) acute and chronic immune and autoimmune pathologies, such as, but not limited to, rheumatoid arthritis (RA), juvenile chronic arthritis (JCA), thyroiditis, graft versus host disease (GVHD), scleroderma, diabetes mellitus, Graves' disease, allergy, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation;

(B) infections, including, but not limited to, sepsis syndrome, cachexia, circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) (including symptoms of cachexia, autoimmune disorders, AIDS dementia complex and infections);

(C) inflammatory diseases, such as chronic inflammatory pathologies, including chronic inflammatory pathologies such as, but not limited to, sarcoidosis, chronic inflammatory bowel disease, ulcerative colitis, and Crohn's pathology or disease; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schönlein purpura, giant cell arthritis and microscopic vasculitis of the kidneys; chronic active hepatitis; Sjögren's syndrome; spondyloarthropathies, such as ankylosing spondylitis, psoriatic arthritis and spondylitis, enteropathic arthritis and spondylitis, reactive arthritis and arthritis associated with inflammatory bowel disease; and uveitis;

(D) neurodegenerative diseases, including, but not limited to, demyelinating diseases, such as multiple sclerosis and acute transverse myelitis; myasthenia gravis; extrapyramidal and cerebellar disorders, such as lesions of the corticospinal system; disorders of the basal ganglia or cerebellar disorders; hyperkinetic movement disorders, such as Huntington's chorea and senile chorea; drug-induced movement disorders, such as those induced by drugs which block central nervous system (CNS) dopamine receptors; hypokinetic movement disorders, such as Parkinson's disease; progressive supranuclear palsy; cerebellar and spinocerebellar disorders, such as astructual lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and MachadoJoseph)); and systemic disorders (Refsum's disease, abetalipoproteinemia, ataxia, telangiectasia, and mitochondrial multisystem disorder); disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's syndrome in middle age; diffuse Lewy body disease; senile dementia of Lewy body type; Wernicke-Korsakoff syndrome; chronic alcoholism; primary biliary cirrhosis; cryptogenic fibrosing alveolitis and other fibrotic lung diseases; hemolytic anemia; Creutzfeldt-Jakob disease; subacute sclerosing panencephalitis, Hallervorden-Spatz disease; and dementia pugilistica, or any subset thereof;

(E) malignant pathologies involving TNF-secreting tumors or other malignancies involving TNF, such as, but not limited to, leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or Mycosis fungoides));

(F) cachectic syndromes and other pathologies and diseases involving excess TNF, such as, but not limited to, cachexia of cancer, parasitic disease and heart failure; and (G) alcohol-induced hepatitis and other forms of chronic hepatitis.

See, e.g., Berkow et al., Eds., *The Merck Manual,* 16th edition, chapter 11, pp. 1380-1529, Merck and Co., Rahway; N.J., 1992, incorporated herein by reference.

The terms "recurrence", "flare-up" or "relapse" are defined to encompass the reappearance of one or more symptoms of the disease state. For example, in the case of rheumatoid arthritis, a reoccurrence can include the experience of one or more of swollen joints, morning stiffness or joint tenderness.

In one embodiment, the invention relates to a method of treating and/or preventing rheumatoid arthritis in an individual comprising co-administering methotrexate and a TNF antagonist to the individual in therapeutically effective amounts.

In a second embodiment, the invention relates to a method for treating and/or preventing Crohn's disease in an individual comprising co-administering a methotrexate and a TNF antagonist to the individual in therapeutically effective amounts.

In a third embodiment, the invention relates to a method for treating and/or preventing an acute or chronic immune disease associated with an allogenic transplantation in an individual comprising co-administering methotrexate and a TNF antagonist to the individual in therapeutically effective amounts. As used herein, a "transplantation" includes organ, tissue or cell transplantation, such as renal transplantation, cardiac transplantation, bone marrow transplantation, liver transplantation, pancreatic transplantation, small intestine transplantation, skin transplantation and lung transplantation.

The benefits of combination therapy with methotrexate and TNF antagonists include high clinical response rates for significantly longer durations in comparison with that obtained with treatment with each therapeutic modality separately. In addition, methotrexate significantly reduces immunogenicity of anti-TNF antibodies, thus permitting administration of multiple dosages of anti-TNF antibodies with enhanced safety. The results described herein suggest that methotrexate can be used to reduce immunogenicity of other antibodies or proteins. Based on the results described herein, methotrexate can be used in other forms of antibody therapy, such as anti-IL-2 antibody therapy. This method is particularly pertinent in therapies other than anti-CD4 antibody therapy.

In a further embodiment, the invention relates to compositions comprising methotrexate and a TNF antagonist. The compositions of the present invention are useful for treating a subject having a pathology or condition associated with abnormal levels of a substance reactive with a TNF antagonist, in particular TNF in excess of, or less than, levels present in a normal healthy subject, where such excess or diminished levels occur in a systemic, localized or particular tissue type or location in the body. Such tissue types can include, but are not limited to, blood, lymph, central nervous system (CNS), liver, kidney, spleen, heart muscle or blood vessels, brain or spinal cord white matter or grey matter, cartilage, ligaments, tendons, lung, pancreas, ovary, testes, prostate. Increased or decreased TNF concentrations relative to normal levels can also be localized to specific regions or cells in the body, such as joints, nerve blood vessel junctions, bones, specific tendons or ligaments, or sites of infection, such as bacterial or viral infections.

Tumor Necrosis Factor Antagonists

As used herein, a "tumor necrosis factor antagonist" decreases, blocks, inhibits, abrogates or interferes with TNF activity in vivo. For example, a suitable TNF antagonist can bind TNF and includes anti-TNF antibodies and receptor molecules which bind specifically to TNF. A suitable TNF antagonist can also prevent or inhibit TNF synthesis and/or TNF release and includes compounds such as thalidomide, tenidap, and phosphodiesterase inhibitors, such as, but not limited to, pentoxifylline and rolipram. A suitable TNF antagonist that can prevent or inhibit TNF synthesis and/or TNF release also includes A2b adenosine receptor enhancers and A2b adenosine receptor agonists (e.g., 5'-(N-cyclopropyl)-carboxamidoadenosine, 5'-N-ethylcarboxamidoadenosine, cyclohexyladenosine and R—$N^6$-phenyl-2-propyladenosine). See, for example, Jacobson (GB 2 289 218 A), the teachings of which are entirely incorporated herein by reference. A suitable TNF antagonist can also prevent or inhibit TNF receptor signalling.

Anti-TNF Antibodies

As used herein, an "anti-tumor necrosis factor antibody" decreases, blocks, inhibits, abrogates or interferes with TNF activity in vivo. Anti-TNF antibodies useful in the methods and compositions of the present invention include monoclonal, chimeric, humanized, resurfaced and recombinant antibodies and fragments thereof which are characterized by high affinity binding to TNF and low toxicity (including human anti-murine antibody (HAMA) and/or human anti-chimeric antibody (HACA) response). In particular, an antibody where the individual components, such as the variable region, constant region and framework, individually and/or collectively possess low immunogenicity is useful in the present invention. The antibodies which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

An example of a high affinity monoclonal antibody useful in the methods and compositions of the present invention is murine monoclonal antibody (mAb) A2 and antibodies which will competitively inhibit in vivo the binding to human TNFα of anti-TNFα murine mAb A2 or an antibody having substantially the same specific binding characteristics, as well as fragments and regions thereof. Murine monoclonal antibody A2 and chimeric derivatives thereof, such as cA2, are described in U.S. application Ser. No. 08/192,093 (filed Feb. 4, 1994), U.S. application Ser. No. 08/192,102 (filed Feb. 4, 1994; now U.S. Pat. No. 5,656,272), U.S. application Ser. No. 08/192,861 (filed Feb. 4, 1994; now U.S. Pat. No. 5,919,452), U.S. application Ser. No. 08/324,799 (filed Oct. 18, 1994; now U.S. Pat. No. 5,698,195), and Le, J. et al., International Publication No. WO 92/16553 (published Oct. 1, 1992), which references are entirely incorporated herein by reference. A second example of a high affinity monoclonal antibody useful in the methods and compositions of the present invention is murine mAb 195 and antibodies which will competitively inhibit in vivo the binding to human TNFα of anti-TNFα murine 195 or an antibody having substantially the same specific binding characteristics, as well as fragments and regions thereof. Other high affinity monoclonal antibodies useful in the methods and compositions of the present invention include murine mAb 114 and murine mAb 199 and antibodies which will competitively inhibit in vivo the binding to human TNFα of anti-TNFα murine mAb 114 or mAb 199 or an antibody having substantially the same specific binding characteristics of mAb 114 or mAb 199, as well as fragments and regions thereof. Murine monoclonal antibodies 114, 195 and 199 and the method for producing them are described by Möller, A. et al. (*Cytokine* 2(3):162-169 (1990)), the teachings of which are entirely incorporated herein by reference. Preferred methods for determining mAb specificity and affinity by competitive inhibition can be found in Harlow, et al., *Antibodies: A Laboratory Manual*, Cold Spring Harbor Laboratory Press, Cold Spring Harbor, N.Y. (1988); Colligan et al., eds., *Current Protocols in Immunology*, Greene Publishing Assoc. and Wiley Interscience, New York (1992, 1993); Kozbor et al., *Immunol. Today* 4:72-79 (1983); Ausubel et al., eds., *Current Protocols in Molecular Biology*, Wiley Interscience, New York (1987, 1992, 1993); and Muller, *Meth. Enzymol.* 92:589-601 (1983), which references are entirely incorporated herein by reference.

Additional examples of monoclonal anti-TNF antibodies that can be used in the present invention are described in the art (see, e.g., U.S. application Ser. No. 07/943,852 (filed Sep. 11, 1992); Rathjen et al., International Publication No. WO 91/02078 (published Feb. 21, 1991); Rubin et al., EPO Patent Publication 0218868 (published Apr. 22, 1987); Yone et al., EPO Patent Publication No. 0288088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); Hirai, et al., *J. Immunol. Meth.* 96:57-62 (1.987); Moller, et al., *Cytokine* 2:162-169 (1990), which references are entirely incorporated herein by reference).

Chimeric antibodies are immunoglobulin molecules characterized by two or more segments or portions derived from different animal species. Generally, the variable region of the chimeric antibody is derived from a non-human mammalian antibody, such as a murine mAb, and the immunoglobulin constant region is derived from a human immunoglobulin molecule. Preferably, a variable region with low immunogenicity is selected and combined with a human constant region which also has low immunogenicity, the combination also preferably having low immunogenicity. "Low" immunogenicity is defined herein as raising significant HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344:1125-1127 (1994), incorporated herein by reference).

As used herein, the term "chimeric antibody" includes monovalent, divalent or polyvalent immunoglobulins. A monovalent chimeric antibody is a dimer (HL)) formed by a chimeric H chain associated through disulfide bridges with a chimeric L chain. A divalent chimeric antibody is a tetramer (H2L2) formed by two HL dimers associated through at least one disulfide bridge. A polyvalent chimeric antibody can also be produced, for example, by employing a CH region that aggregates (e.g., from an IgM H chain, or μ chain).

Antibodies comprise individual heavy (H) and/or light (L) immunoglobulin chains. A chimeric H chain comprises an antigen binding region derived from the H chain of a non-human antibody specific for TNF, which is linked to at least a portion of a human H chain C region (CH), such as CH1 or CH2. A chimeric L chain comprises an antigen binding region derived from the L chain of a non-human antibody specific for TNF, linked to at least a portion of a human L chain C region (CL).

Chimeric antibodies and methods for their production have been described in the art (Morrison et al., *Proc. Natl. Acad. Sci. USA* 81:6851-6855 (1984); Boulianne et al., *Nature* 312: 643-646 (1984); Neuberger et al., *Nature* 314:268-270 (1985); Taniguchi et al., European Patent Application No. 171496 (published Feb. 19, 1985); Morrison et al., European Patent Application No. 173494 (published Mar. 5, 1986); Neuberger et al., PCT Application No. WO 86/01533, (published Mar. 13, 1986); Kudo et al., European Patent Application No. 184187 (published Jun. 11, 1986); Morrison et al., European Patent Application No. 173494 (published Mar. 5, 1986); Sahagan et al., *J. Immunol.* 137:1066-1074 (1986); Robinson et al., International Publication No. PCT/US86/ 02269 (published May 7, 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); and Harlow and Lane, *Antibodies: A Laboratory*

*Manual*, Cold Spring Harbor Laboratory, New York, 1988). These references are entirely incorporated herein by reference.

The anti-TNF chimeric antibody can comprise, for example, two light chains and two heavy chains, each of the chains comprising at least part of a human constant region and at least part of a variable (V) region of non-human origin having specificity to human TNF, said antibody binding with high affinity to an inhibiting and/or neutralizing epitope of human TNF, such as the antibody cA2. The antibody also includes a fragment or a derivative of such an antibody, such as one or more portions of the antibody chain, such as the heavy chain constant or variable regions, or the light chain constant or variable regions.

Humanizing and resurfacing the antibody can further reduce the immunogenicity of the antibody. See, for example, Winter (U.S. Pat. No. 5,225,539 and EP 239,400 B1), Padlan et al. (EP 519,596 A1) and Pedersen et al. (EP 592,106 A1). These references are incorporated herein by reference.

Preferred antibodies useful in the methods and compositions of the present invention are high affinity human-murine chimeric anti-TNF antibodies, and fragments or regions thereof, that have potent inhibiting and/or neutralizing activity in vivo against human TNFα. Such antibodies and chimeric antibodies can include those generated by immunization using purified recombinant TNFα or peptide fragments thereof comprising one or more epitopes.

An example of such a chimeric antibody is cA2 and antibodies which will competitively inhibit in vivo the binding to human TNFα of anti-TNFα murine mAb A2, chimeric mAb cA2, or an antibody having substantially the same specific binding characteristics, as well as fragments and regions thereof. Chimeric mAb cA2 has been described, for example, in U.S. application Ser. No. 08/192,093 (filed Feb. 4, 1994), U.S. application Ser. No. 08/192,102 (filed Feb. 4, 1994; now U.S. Pat. No. 5,656,272), U.S. application Ser. No. 08/192,861 (filed Feb. 4, 1994; now U.S. Pat. No. 5,919,452), and U.S. application Ser. No. 08/324,799 (filed Oct. 18, 1994; now U.S. Pat. No. 5,698,195), and by Le, J. et al. (International Publication No. WO 92/16553 (published Oct. 1, 1992)); Knight, D. M. et al. (*Mol. Immunol.* 30:1443-1453 (1993)); and Siegel, S. A. et al. (*Cytokine* 7(1):15-25 (1995)). These references are entirely incorporated herein by reference.

Chimeric A2 anti-TNF consists of the antigen binding variable region of the high-affinity neutralizing mouse anti-human TNF IgG1 antibody, designated A2, and the constant regions of a human IgG1, kappa immunoglobulin. The human IgG1 Fc region improves allogeneic antibody effector function, increases the circulating serum half-life and decreases the immunogenicity of the antibody. The avidity and epitope specificity of the chimeric A2 is derived from the variable region of the murine A2. Chimeric A2 neutralizes the cytotoxic effect of both natural and recombinant human TNF in a dose dependent manner. From binding assays of cA2 and recombinant human TNF, the affinity constant of cA2 was calculated to be $1.8 \times 10^9 M^{-1}$. Preferred methods for determining mAb specificity and affinity by competitive inhibition can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992, 1993); Kozbor et al., *Immunol. Today* 4:72-79 (1983); Ausubel et al., eds. *Current Protocols in Molecular Biology*, Wiley Interscience, New York (1987, 1992, 1993); and Muller, *Meth. Enzymol.* 92:589-601 (1983), which references are entirely incorporated herein by reference.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues. Generally, the antigen binding region will be of murine origin. In other embodiments, the antigen binding region can be derived from other animal species, such as sheep, rabbit, rat or hamster. Preferred sources for the DNA encoding such a non-human antibody include cell lines which produce antibody, preferably hybrid cell lines commonly known as hybridomas. In one embodiment, a preferred hybridoma is the A2 hybridoma cell line.

An "antigen" is a molecule or a portion of a molecule capable of being bound by an antibody which is additionally capable of inducing an animal to produce antibody capable of selectively binding to an epitope of that antigen. An antigen can have one or more than one epitope.

The term "epitope" is meant to refer to that portion of the antigen capable of being recognized by and bound by an antibody at one or more of the antibody's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule containing the epitope, in vivo or in vitro, more preferably in vivo, including binding of TNF to a TNF receptor. Epitopes of TNF have been identified within amino acids 1 to about 20, about 56 to about 77, about 108 to about 127 and about 138 to about 149. Preferably, the antibody binds to an epitope comprising at least about 5 amino acids of TNF within TNF residues from about 87 to about 107, about 59 to about 80 or a combination thereof. Generally, epitopes include at least about 5 amino acids and less than about 22 amino acids embracing or overlapping one or more of these regions.

For example, epitopes of TNF which are recognized by, and/or binds with anti-TNF activity, an antibody, and fragments, and variable regions thereof, include:

```
                                           (SEQ ID NO:1)
59-80:  Tyr-Ser-Gln-Val-Leu-Phe-Lys-Gly-Gln-Gly-

Cys-Pro-Ser-Thr-His-Val-Leu-Leu-Thr-His-Thr-Ile;
and/or (SEQ ID NO:2)
87-108: Tyr-Gln-Thr-Lys-Val-Asn-Leu-Leu-Ser-Ala- Ile-Lys-Ser-Pro-Cys-Gln-Arg-Glu-Thr-Pro-Glu-Gly.
```

The anti-TNF antibodies, and fragments, and variable regions thereof, that are recognized by, and/or binds with anti-TNF activity, these epitopes block the action of TNFα without binding to the putative receptor binding locus as presented by Eck and Sprang (*J. Biol. Chem.* 264(29): 17595-17605 (1989) (amino acids 11-13, 37-42, 49-57 and 155-157 of hTNFα). Rathjen et al., International Publication No. WO 91/02078 (published Feb. 21, 1991), incorporated herein by reference, discloses TNF ligands which can bind additional epitopes of TNF.

Antibody Production Using Hybridomas

The techniques to raise antibodies to small peptide sequences that recognize and bind to those sequences in the free or conjugated form or when presented as a native sequence in the context of a large protein are well known in the art. Such antibodies can be produced by hybridoma or recombinant techniques known in the art.

Murine antibodies which can be used in the preparation of the antibodies useful in the methods and compositions of the present invention have also been described in Rubin et al., EP 0218868 (published Apr. 22, 1987); Yone et al., EP 0288088 (published Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); Hirai, et al., *J. Immunol. Meth.* 96:57-62 (1987); Möller, et al., *Cytokine* 2:162-169 (1990).

The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incorporated entirely herein by reference.

The TNFα-specific murine mAb useful in the methods and compositions of the present invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In one embodiment, the antibody used in the methods and compositions of the present invention is a mAb which binds amino acids of an epitope of TNF recognized by A2, rA2 or cA2, produced by a hybridoma or by a recombinant host. In another embodiment, the antibody is a chimeric antibody which recognizes an epitope recognized by A2. In still another embodiment, the antibody is a chimeric antibody designated as chimeric A2 (cA2).

As examples of antibodies useful in the methods and compositions of the present invention, murine mAb A2 is produced by a cell line designated c134A.

"Derivatives" of the antibodies including fragments, regions or proteins encoded by truncated or modified genes to yield molecular species functionally resembling the immunoglobulin fragments are also useful in the methods and compositions of the present invention. The modifications include, but are not limited to, addition of genetic sequences coding for cytotoxic proteins such as plant and bacterial toxins. The fragments and derivatives can be produced from appropriate cells, as is known in the art. Alternatively, anti-TNF antibodies, fragments and regions can be bound to cytotoxic proteins or compounds in vitro, to provide cytotoxic anti-TNF antibodies which would selectively kill cells having TNF on their surface.

"Fragments" of the antibodies include, for example, Fab, Fab', F(ab')$_2$ and Fv. These fragments lack the Fc fragment of intact antibody, clear more rapidly from the circulation, and can have less non-specific tissue binding than an intact antibody (Wahl et al., *J. Nucl. Med.* 24:316-325 (1983)). These fragments are produced from intact antibodies using methods well known in the art, for example by proteolytic cleavage with enzymes such as papain (to produce Fab fragments) or pepsin (to produce F(ab')$_2$ fragments).

Recombinant Expression of Anti-TNF Antibodies

Recombinant and/or chimeric murine-human or human-human antibodies that inhibit TNF can be produced using known techniques based on the teachings provided in U.S. application Ser. No. 08/192,093 (filed Feb. 4, 1994), U.S. application Ser. No. 08/192,102 (filed Feb. 4, 1994; now U.S. Pat. No. 5,656,272), U.S. application Ser. No. 08/192,861 (filed Feb. 4, 1994; now U.S. Pat. No. 5,919,452), U.S. application Ser. No. 08/324,799 (filed on Oct. 18, 1994; now U.S. Pat. No. 5,698,195) and Le, J. et al., International Publication No. WO 92/16553 (published Oct. 1, 1992), which references are entirely incorporated herein by reference. See, e.g., Ausubel et al., eds. *Current Protocols in Molecular Biology*, Wiley Interscience, New York (1987, 1992, 1993); and Sambrook et al. *Molecular Cloning: A Laboratory Manual*, Cold Spring Harbor Laboratory Press, New York (1989), the contents of which are entirely incorporated herein by reference. See also, e.g., Knight, D. M., et al., *Mol. Immunol* 30:1443-1453 (1993); and Siegel, S. A., et al., *Cytokine* 7(1):15-25 (1995), the contents of which are entirely incorporated herein by reference.

The DNA encoding an anti-TNF antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (*Proc. Natl. Acad. Sci., USA* 84:3439 (1987) and *J. Immunology* 139:3521 (1987)), which references are entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems. An example of such a preparation is set forth below.

Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-TNF antibody or fragment. Such "codon usage rules" are disclosed by Lathe, et al., *J. Mol. Biol.* 183:1-12 (1985). Using the "codon usage rules" of Lathe, a single oligonucleotide, or a set of oligonucleotides, that contains a theoretical "most probable" nucleotide sequence capable of encoding anti-TNF variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-TNF antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-TNF gene (Sambrook et al., infra).

A suitable oligonucleotide, or set of oligonucleotides, which is capable of encoding a fragment of the variable or constant anti-TNF region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-TNF antibodies or variable or constant regions thereof. Single stranded oligonucleotide molecules complementary to the "most probable" variable or constant anti-TNF region peptide coding sequences can be synthesized using procedures which are well known to those of ordinary skill in the art (Belagaje, et al., *J. Biol. Chem.* 254:5765-5780 (1979); Maniatis, et al., *In: Molecular Mechanisms in the Control of Gene Expression*, Nierlich, et al., eds., Acad. Press, New York (1976); Wu, et al., *Prog. Nucl. Acid Res. Molec. Biol.* 21:101-141 (1978); Khorana, *Science* 203:614-625 (1979)). Additionally, DNA synthesis can be achieved through the use of automated synthesizers. Techniques of nucleic acid hybridization are disclosed by Sambrook et al., *Molecular Cloning: A Laboratory Manual*, Cold Spring Harbor Laboratory Press, New York (1989); and by Haynes, et al., in: *Nucleic Acid Hybridization, A Practical Approach*, IRL Press, Washington, D.C. (1985), which references are entirely incorporated herein by reference. Techniques such as, or similar to, those described above have successfully enabled the cloning of genes for human aldehyde dehydrogenases (Hsu, et al., *Proc. Natl. Acad. Sci. USA* 82:3771-3775 (1985)), fibronectin (Suzuki, et al., *Bur. Mol. Biol. Organ. J.* 4:2519-2524 (1985)), the human estrogen receptor gene (Walter, et al., *Proc. Natl. Acad. Sci. USA* 82:7889-7893 (1985)), tissue-type plasminogen activator (Pennica, et al., *Nature* 301:214-221 (1983)) and human placental alkaline phosphatase complementary DNA (Keun, et al., *Proc. Natl. Acad. Sci. USA* 82:8715-8719 (1985)).

In an alternative way of cloning a polynucleotide encoding an anti-TNF variable or constant region, a library of expression vectors is prepared by cloning DNA or, more preferably, cDNA (from a cell capable of expressing an anti-TNF antibody or variable or constant region) into an expression vector. The library is then screened for members capable of expressing a protein which competitively inhibits the binding of an anti-TNF antibody, such as A2 or cA2, and which has a nucleotide sequence that is capable of encoding polypeptides that have the same amino acid sequence as anti-TNF antibodies or fragments thereof. In this embodiment, DNA, or more preferably cDNA, is extracted and purified from a cell which is capable of expressing an anti-TNF antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11:591-595 (1993); Marks et al., *Bio/Technology* 11:1145-1149 (October 1993). Once nucleic acid encoding such variable or constant anti-TNF regions is isolated, the nucleic acid can be appropriately expressed in a host cell, along with other constant or variable heavy or light chain encoding nucleic acid, in order to provide recombinant monoclonal antibodies that bind TNF with inhibitory activity. Such antibodies preferably include a murine or human anti-TNF variable region which contains a framework residue having complementarity determining residues which are responsible for antigen binding.

Human genes which encode the constant (C) regions of the chimeric antibodies, fragments and regions of the present invention can be derived from a human fetal liver library, by known methods. Human C region genes can be derived from any human cell including those which express and produce human immunoglobulins. The human CH region can be derived from any of the known classes or isotypes of human H chains, including gamma, $\mu$, $\alpha$, $\delta$ or $\epsilon$, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1), gamma 3 (IgG3), gamma 4 (IgG4), or $\mu$ (IgM). The human CL region can be derived from either human L chain isotype, kappa or lambda.

Genes encoding human immunoglobulin C regions are obtained from human cells by standard cloning techniques (Sambrook, et al. (*Molecular Cloning: A Laboratory Manual*, 2nd Edition, Cold Spring Harbor Press, Cold Spring Harbor, N.Y. (1989) and Ausubel et al., eds., *Current Protocols in Molecular Biology*, Wiley Interscience, New York (1987-1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH1 domain and hinge region of the H chain, followed by a translational stop codon to yield the truncated molecule.

Generally, the murine, human and chimeric antibodies, fragments and regions are produced by cloning DNA segments encoding the H and L chain antigen-binding regions of a TNF-specific antibody, and joining these DNA segments to DNA segments encoding CH and CL regions, respectively, to produce murine, human or chimeric immunoglobulin-encoding genes. Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions and the method of producing a chimeric antibody can involve several steps, outlined below:

1. Isolation of messenger RNA (mRNA) from the cell line producing an anti-TNF antibody and from optional additional antibodies supplying heavy and light constant regions; cloning and cDNA production therefrom;
2. Preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;
3. Construction of complete H or L chain coding sequences by linkage of the cloned specific V region gene segments to cloned C region gene, as described above;
4. Expression and production of L and H chains in selected hosts, including prokaryotic and eukaryotic cells to provide murine-murine, human-murine, human-human or human-murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C (Ck) region and the complete human gamma-1 C region (C gamma-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human C gamma-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human CH or CL chain sequence having appropriate restriction sites engineered so that any VH or VL chain sequence with appropriate cohesive ends can be easily inserted therein. Human CH or CL chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C, region; polyadenylation and transcription termination occur at native chromosomal sites downstream of the human coding regions.

A nucleic acid sequence encoding at least one anti-TNF antibody fragment may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, supra, Sambrook, supra, entirely incorporated herein by reference, and are well known in the art.

A nucleic acid molecule, such as DNA, is "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-TNF peptides or antibody fragments in recoverable amounts. The precise nature of the regulatory regions needed for gene expression may vary from organism to organism and is well known in the analogous art. See, e.g., Sambrook et al., *Molecular Cloning: A Laboratory Manual*, Cold Spring Harbor Laboratory Press, New York (1989); and Ausubel, eds., *Current Protocols in Molecular Biology*, Wiley Interscience, New York (1987, 1993).

Many vector systems are available for the expression of cloned anti-TNF peptide H and L chain genes in mammalian cells (see Glover, ed., *DNA Cloning, Vol. II*, pp. 143-238, IRL Press, Washington, D.C., 1985). Different approaches can be followed to obtain complete H2L2 antibodies. It is possible to co-express H and L chains in the same cells to achieve intracellular association and linkage of H and L chains into complete tetrameric H2L2 antibodies. The co-expression can occur by using either the same or different plasmids in the same host. Genes for both H and L chains can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

Receptor Molecules

Receptor molecules (also referred to herein as soluble TNF receptors) useful in the methods and compositions of the present invention are those that bind TNF with high affinity (see, e.g., Feldmann et al., International Publication No. WO 92/07076 (published Apr. 30, 1992), incorporated herein by reference) and possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof, are also useful in the present invention. Truncated forms of the TNF receptors, comprising the ECD, have been detected in urine and serum as 30 kDa and 40 kDa TNF inhibitory binding proteins (Engelmann, H. et al., *J. Biol. Chem.* 265:1531-1536 (1990)). TNF receptor multimeric molecules and TNF immunoreceptor fusion molecules, and derivatives and fragments or portions thereof, are additional examples of receptor molecules which are useful in the methods and compositions of the present invention. The receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers. The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods and compositions of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent. An example of such a TNF immunoreceptor fusion molecule is TNF receptor/IgG fusion protein.

TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al., *Cytokine* 6(6):616-623 (1994); Baker et al., *Eur. J. Immunol.* 24:2040-2048 (1994); Beutler et al., U.S. Pat. No. 5,447,851; and U.S. application Ser. No. 08/442,133 (filed May 16, 1995)). These references are entirely incorporated herein by reference. Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

Derivatives, fragments, regions and functional portions of the receptor molecules functionally resemble the receptor molecules that can be used in the present invention (i.e., they bind TNF with high affinity and possess low immunogenicity). A functional equivalent or derivative of the receptor molecule refers to the portion of the receptor molecule, or the portion of the receptor molecule sequence which encodes the receptor molecule, that is of sufficient size and sequences to functionally resemble the receptor molecules that can be used in the present invention (i.e., bind TNF with high affinity and possess low immunogenicity). A functional equivalent of the receptor molecule also includes modified receptor molecules that functionally resemble the receptor molecules that can be used in the present invention (i.e., bind TNF with high affinity possess low immunogenicity). For example, a functional equivalent of the receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience, New York (1989).

Methotrexate

Presently available oral and intravenous formulations of methotrexate include RHEUMATREX® methotrexate dose pack (Lederle Laboratories, Wayne, N.J.); methotrexate tablets (Mylan Pharmaceuticals Inc., Morgantown, W. Va.; Roxane Laboratories, Inc., Columbus, Ohio); and methotrexate sodium tablets, for injection and injection (Immunex Corporation, Seattle, Wash.) and methotrexate LPF® sodium (methotrexate sodium injection) (Immunex Corporation, Seattle, Wash.). Methotrexate is also available from Pharmacochemie (Netherlands). Methotrexate prodrugs, homologs and/or analogs (e.g., folate antagonists) can also be used in the methods and compositions of the present invention. Alternatively, other immunosuppressive agents (or drugs that suppress the immune system) can be used in the methods and compositions of the present invention.

Administration

TNF antagonists, methotrexate and the compositions of the present invention can be administered to an individual in a variety of ways. The routes of administration include intradermal, transdermal (e.g., in slow release polymers), intramuscular, intraperitoneal, intravenous, subcutaneous, oral, topical, epidural, buccal, rectal, vaginal and intranasal routes. Any other therapeutically efficacious route of administration can be used, for example, infusion or bolus injection, absorption through epithelial or mucocutaneous linings, or by gene therapy wherein a DNA molecule encoding the therapeutic protein or peptide is administered to the patient, e.g., via a vector, which causes the protein or peptide to be expressed and secreted at therapeutic levels in vivo. In addition, the TNF antagonists, methotrexate and compositions of the present invention can be administered together with other components of biologically active agents, such as pharmaceutically acceptable surfactants (e.g., glycerides), excipients (e.g., lactose), carriers, diluents and vehicles. If desired, certain sweetening, flavoring and/or coloring agents can also be added.

The TNF antagonists and methotrexate can be administered prophylactically or therapeutically to an individual. TNF antagonists can be administered prior to, simultaneously with (in the same or different compositions) or sequentially with the administration of methotrexate. For example, TNF antagonists can be administered as adjunctive and/or concomitant therapy to methotrexate therapy.

For parenteral (e.g., intravenous, subcutaneous, intramuscular) administration, TNF antagonists, methotrexate and the compositions of the present invention can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

Suitable pharmaceutical carriers are described in Remington's Pharmaceutical Sciences, A. Osol, a standard reference text in this field of art.

For example, a parenteral composition suitable for administration by injection is prepared by dissolving 1.5% by weight of active ingredient in 0.9% sodium chloride solution.

TNF antagonists and methotrexate are administered in therapeutically effective amounts; the compositions of the present invention are administered in a therapeutically effective amount. As used herein, a "therapeutically effective amount" is such that administration of TNF antagonist and methotrexate, or administration of a composition of the present invention, results in inhibition of the biological activity of TNF relative to the biological activity of TNF when therapeutically effective amounts of antagonist and methotrexate are not administered, or relative to the biological activity of TNF when a therapeutically effective amount of the composition is not administered. A therapeutically effective amount is preferably an amount of TNF antagonist and methotrexate necessary to significantly reduce or eliminate signs and symptoms associated with a particular TNF-mediated disease. As used herein, a therapeutically effective amount is not necessarily an amount such that administration of the TNF antagonist alone, or administration of methotrexate alone, must necessarily result in inhibition of the biological activity of TNF.

Once a therapeutically effective amount has been administered, a maintenance amount of TNF antagonist alone, of methotrexate alone, or of a combination of TNF antagonist and methotrexate can be administered to the individual. A maintenance amount is the amount of TNF antagonist, methotrexate, or combination of TNF antagonist and methotrexate necessary to maintain the reduction or elimination of the signs and symptoms associated with a particular TNF-mediated disease achieved by the therapeutically effective dose. The maintenance amount can be administered in the form of a single dose, or a series or doses separated by intervals of days or weeks.

The dosage administered to an individual will vary depending upon a variety of factors, including the pharmacodynamic characteristics of the particular antagonists, and its mode and route of administration; size, age, sex, health, body weight and diet of the recipient; nature and extent of symptoms of the disease being treated, kind of concurrent treatment, frequency of treatment, and the effect desired. In vitro and in vivo methods of determining the inhibition of TNF in an individual are well known to those of skill in the art. Such in vitro assays can include a TNF cytotoxicity assay (e.g., the WEHI assay or a radioimmunoassay, ELISA). In vivo methods can include rodent lethality assays and/or primate pathology model systems (Mathison et al., *J. Clin. Invest.*, 81: 1925-1937 (1988); Beutler et al., *Science* 229:869-871 (1985); Tracey et al., *Nature* 330:662-664 (1987); Shimamoto et al., *Immunol. Lett.* 17:311-318 (1988); Silva et al., *J. Infect. Dis.* 162:421-427 (1990); Opal et al., *J. Infect. Dis.* 161:1148-1152 (1990); Hinshaw et al., *Circ. Shock* 30:279-292 (1990)).

TNF antagonist and methotrexate can each be administered in single or multiple doses depending upon factors such as nature and extent of symptoms, kind of concurrent treatment and the effect desired. Thus, other therapeutic regimens or agents (e.g., multiple drug regimens) can be used in combination with the therapeutic co-administration of TNF antagonists and methotrexate. In a particular embodiment, a TNF antagonist is administered in multiple doses. In another embodiment, methotrexate is administered in the form of a series of low doses separated by intervals of days or weeks. Adjustment and manipulation of established dosage ranges are well within the ability of those skilled in the art.

Usually a daily dosage of active ingredient can be about 0.01 to 100 milligrams per kilogram of body weight. Ordinarily 1 to 40 milligrams per kilogram per day given in divided doses 1 to 6 times a day or in sustained release form is effective to obtain desired results. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease. For example, second and subsequent administrations can be given between about one day to 30 weeks from the previous administration. Two, three, four or more total administrations can be delivered to the individual, as needed.

Dosage forms (composition) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

The present invention will now be illustrated by the following example, which is not intended to be limiting in any way.

EXAMPLES

Example 1

Clinical Treatment of Rheumatoid Arthritis by Multiple Infusions of an Anti-TNF Antibody with and without Methotrexate A randomized, double-blind, placebo controlled study was conducted to evaluate the safety and efficacy of a chimeric monoclonal anti-TNF antibody (cA2) following multiple infusions of 1, 3 or 10 mg/kg cA2, alone or in combination with methotrexate, compared to multiple infusions of placebo in combination with methotrexate, in the treatment of rheumatoid arthritis (RA) in patients.

Patients

One hundred one (101) patients at six European centers who had been using methotrexate for at least 6 months, had been on a stable dose of 7.5 mg/wk for at least 4 weeks, and had active disease (according to the criteria of the American College of Rheumatology) with erosive changes on X-rays of hands and feet, were enrolled in the trial. Active disease was defined by the presence of six or more swollen joints plus at least three of four secondary criteria (duration of morning stiffness $\geq 45$ minutes; $\geq 6$ tender or painful joints; erythrocyte sedimentation rate (ESR)$\geq 28$ mm/hour; C-reactive protein (CRP)$\geq 20$ mg/l.

In patients using corticosteroids ($\leq 7.5$ mg/day) or nonsteroidal anti-inflammatory drugs (NSAIDs), the doses had been stable for 4 weeks prior to screening. The dose of corticosteroids remained stable throughout trial participation. The dose of NSAID typically also remained stable throughout trial participation.

Study Infusions

The chimeric monoclonal anti-TNF antibody (cA2) was supplied as a sterile solution containing 5 mg cA2 per ml of 0.01 M phosphate-buffered saline in 0.15 M sodium chloride with 0.01% polysorbate 80, pH 7.2. The placebo vials contained 0.1% human serum albumin in the same buffer. Before use, the appropriate amount of cA2 or placebo was diluted to 300 ml in sterile saline by the pharmacist, and administered intravenously via a 0.2 µm in-line filter over 2 hours. The characteristics of the placebo and cA2 infusion bags were identical, and the investigators and patients did not know which infusion was being administered.

Assessments

Patients were randomized to one of seven treatment groups. The number of patients in each dose (or treatment)

group is indicated in Table 1. Each of the 101 patients received multiple infusions of either 0, 1, 3 or 10 mg/kg cA2. Infusions were to be administered at weeks 0, 2, 6, 10 and 14. Starting at week 0, the patients were receiving 7.5 mg/wk of methotrexate (Pharmacochemie, Netherlands) or 3 placebo tablets/week (Pharmacochemie, Netherlands). Patients were monitored for adverse events during infusions and regularly thereafter, by interviews, physical examination, and laboratory testing.

The six primary disease-activity assessments were chosen to allow analysis of the response in individual patients according to the Paulus index (Paulus, et al., *Arthritis Rheumatism* 33:477-484 (1990), the teachings of which are incorporated herein by reference). The assessments contributing to this index were the tender joint and swollen joint scores (60 and 58 joints, respectively, hips not assessed for swelling; graded 0-3), the duration of morning stiffness (minutes), the patient's and physician's assessment of disease severity (on a 5-point scale, ranging from 1 (symptom-free) to 5 (very severe), and erythrocyte sedimentation rate (ESR). Patients were considered to have responded if at least four of the six variables improved, defined as at least 20% improvement in the continuous variables, and at least two grades of improvement or improvement from grade 2 to 1 in the two disease-severity assessments (Paulus 20% response). Improvements of at least 50% in the continuous variables were also used (Paulus 50% response).

Other disease-activity assessments included the pain score (0-10 cm on a visual analogue scale (VAS)), an assessment of fatigue (0-10 cm VAS), and grip strength (0-300 mm Hg, mean of three measurements per hand by sphygmomanometer cuff).

The ESR was measured at each study site with a standard method (Westergen). C-reactive protein (CRP) was measured by rate nephelometry (Abbott fluorescent polarizing immunoassay). See also, Elliott et al., *Lancet* 344:1105-1110 (1994); Elliott et al., *Lancet* 344:1125-1127 (1994); and Elliott et al., *Arthritis Rheum.* 36(12):1681-1690 (1993), which references are entirely incorporated herein by reference.

Evaluations were performed at weeks 1, 2, 4, 6, 8, 10, 12, 14, 16, 18, 20, 22 and 26.

Results

The 101 patients were randomized to one of seven treatment (or dose) groups. The patients enrolled in each dose group were well matched for baseline demographics. Disease duration and swollen and tender joint counts at baseline were also well-balanced across the groups (Table 1). Table 1 also shows the maximum methotrexate dose administered within 6 months prior to randomization. Median maximum doses for each group ranged between 10 and 15 mg/week; there were no significant differences amongst the treatment groups (p=0.404).

TABLE 1

Baseline Disease Characteristics Joint Counts

| | Treatment Groups | | |
|---|---|---|---|
| | Placebo | 1 mg/kg cA2 | |
| | MTX+ | MTX+ | MTX− |
| Disease dur. (yrs) | | | |
| Pts evaluated | 14 | 14 | 15 |
| Mean ± SD | 7.6 ± 4.0 | 14.3 ± 12.1 | 7.6 ± 6.0 |
| Median | 6.9 | 11.4 | 5.2 |
| IQ range | (4.3, 11.5) | (3.3, 24.7) | (3.4, 9.0) |
| Range | (1.8, 14.2) | (0.7, 37.3) | (2.5, 21.3) |
| Number of Swollen joints, Paulus joint set (0-58) | | | |
| Pts evaluated | 14 | 14 | 15 |
| Mean ± SD | 18.1 ± 8.6 | 16.9 ± 7.8 | 21.2 ± 11.2 |
| Median | 16.5 | 15.5 | 20.0 |
| IQ range | (12.0, 25.0) | (10.0, 25.0) | (10.0, 33.0) |
| Range | (6.0, 38.0) | (6.0, 29.0) | (7.0, 40.0) |
| Number of tender joints, Paulus joint set (0-60) | | | |
| Pts evaluated | 14 | 14 | 15 |
| Mean ± SD | 31.5 ± 14.2 | 19.1 ± 10.7 | 29.9 ± 17.1 |
| Median | 27.0 | 16.0 | 30.0 |
| IQ range | (22.0, 44.0) | (13.0, 30.0) | (14.0, 45.0) |
| Range | (8.0, 52.0) | (2.0, 39.0) | (6.0, 58.0) |
| Max dose MTX prev. 6 mo (mg/kg) | | | |
| Pts evaluated | 14 | 14 | 15 |
| Mean ± SD | 13.8 ± 3.9 | 11.6 ± 3.5 | 12.8 ± 5.6 |
| Median | 15.0 | 11.3 | 12.5 |
| IQ range | (10.0, 15.0) | (10.0, 12.5) | (10.0, 15.0) |
| Range | (7.5, 20.0) | (7.5, 20.0) | (7.5, 30.0) |

TABLE 1-continued

Baseline Disease Characteristics Joint Counts

| | Treatment Groups 3 mg/kg cA2 | | Treatment Groups 10 mg/kg cA2 | | All | Treatment effect |
|---|---|---|---|---|---|---|
| | MTX+ | MTX− | MTX+ | MTX− | Patients | p-value |
| Disease dur. (yrs) | | | | | | |
| Pts evaluated | 15 | 14 | 14 | 15 | 101 | |
| Mean ± SD | 12.1 ± 9.0 | 7.8 ± 4.3 | 11.1 ± 7.4 | 9.7 ± 7.4 | 10.0 ± 7.8 | 0.634 |
| Median | 11.9 | 7.7 | 10.7 | 7.6 | 7.6 | |
| IQ range | (4.3, 16.4) | (4.6, 9.8) | (4.5, 15.5) | (4.9, 14.9) | (4.3, 14.4) | |
| Range | (0.7, 30.5) | (1.4, 17.4) | (1.4, 24.1) | (1.1, 24.3) | (0.7, 37.3) | |
| Number of Swollen joints, Paulus joint set (0-58) | | | | | | |
| Pts evaluated | 15 | 14 | 14 | 15 | 101 | |
| Mean ± SD | 17.7 ± 5.9 | 19.7 ± 9.9 | 21.1 ± 8.2 | 17.8 ± 8.7 | 18.9 ± 8.7 | 0.643 |
| Median | 16.0 | 17.0 | 19.5 | 17.0 | 18.0 | |
| IQ range | (13.0, 22.0) | (11.0, 32.0) | (15.0, 31.0) | (11.0, 21.0) | (12.0, 25.0) | |
| Range | (10.0, 29.0) | (8.0, 34.0) | (10.0, 34.0) | (7.0, 41.0) | (6.0, 41.0) | |
| Number of tender joints, Paulus joint set (0-60) | | | | | | |
| Pts evaluated | 15 | 14 | 14 | 15 | 101 | |
| Mean ± SD | 24.5 ± 14.4 | 31.2 ± 11.7 | 26.5 ± 12.0 | 26.2 ± 11.7 | 27.0 ± 13.5 | 0.135 |
| Median | 21.0 | 31.0 | 25.5 | 23.0 | 25.0 | |
| IQ range | (12.0, 32.0) | (23.0, 39.0) | (21.0, 38.0) | (17.0, 35.0) | (15.0, 38.0) | |
| Range | (10.0, 52.0) | (9.0, 52.0) | (8.0, 44.0) | (11.0, 48.0) | (2.0, 58.0) | |
| Max dose MTX prev. 6 mo (mg/kg) | | | | | | |
| Pts evaluated | 14 | 13 | 14 | 15 | 99 | |
| Mean ± SD | 11.6 ± 3.3 | 11.7 ± 4.8 | 12.7 ± 5.0 | 12.5 ± 3.0 | 12.4 ± 4.2 | 0.404 |
| Median | 10.0 | 10.0 | 10.0 | 12.5 | 12.5 | |
| IQ range | (10.0, 15.0) | (7.5, 12.5) | (10.0, 15.0) | (10.0, 15.0) | (10.0, 15.0) | |
| Range | (7.5, 17.5) | (7.5, 25.0) | (7.5, 25.0) | (7.5, 20.0) | (7.5, 30.0) | |

MTX = Methotrexate

The pre-specified primary analysis in this trial was the comparison of the total time of clinical response during the 26-week follow-up period. The results for the primary analysis are shown in Table 2. The duration of response of all cA2-treated groups, with the exception of the 1 mg/kg group not receiving methotrexate, was significantly improved ($p<0.001$) compared to the placebo group receiving methotrexate alone.

TABLE 2

Total Time of Response[a] Based On Paulus 20% Criteria

| | | | Treatment Groups | | | | |
|---|---|---|---|---|---|---|---|
| | Placebo | 1 mg/kg cA2 | | 3 mg/kg cA2 | | 10 mg/kg cA2 | Treatment |
| Total time of response in weeks | MTX+ (n = 14) | MTX+ (n = 14) | MTX− (n = 15) | MTX+ (n = 15) | MTX− (n = 14) | MTX+ (n = 13) | MTX− (n = 15) | effect p-value |
| Median | 0 | 16.6 | 2.6 | 16.5 | 17.2 | >23.1 | 10.4 | <0.001 |
| Minimum | 0 | 0 | 0 | 0 | 0 | 0 | 0 | |
| 25th percentile | 0.0 | 6.2 | 2.0 | 7.0 | 4.0 | 2.6 | 6.9 | |
| 75th percentile | 0.0 | 22.5 | 8.0 | >20.1 | 20.7 | >24.6 | >23.1 | |
| Maximum | >15.1 | >26.9 | 15.1 | >24.9 | >25.9 | >25.6 | >26.4 | |
| p-value vs. MTX alone | | <0.001 | 0.119 | <0.001 | <0.001 | <0.001 | <0.001 | |

[a]Patients were followed through 26 weeks following the initial infusion of cA2

The response rates at Paulus 20% are shown in Table 3. Drop-outs were considered as non-responders subsequent to their dropping out from the study. With the exception of the 1 mg/kg group not receiving methotrexate, all of the cA2-treated groups demonstrated clinical benefit through 14 weeks when the last dose of cA2 was received. Sustained clinical benefit was observed through 26 weeks (the last follow-up visit) in patients who received 3 or 10 mg/kg cA2 with methotrexate. Approximately one-half of the patients who received 3 mg/kg cA2 with methotrexate demonstrated continued clinical benefit at 26 weeks.

TABLE 3

Number of Patients Responding According To Paulus 20% Criteria At Each Evaluation Visit

| | Treatment Groups | | |
|---|---|---|---|
| | Placebo | 1 mg/kg cA2 | |
| | MTX+ (n = 14) | MTX+ (n = 14) | MTX− (n = 15) |
| Pts with any response | 21% (3/14) | 93% 13/14 | 80% 12/15 |
| p-value vs MTX alone | | <0.001 | 0.006 |
| Time post-infusion | | | |
| 1 Week | 0% (0/14) | 31% (4/13) | 53% (8/15) |
| 2 Weeks | 7% (1/14) | 64% (9/14) | 57% (8/14) |
| 4 Weeks[a] | 0% (0/14) | 79% 11/14 | 33% (5/15) |
| 6 Weeks | 0% (0/14) | 71% 10/14 | 27% (4/15) |
| 8 Weeks[a] | 14% (2/14) | 64% (9/14) | 20% (3/15) |
| 10 Weeks | 7% (1/14) | 71% 10/14 | 20% (3/15) |
| 12 Weeks[a] | 7% (1/14) | 57% (8/14) | 13% (2/15) |
| 14 Weeks | 0% (0/14) | 71% 10/14 | 7% (1/15) |
| 16 Weeks[a] | 14% (2/14) | 64% (9/14) | 7% (1/15) |
| 18 Weeks | 21% (3/14) | 50% (7/14) | 13% (2/15) |
| 20 Weeks | 7% (1/14) | 54% (7/13) | 13% (2/15) |
| 22 Weeks | 7% (1/14) | 46% (6/13) | 0% (0/15) |
| 26 Weeks[a] | 7% (1/14) | 21% (3/14) | 7% (1/15) |

| | Treatment Groups | | | | |
|---|---|---|---|---|---|
| | 3 mg/kg cA2 | | 10 mg/kg cA2 | | Treatment |
| | MTX+ (n = 15) | MTX− (n = 14) | MTX+ (n = 13) | MTX− (n = 15) | effect p-value |
| Pts with any response | 80% 12/15 | 79% 11/14 | 85% 11/13 | 80% 12/15 | <0.001 |
| p-value vs MTX alone | 0.002 | 0.002 | 0.001 | 0.004 | |
| Time post-infusion | | | | | |
| 1 Week | 27% (4/15) | 43% (6/14) | 31% (4/13) | 60% (9/15) | |
| 2 Weeks | 27% (4/15) | 43% (6/14) | 62% (8/13) | 53% (8/15) | |
| 4 Weeks[a] | 40% (6/15) | 64% (9/14) | 54% (7/13) | 53% (8/15) | 0.002 |
| 6 Weeks | 47% (7/15) | 50% (7/14) | 54% (7/13) | 47% (7/15) | |
| 8 Weeks[a] | 60% (9/15) | 71% 10/14 | 69% (9/13) | 40% (6/15) | 0.003 |
| 10 Weeks | 67% 10/15 | 64% (9/14) | 69% (9/13) | 53% (8/15) | |
| 12 Weeks[a] | 67% 10/15 | 64% (9/14) | 62% (8/13) | 60% (8/13) | <0.001 |
| 14 Weeks | 60% (9/15) | 57% (8/14) | 77% 10/13 | 53% (8/15) | |
| 16 Weeks[a] | 67% 10/15 | 64% (9/14) | 54% (7/13) | 67% 10/15 | <0.001 |
| 18 Weeks | 71% 10/14 | 69% (9/13) | 62% (8/13) | 57% (8/14) | |

TABLE 3-continued

Number of Patients Responding According To Paulus 20% Criteria At Each Evaluation Visit

| | | | | | |
|---|---|---|---|---|---|
| 20 Weeks | 53% (8/15) | 43% (6/14) | 54% (7/13) | 53% (8/15) | |
| 22 Weeks | 47% (7/15) | 36% (5/14) | 54% (7/13) | 33% (5/15) | |
| 26 Weeks[a] | 47% (7/15) | 21% (3/14) | 54% (7/13) | 33% (5/15) | 0.013 |

[a]Evaluation visits pre-specified for analysis.

TABLE 4

Number of Patients Responding According To Paulus 50% Criteria At Each Evaluation Visit

| | Treatment Groups | | |
|---|---|---|---|
| | Placebo | 1 mg/kg cA2 | |
| | MTX+ (n = 14) | MTX+ (n = 14) | MTX− (n = 15) |
| Pts with any response | 14.3% (2/14) | 85.7% (12/14) | 40.0% (6/15) |
| p-value vs MTX alone | | <0.001 | 0.079 |
| Time post-infusion | | | |
| 1 Week | 0.0% (0/14) | 7.7% (1/13) | 26.7% (4/15) |
| 2 Weeks | 0.0% (0/14) | 21.4% (3/14) | 28.6% (4/14) |
| 4 Weeks[a] | 0.0% (0/14) | 57.1% (8/14) | 13.3% (2/15) |
| 6 Weeks | 0.0% (0/14) | 57.1% (8/14) | 0.0% (0/15) |
| 8 Weeks[a] | 7.1% (1/14) | 50.0% (7/14) | 0.0% (0/15) |
| 10 Weeks | 0.0% (0/14) | 57.1% (8/14) | 0.0% (0/15) |
| 12 Weeks[a] | 7.1% (1/14) | 50.0% (7/14) | 6.7% (1/15) |
| 14 Weeks | 0.0% (0/14) | 57.1% (8/14) | 6.7% (1/15) |
| 16 Weeks[a] | 0.0% (0/14) | 64.3% (9/14) | 6.7% (1/15) |
| 18 Weeks | 7.1% (1/14) | 50.0% (7/14) | 6.7% (1/15) |
| 20 Weeks | 7.1% (1/14) | 53.8% (7/13) | 0.0% (0/15) |
| 22 Weeks | 0.0% (0/14) | 38.5% (5/13) | 0.0% (0/15) |
| 26 Weeks[a] | 0.0% (0/14) | 21.4% (3/14) | 6.7% (1/15) |

| | Treatment Groups | | | | Treatment |
|---|---|---|---|---|---|
| | 3 mg/kg cA2 | | 10 mg/kg cA2 | | |
| | MTX+ (n = 15) | MTX− (n = 14) | MTX+ (n = 13) | MTX− (n = 15) | effect p-value |
| Pts with any response | 73.3% (11/15) | 64.3% (9/14) | 76.9% (10/13) | 66.7% (10/15) | <0.001 |
| p-value vs MTX alone | 0.001 | 0.008 | 0.002 | 0.009 | |
| Time post-infusion | | | | | |
| 1 Week | 0.0% (0/15) | 35.7% (5/14) | 7.7% (1/13) | 26.7% (4/15) | |
| 2 Weeks | 6.7% (1/15) | 28.6% (4/14) | 15.4% (2/13) | 20.0% (3/15) | |
| 4 Weeks[a] | 13.3% (2/15) | 28.6% (4/14) | 46.2% (6/13) | 40.0% (6/15) | 0.006 |
| 6 Weeks | 26.7% (4/15) | 42.9% (6/14) | 38.5% (5/13) | 33.3% (5/15) | |
| 8 Weeks[a] | 40.0% (6/15) | 50.0% (7/14) | 69.2% (9/13) | 33.3% (5/15) | <0.001 |
| 10 Weeks | 40.0% (6/15) | 50.0% (7/14) | 69.2% (9/13) | 40.0% (6/15) | |

TABLE 4-continued

Number of Patients Responding According To Paulus
50% Criteria At Each Evaluation Visit

| 12 Weeks[a] | 60.0% (9/15) | 35.7% (5/14) | 61.5% (8/13) | 40.0% (6/15) | <0.001 |
|---|---|---|---|---|---|
| 14 Weeks | 40.0% (6/15) | 35.7% (5/14) | 61.5% (8/13) | 40.0% (6/15) | |
| 16 Weeks[a] | 60.0% (9/15) | 50.0% (7/14) | 53.8% (7/13) | 40.0% (6/15) | <0.001 |
| 18 Weeks | 71.4% (10/14) | 46.2% (6/13) | 61.5% (8/13) | 57.1% (8/14) | |
| 20 Weeks | 53.3% (8/15) | 35.7% (5/14) | 46.2% (6/13) | 40.0% (6/15) | |
| 22 Weeks | 46.7% (7/15) | 14.3% (2/14) | 53.8% (7/13) | 26.7% (4/15) | |
| 26 Weeks[a] | 40.0% (6/15) | 14.3% (2/14) | 46.2% (6/13) | 20.0% (3/15) | 0.008 |

[a]Evaluation visits pre-specified for analysis.

Commensurate with the clinical response rates shown in Tables 2-4, most of the patients in the treatment groups demonstrating effectiveness of cA2 treatment received all 5 infusions of cA2 (Table 5). The principle reason for patients not receiving the complete dose regimen was because of lack of efficacy in the placebo group (methotrexate alone) and in the 1 mg/kg group not receiving methotrexate. All 15 patients in the 3 mg/kg group that received methotrexate completed the 5-infusion dose regimen.

centration which was sustained through 26 weeks in the patients who received 3 or 10 mg/kg cA2.

Figure 6A:
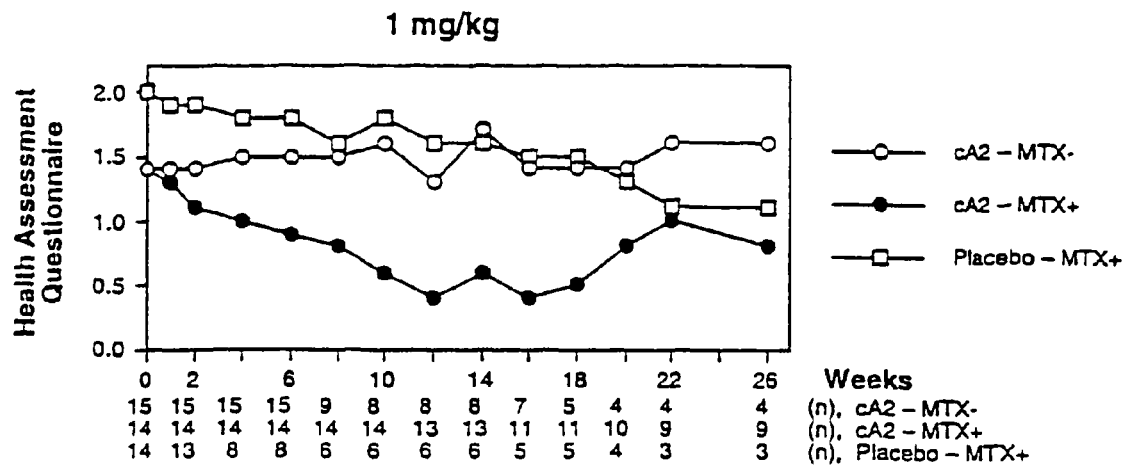
FIGS. 6A-6C are a set of three graphs showing the results over time for the Health Assessment Questionnaire (HAQ) in RA patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate; black circle=+methotrexate; square=placebo.
Figure 6B:
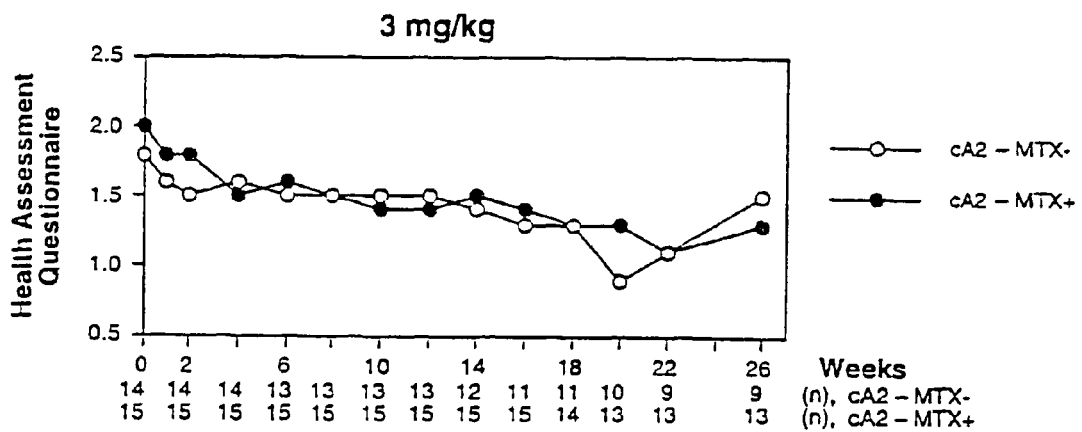
Figure 6C:
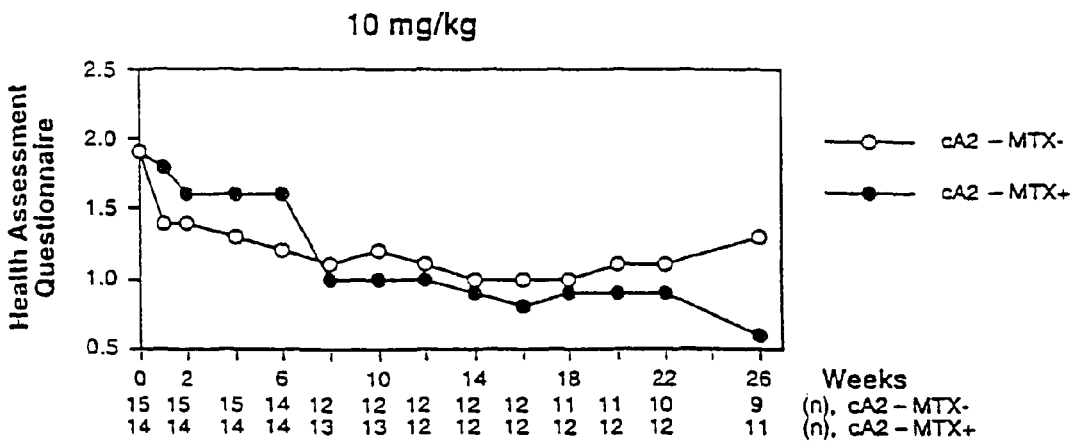

Results for the Health Assessment Questionnaire (HAQ) are shown in FIG. 6. This measurement of quality of life/disability demonstrated improvement over time corresponding with the clinical improvement observed in patients treated with cA2. In the patients treated with 3 mg/kg cA2 and methotrexate, the HAQ decreased from 2.0 at baseline to 1.1 at 22 weeks.

TABLE 5

Number of Infusions Completed

| | Placebo | 1 mg/kg cA2 | | 3 mg/kg cA2 | | 10 mg/kg cA2 | | |
|---|---|---|---|---|---|---|---|---|
| | MTX+ (n = 14) | MTX+ (n = 14) | MTX− (n = 15) | MTX+ (N = 15) | MTX− (n = 14) | MTX+ (n = 14) | MTX− (n = 15) | Treatment effect p-value |
| | | | Pts with complete[a] infusions | | | | | |
| 5 infusions | 6 (42.86%) | 12 (85.71%) | 8 (53.33%) | 15 (100.00%) | 12 (85.71%) | 12 (85.71%) | 12 (80.00%) | 0.003 |
| 4 infusions | 0 (0.00%) | 1 (7.14%) | 0 (0.00%) | 0 (0.00%) | 1 (7.14%) | 1 (7.14%) | 0 (0.00%) | |
| 3 infusions | 2 (14.29%) | 1 (7.14%) | 6 (40.00%) | 0 (0.00%) | 0 (0.00%) | 1 (7.14%) | 1 (6.67%) | |
| 2 infusions | 5 (35.71%) | 0 (0.00%) | 1 (6.67%) | 0 (0.00%) | 1 (7.14%) | 0 (0.00%) | 2 (13.33%) | |
| 1 infusion | 1 (7.14%) | 0 (0.00%) | 0 (0.00%) | 0 (0.00%) | 0 (0.00%) | 0 (0.00%) | 0 (0.00%) | |

[a]Patients are counted only once for the first group for which they qualify (5 infusions > 4 infusions etc. . . .). Patients were only counted if they had completed the entire infusion.

Results for measures of swollen and tender joint counts and the physician and patient global assessments are shown in FIGS. 1-4. The median results in FIGS. 1-4 were reported for each evaluation visit based only on the patients with data collected. That is, a last observation carried forward approach was not used for patients who dropped out. Instead, the number of patients with data that comprise each point on the graph was reported at the bottom of the figures.

Despite the number of drop-outs in the placebo group and the 1 mg/kg group not receiving methotrexate, the results in FIGS. 1-4 demonstrate that cA2 treatment in combination with methotrexate profoundly reduces disease activity for all of the traditional measurements of disease activity, approaching near remission in many patients.

Figure 5A:
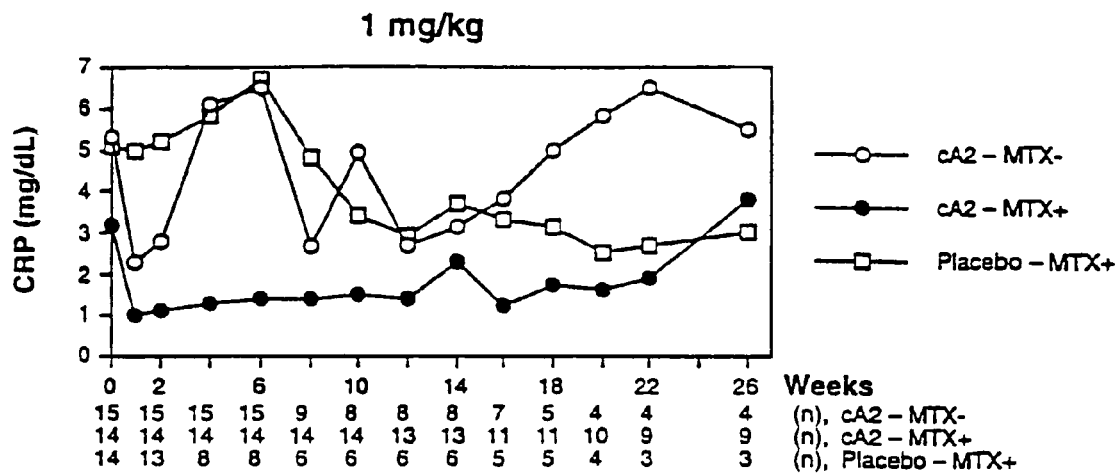
FIGS. 5A-5C are a set of three graphs showing the results over time for C-reactive protein (CRP) concentration in RA patients receiving cA2 treatment (1 mg/kg, 3 mg/kg or 10 mg/kg) with or without methotrexate. Results for the placebo group (methotrexate alone) are shown with the 1 mg/kg group. The number of patients with data at each evaluation visit is shown at the bottom of each graph. White circle=−methotrexate; black circle=+methotrexate; square=placebo.
Figure 5B:
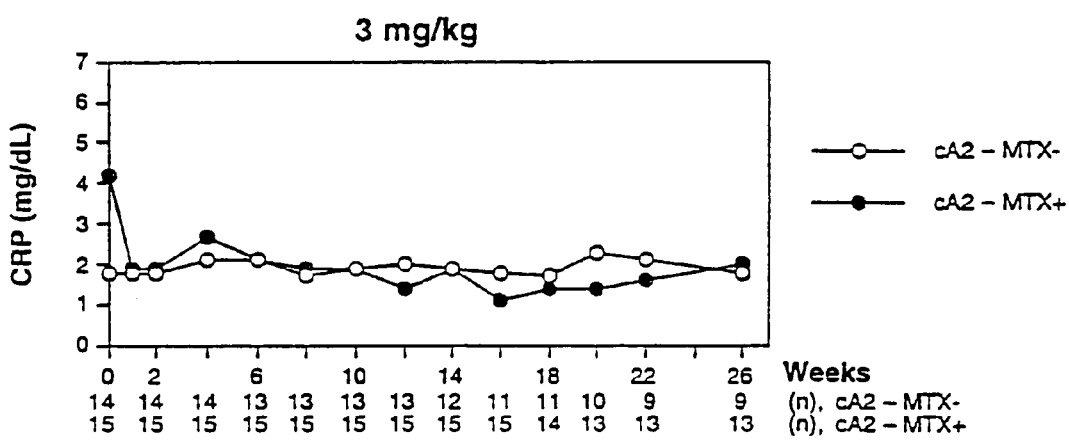
Figure 5C:
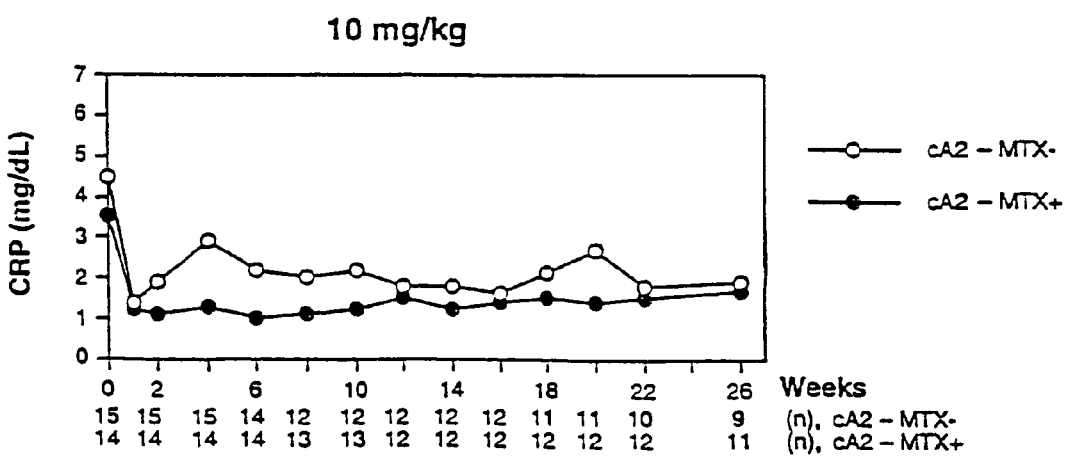

Results for a commonly used serum marker of inflammatory activity, C-reactive protein (CRP) are shown in FIG. 5. Treatment with cA2 produced a rapid decrease in CRP con- Pharmacokinetics of cA2

Serum concentrations of cA2 were obtained in all patients in this study. The serum concentration in each patient plotted over time according to the cA2 dose group is shown in FIG. 7. Data plotted are the serum cA2 concentrations obtained just before the administration of cA2 at weeks 2, 6, 10 and 14 and then at weeks 18 and 26. These sampling times were selected to best demonstrate the stability of the cA2 concentration during the multiple dose regimen and the decline in serum cA2 concentration after the last dose was administered. For purposes of data presentation, the scales for cA2 concentration for each graph are condensed as the cA2 dose was increased.

Substantial differences were observed for the cA2 serum concentration over time in the 1 mg/kg dose groups according to whether patients received methotrexate. Most of the patients receiving 1 mg/kg cA2 with methotrexate demonstrated measurable cA2 concentrations through 18 weeks, although it appeared that there was a tendency for the concentration to decline over time. In sharp contrast, the majority of patients who received 1 mg/kg cA2 without methotrexate were not able to maintain measurable serum concentrations of cA2 over time. As discussed herein, the inability to maintain serum cA2 in these patients was associated with a high rate of neutralizing antibody formation.

Figure 8A:
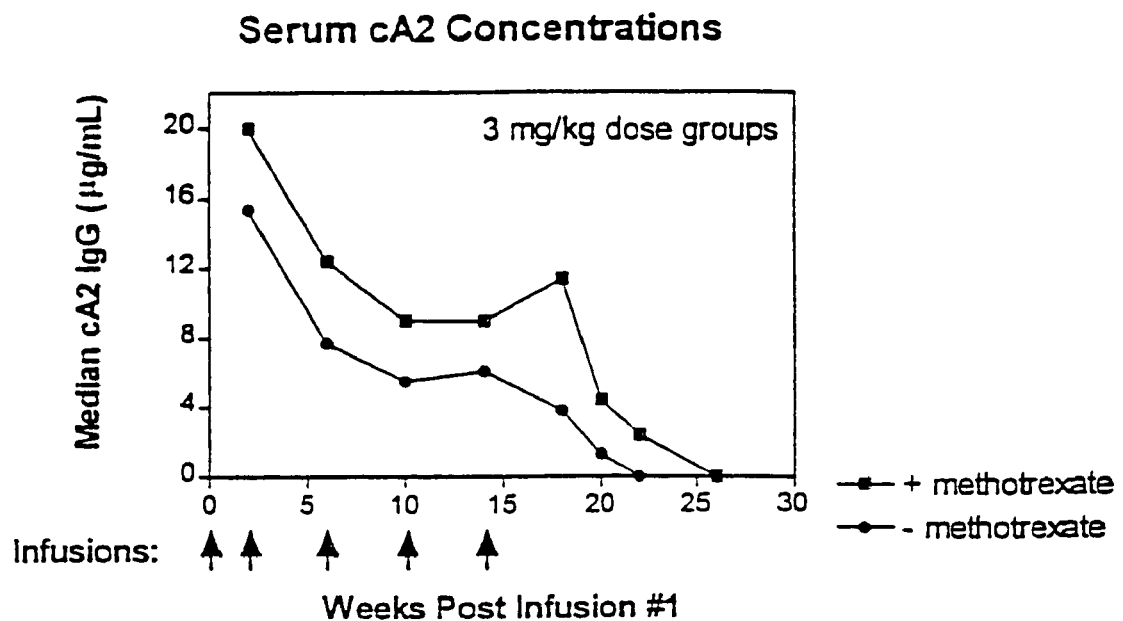
FIGS. 8A and 8B are a set of two graphs showing the median serum cA2 concentration over time in RA patients receiving 3 mg/kg cA2 (top panel) or 10 mg/kg cA2 (bottom panel) with or without methotrexate. Square=+methotrexate; circle or triangle=−methotrexate.
Figure 8B:
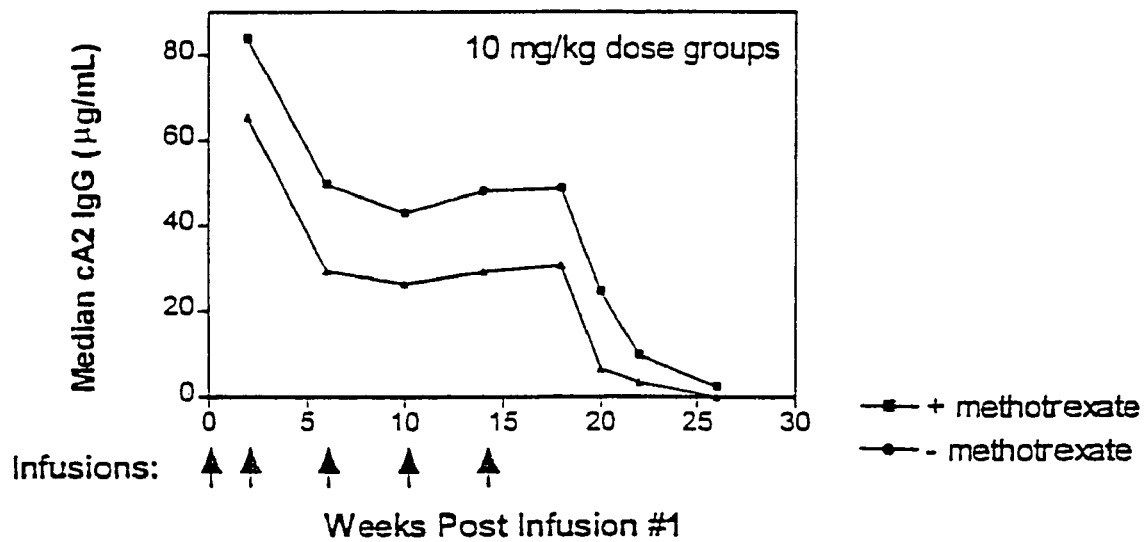

In contrast to the 1 mg/kg groups, patients who received either 3 mg/kg cA2 or 10 mg/kg cA2 were able to maintain serum cA2 concentrations through the multiple dose regimen. However, even in those dose groups, there was evidence that concomitant treatment with methotrexate was associated with high cA2 serum concentrations. As shown in FIG. 8, the median serum cA2 concentration in both the 3 and 10 mg/kg dose groups receiving methotrexate was higher than in the corresponding groups not receiving methotrexate.

Immune Responses to cA2

Serum samples were collected through 26 weeks from all patients and analyzed for human anti-chimeric antibodies (HACA) to cA2. The results for HACA responses for each cA2 treatment group are shown in Table 6. It should be noted that in several patients in the 3 mg/kg group and in most patients in the 10 mg/kg group, cA2 was still present in the 26-week sample and could potentially interfere with the detection of HACA in the assay. However, it could also be reasoned that if neutralizing antibodies were present at 26 weeks, then cA2 should not be present. Therefore, in presenting the data in Table 6, results for the immune response rate are shown not including patients with serum cA2 at 26 weeks and including patients with serum cA2 at 26 weeks, assuming that if cA2 was present at 26 weeks, the patient did not have a positive HACA response.

infusion rate and immunoglobulin aggregation. Investigators have reported that symptoms resolve in some patients by decreasing the rate of the infusion. Previous literature reports indicate that vasomotor symptoms have been observed in patients receiving intravenous immunoglobulin therapy (Berkman et al., *Ann. Intern Med.* 112:278-292 (1990); Ochs et al., *Lancet* 2:1158-1159 (1980)).

One patient developed hypotension during all three infusions of 10 mg/kg cA2. The patient did not display clinical signs of hypotension and did not require medical treatment, but, in keeping with predefined safety criteria, the treatment schedule of this patient was discontinued.

One patient treated with 3 infusions of 10 mg/kg of cA2 and with 7.5 mg/week methotrexate developed symptoms of sepsis as a result of staphylococcal pneumonia 2 weeks after her last study visit and 14 weeks after her last infusion with cA2. Six days after developing symptoms she was admitted to the hospital and treated. She died one day later. (This patient had not proceeded with the fourth infusion for reasons unrelated to the sepsis.) Patients with RA who develop infections have a worse than expected outcome. Wolfe and coworkers have reported an observed:expected ratio for death due to pneumonia of 5.307 and an observed:expected ratio for death due to infections (excluding pneumonia) of 6.213 in RA patients from the ARAMIS database (Wolfe et al., *Arthritis Rheumatism* 4:481-494 (1994)).

One patient experienced a serious postoperative infection following cataract surgery 9 weeks after the fifth and last infusion of 3 mg/kg of cA2 (with 7.5 mg/week methotrexate), leading to removal of the eye. This patient was receiving

TABLE 6

HACA Responses

| | 1 mg/kg | | 3 mg/kg | | 10 mg/kg | |
|---|---|---|---|---|---|---|
| | MTX+ | MTX− | MTX+ | MTX− | MTX+ | MTX− |
| HACA responses not including pts with 26-week serum cA2 | 2/13 (15.4%) | 8/15 (53.3%) | 0/10 (0%) | 3/12 (25.0%) | 0/2 (0%) | 1/10 (10%) |
| HACA responses including pts with 26-week serum cA2[1] | 2/13 (15.4%) | 8/15 (53.3%) | 0/15 (0%) | 3/14 (21.4%) | 0/14 (0%) | 1/15 (6.7%) |

[1]Patients with a measurable 26-week serum cA2 concentration were considered negative for a HACA response for this analysis.

The results in Table 6 demonstrate that concomitant methotrexate treatment suppresses the immune response to cA2, enabling stable pharmacokinetics to be achieved in a multiple dose regimen of cA2. This effect was also found after combined anti-CD4/anti-TNF antibody treatment in mice with collagen-induced arthritis and described in U.S. application Ser. No. 08/607,419, filed Feb. 28, 1996, the teachings of which are entirely incorporated herein by reference.

Clinical Safety

Two out of 86 patients (with most patients receiving 5 treatments) experienced multisystem infusion-related reactions with retreatment. Multisystem, infusion-related reactions include headache, fever, facial flushing, pruritus, myalgia, nausea, chest tightness, dyspnea, vomiting, erythema, abdominal discomfort, diaphoresis, shivers, hypertension, lightheadedness, hypotension, palpitations and somnolence.

Hypersensitivity reactions, as described herein, may occur whenever protein-containing materials, such as cA2, are administered. Thus, it is unclear whether these symptoms represent an immunologic event or physical factors such as prednisolone (7 mg/day). The incidence of endophthalmitis after cataract extraction has been reported to be between 0.072 and 0.093% (Kattan et al., *Ophthalmology* 98(9):1147-1148 (1991)) and may be heightened in patients receiving corticosteroid therapy.

Eight (9%) of 87 patients developed double stranded (ds)-DNA antibodies following multiple infusions of cA2. Measurements were performed at baseline, week 8, 16 and 26 (12 weeks following the last infusion). In these patients with antibodies against ds-DNA, there was a trend toward a lower level in antibodies at the last evaluation, with two patients being negative.

One patient developed dyspnea, pleuritic chest pain and a rebound of arthritis activity at study week 14 (four weeks after the fourth infusion of 3 mg/kg of cA2). Symptoms resolved and she received her fifth dose of cA2. Symptoms recurred 3 weeks later. Examination of the serial blood samples revealed that the test for antinuclear antibodies and anti ds-DNA antibodies were negative prior to treatment, but became positive at week 6 of the study. The patient's symptoms responded to oral prednisolone 20-30 mg daily. The working diagnosis was systemic lupus erythematosus (SLE). The patient currently does not have symptoms of SLE but has active RA.

To date, although antibodies to ds-DNA have been detected in patients treated with cA2, they generally represent transient increases and only one patient has been symptomatic. In patients who have had sufficient follow-up, anti-ds-DNA antibodies have resolved with discontinuation of treatment.

In summary, treatment with cA2 is well tolerated. The reductions in disease activity produced by cA2 are significant as supported by the findings of a low placebo response rate. High clinical response rates are obtained with a multiple dose regimen of 3 mg/kg cA2 in combination with 7.5 mg/wk methotrexate and can be sustained through 26 weeks. This dose regimen is considered preferable to the 1 mg/kg plus methotrexate regimen because better pharmacokinetics are obtained, virtually no immune response was detected and the clinical response is better sustained following the last treatment with cA2. The clinical benefit obtained by increasing the dose regimen to 10 mg/kg cA2 plus methotrexate is similar to that observed with the 3 mg/kg cA2 plus methotrexate regimen.

Thus, the results of this study indicate that treatment with a multiple dose regimen of cA2 as adjunctive and/or concomitant therapy to methotrexate therapy, in RA patients whose disease is incompletely controlled by methotrexate, produces a highly beneficial or synergistic clinical response that can be sustained through 26 weeks. The benefit produced by cA2 generally exceeds 50% reductions in the traditional measurements of rheumatoid arthritis (swollen and tender joints, patient and physician global disease assessments) and achieves near clinical remission in many patients. Accordingly, the results of this study indicate that treatment with multiple infusions of cA2 as adjunctive and/or concomitant therapy to methotrexate therapy is an important and efficacious therapeutic approach for treating RA in patients.

Example 2

Clinical Treatment of Rheumatoid Arthritis by Single Infusion of an Anti-TNF Antibody in Patients Receiving Methotrexate A randomized, double-blind, placebo controlled study was conducted to evaluate the effects of a single infusion of placebo, 5, 10 or 20 mg/kg cA2 in combination with methotrexate, administered at a dose of 10 mg/week, in the treatment of rheumatoid arthritis (RA) in patients.

Patients

Twenty-eight (28) RA patients at three centers in the United States who, despite receiving three months therapy with methotrexate administered at a stable dose of 10 mg/wk for at least 4 weeks prior to screening, still had active disease according to the criteria of the American College of Rheumatology, were enrolled in the study. Active disease was defined by the presence of six or more swollen joints plus at least three of four secondary criteria (duration of morning stiffness $\geq 45$ minutes; $\geq 6$ tender or painful joints; erythrocyte sedimentation rate (ESR)$\geq 28$ mm/hour; C-reactive protein (CRP)$\geq 20$ mg/l.

Patients taking NSAIDs and corticosteroids (prednisone) at screening were allowed to continue at stable doses (7.5 mg/day).

Study Infusions

The chimeric monoclonal anti-TNF antibody (cA2) was supplied as a sterile solution containing 5 mg cA2 per ml of 0.01 M phosphate-buffered saline in 0.15 M sodium chloride with 0.01% polysorbate 80, pH 7.2. The placebo vials contained 0.1% human serum albumin in the same buffer. Before use, the appropriate amount of cA2 or placebo was diluted to 300 ml in sterile saline by the pharmacist, and administered intravenously via a 0.2 μm in-line filter over 2 hours. The characteristics of the placebo cA2 infusion bags were identical, and the investigators and patients did not know which infusion was being administered.

Assessments

Patients were randomized to one of four treatment groups (7 patients per group). Each of the 28 patients received a single dose of either 0, 5, 10 or 20 mg/kg cA2 and were followed for 12 weeks. Patients continued treatment with methotrexate (Pharmacochemie, Netherlands) administered at 10 mg/week throughout the study. Patients were monitored for adverse events during infusions and regularly thereafter, by interviews, physical examination, and laboratory testing.

The primary measurement of clinical response was defined by the ACR preliminary definition of response (Felson et al., *Arthritis Rheumatism* 38(6):727-735 (1995)). Patients were considered to have a response if they had a 20% reduction in swollen and tender joint count, and had experienced a 20% reduction in 3 of the 5 following assessments: patient's assessment of pain (VAS), patient's global assessment of disease activity (VAS), physician's global assessment of disease activity (VAS), patient's assessment of physical function (HAQ), and an acute phase reactant (ESR). The ESR was measured at each study site with a standard method (Westergen).

Evaluations were performed at day 3, and at weeks 1, 2, 4, 6, 8, 10, and 12.

Results

The 28 patients were randomized to one of four treatment (or dose) groups.

The clinical response rates over time by ACR 20% criteria in each of the treatment groups is shown in Table 7.

TABLE 7

Clinical Response Rates (By ACR 20% Criteria)
In Patients Receiving 10 mg/kg Methotrexate

| | | Dose of cA2 | | | cA2 Treated |
|---|---|---|---|---|---|
| | Pts evaluated | Placebo 7 | 5 mg/kg 7 | 10 mg/kg 7 | 20 mg/kg 7 | Patients 21 |
| Pts with any response | | 1(14.3%) | 6(85.7%) | 5(71.4%) | 6(85.7%) | 17(81.0%) |
| 1 Week | | 0(0.0%) | 4(57.1%) | 2(28.6%) | 5(71.4%) | 11(52.4%) |

TABLE 7-continued

Clinical Response Rates (By ACR 20% Criteria)
In Patients Receiving 10 mg/kg Methotrexate

| | | Dose of cA2 | | | cA2 Treated |
|---|---|---|---|---|---|
| Pts evaluated | Placebo 7 | 5 mg/kg 7 | 10 mg/kg 7 | 20 mg/kg 7 | Patients 21 |
| 2 Weeks | 0(0.0%) | 4(57.1%) | 5(71.4%) | 5(71.4%) | 14(66.7%) |
| 4 Weeks | 1(14.3%) | 3(42.9%) | 5(71.4%) | 5(71.4%) | 13(61.9%) |
| 6 Weeks | 0(0.0%) | 3(42.9%) | 5(71.4%) | 4(57.1%) | 12(57.1%) |
| 8 Weeks | 1(14.3%) | 3(42.9%) | 4(57.1%) | 4(57.1%) | 11(52.4%) |
| 10 Weeks | 1(14.3%) | 1(14.3%) | 4(57.1%) | 3(42.9%) | 8(38.1%) |
| 12 Weeks | 1(14.3%) | 2(28.6%) | 4(57.1%) | 3(42.9%) | 9(42.9%) |

Clinical benefit of cA2 treatment was evident at the first evaluation visit at one week. Although each of the 3 doses of cA2 produced clinical responses in the majority of patients treated, the duration of clinical response appeared to be better sustained through 12 weeks in the groups receiving 10 or 20 mg/kg cA2. Clinical response was achieved much more frequently among patients receiving cA2 as compared to placebo. That is, 17/21 (81%) patients in the 3 cA2 groups achieved a response, compared with only 1/7 (14%) placebo treated patients. The magnitude of clinical response was notable. The mean tender joint count among cA2 treated patients decreased from 30.1 at baseline to 13.3 at week 12, and mean CRP decreased from 3.0 at baseline to 1.1 at week 12.

The duration of clinical response appeared to be dose dependent. 2/6 (33%) of the responding patients treated with 5 mg/kg cA2 sustained a response through 12 weeks of follow-up, compared to 7/11 (64%) of the responding patients who received 10 or 20 mg/kg. Treatment in all groups was generally well tolerated.

In summary, the results of this study indicate that treatment with cA2 as adjunctive and/or concomitant therapy to methotrexate therapy is effective in the reduction of the signs and symptoms of rheumatoid arthritis in patients whose disease is incompletely controlled by methotrexate. Moreover, the clinical response achieved by this approach can be sustained for more than 12 weeks after a single treatment. Accordingly, the results of this study indicate that treatment with cA2 as adjunctive and/or concomitant therapy to methotrexate therapy is an important and efficacious therapeutic approach for treating RA in patients.

Example 3

Clinical Treatment of Rheumatoid Arthritis by Repeated Dose Administration of an Anti-TNF Antibody in Patients Following a Single Dose, Double-Blind, Placebo-Controlled Trial An open label study was conducted to evaluate the effects of repeated infusions of 10 mg/kg cA2 in combination with methotrexate, administered at a dose of 10 mg/week, in the treatment of rheumatoid arthritis in patients.

Patients

As described in Example 2, a randomized, double-blind, placebo controlled, 12 week study of cA2 was conducted in RA patients who had active disease despite receiving three months therapy with methotrexate administered at a stable dose of 10 mg/wk for at least 4 weeks prior to screening.

At week 12, patients who had completed the 12 week evaluation period and had not experienced adverse events prohibiting further infusions of cA2, were offered 3 subsequent open label infusions of cA2, administered at a dose of 10 mg/kg, at eight week intervals (weeks 12, 20, 28). Twenty-three (23) patients from the 12 week study were enrolled in this study.

Assessments

11/23 patients entering this open label study were evaluated at 1 of 3 centers in the United States and followed up to 40 weeks after initial entry. Patients continued treatment with methotrexate administered at 10 mg/week throughout the study. Repeated treatments with cA2 were generally well tolerated. Three patients had transient infusion related symptoms (urticaria, somnolence).

The primary measurement of clinical response was defined by the ACR preliminary definition of response (Felson et al., *Arthritis Rheumatism* 38(6):727-735 (1995)). Patients were considered to have a response if they had a 20% reduction in swollen and tender joint count, and had experienced a 20% reduction in 3 of the 5 following assessments: patient's assessment of pain (VAS), patient's global assessment of disease activity (VAS), physician's global assessment of disease activity (VAS), patient's assessment of physical function (HAQ), and an acute phase reactant (ESR). The ESR was measured at each study site with a standard method (Westergen).

Results

Of six patients who had all received cA2 during the double-blinded study described in Example 2 and responded through the 12 weeks of that study, four patients sustained a response throughout the 40 week follow-up. Of the remaining two patients, one patient is still responding through week 28, and one patient recently entered this open label trial. For all 4 patients completing 40 weeks of follow-up and the patient at week 28, final tender joint counts were 2 and swollen joint counts 1, compared to a mean of 23 and 29, respectively, at entry into the double-blinded study described in Example 2. For 4 of these 5 patients, ESR were 18 ml/hr and CRP 0.7, compared to a mean of 27 and 3.9, respectively, at entry into the double-blind study described in Example 2.

Of two patients who had both received cA2 during the double-blinded study described in Example 2 and responded only through week 10 of that study, one patient responded through 36 weeks and one patient is still responding through week 20.

Of three patients who did not respond during the double-blinded study described in Example 2 (2 received placebos, 1 received 5 mg/kg cA2), two of these patients experienced a transient clinical response, and one patient is still responding through week 20.

In summary, the preliminary results of this study suggest that repeated adjunctive and/or concomitant therapy with cA2, in RA patients whose disease is incompletely controlled by methotrexate, can result in substantial clinical improvement for a majority of the patients. Moreover, the clinical response achieved by this approach can be sustained for up to 40 weeks of follow-up. Accordingly, the results of this study indicate that repeated treatment with cA2 as adjunctive and/or concomitant therapy to methotrexate therapy is an important and efficacious therapeutic approach for treating RA in patients.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of treating an individual suffering from rheumatoid arthritis whose active disease is incompletely controlled despite already receiving methotrexate comprising adjunctively administering with methotrexate therapy a different composition comprising a soluble human p75 tumor necrosis factor-α receptor or functional fragment thereof to the individual, wherein the soluble human p75 anti-tumor necrosis factor-α receptor or functional fragment thereof (a) binds to human tumor necrosis factor-α and (b) is administered at a dosage of 0.01-100 mg/kg and wherein such administration reduces or eliminates signs and symptoms associated with rheumatoid arthritis.

2. The method of claim 1, wherein the soluble human p75 tumor necrosis factor-α receptor is a multimeric molecule.

3. The method of claim 1, wherein the soluble human p75 tumor necrosis factor-α receptor is a soluble human p75 tumor necrosis factor-α immunoreceptor fusion protein.

4. The method of claim 3, wherein the soluble human p75 tumor necrosis factor-α immunoreceptor fusion protein is a p75 tumor necrosis factor-α receptor/IgG fusion protein.

5. A method for adjunctive treatment of an individual suffering from rheumatoid arthritis who still has active disease despite prior therapy with methotrexate and who is already being treated with methorexate comprising administering to the individual with methotrexate therapy a different composition comprising a soluble human p75 tumor necrosis factor-α receptor wherein such administration reduces or eliminates signs and symptoms associated with rheumatoid arthritis.

6. A method of treating an individual suffering from rheumatoid arthritis and already receiving methotrexate whose active disease is incompletely controlled by methotrexate comprising administering to the individual a different composition comprising a soluble human p75 tumor necrosis factor-α receptor and wherein the soluble human p75 tumor necrosis factor receptor-α is administered repeatedly as adjunctive therapy to methotrexate therapy and wherein such administration reduces or eliminates signs and symptoms associated with the rheumatoid arthritis.

7. The method of claim 6, wherein the soluble human p75 tumor necrosis factor-α receptor is administered as a repeated infusion of 10 mg/kg, and the methotrexate is administered at a dose of 10 mg/week.

8. The method of claim 5, wherein the soluble human p75 tumor necrosis factor-α receptor is administered as adjunctive and/or concomitant therapy to methotrexate therapy.

9. The method of claim 5, wherein methotrexate is administered at an interval of a week or weeks and the soluble human p75 tumor necrosis factor-α receptor is administered as multiple infusions.

10. A method of treating an individual suffering from active rheumatoid arthritis despite already receiving methotrexate comprising administering a soluble human p75 tumor necrosis factor-α receptor to the individual, wherein the soluble human p75 tumor necrosis factor-α receptor binds specifically to human tumor necrosis factor-α, wherein the soluble human p75 tumor necrosis factor-α receptor is administered in a different composition, in single or multiple doses, as adjunctive therapy to methotrexate therapy, wherein the methotrexate is administered in multiple doses and wherein such administration reduces or eliminates signs and symptoms associated with the arthritis.

* * * * *

SEQUENCE LISTING

```
<160> NUMBER OF SEQ ID NOS: 2

<210> SEQ ID NO 1
<211> LENGTH: 22
<212> TYPE: PRT
<213> ORGANISM: Homo sapiens

<400> SEQUENCE: 1

Tyr Ser Gln Val Leu Phe Lys Gly Gln Gly Cys Pro Ser Thr His Val
1               5                   10                  15

Leu Leu Thr His Thr Ile
            20

<210> SEQ ID NO 2
<211> LENGTH: 22
<212> TYPE: PRT
<213> ORGANISM: Homo sapiens

<400> SEQUENCE: 2

Tyr Gln Thr Lys Val Asn Leu Leu Ser Ala Ile Lys Ser Pro Cys Gln
1               5                   10                  15

Arg Glu Thr Pro Glu Gly
            20
```